(12) United States Patent
Hogg et al.

(10) Patent No.: US 9,309,248 B2
(45) Date of Patent: Apr. 12, 2016

(54) AZAINDOLINES

(71) Applicant: Hoffmann-La Roche Inc., Nutley, NJ (US)

(72) Inventors: Joan Heather Hogg, Caldwell, NJ (US); Robert Francis Kester, West Orange, NJ (US); Weiling Liang, Fremont, CA (US); Weiya Yun, Warren, NJ (US)

(73) Assignee: HOFFMANN-LA ROCHE INC., Nutley, NJ (US)

( * ) Notice: Subject to any disclaimer, the term of this patent is extended or adjusted under 35 U.S.C. 154(b) by 0 days.

(21) Appl. No.: 14/433,216

(22) PCT Filed: Oct. 8, 2013

(86) PCT No.: PCT/EP2013/070881
§ 371 (c)(1),
(2) Date: Apr. 2, 2015

(87) PCT Pub. No.: WO2014/056871
PCT Pub. Date: Apr. 17, 2014

(65) Prior Publication Data
US 2015/0266879 A1    Sep. 24, 2015

Related U.S. Application Data

(60) Provisional application No. 61/712,305, filed on Oct. 11, 2012.

(51) Int. Cl.
| | |
|---|---|
| *C07D 401/02* | (2006.01) |
| *C07D 401/10* | (2006.01) |
| *A61K 31/437* | (2006.01) |
| *A61K 31/4353* | (2006.01) |
| *C07D 471/16* | (2006.01) |
| *C07D 471/04* | (2006.01) |

(52) U.S. Cl.
CPC ............ *C07D 471/16* (2013.01); *C07D 471/04* (2013.01)

(58) Field of Classification Search
CPC .. C07D 401/02; C07D 401/10; A61K 31/437; A61K 31/4353
USPC .......................................... 546/113; 514/300
See application file for complete search history.

(56) References Cited

U.S. PATENT DOCUMENTS

2015/0252072 A1* 9/2015 Hogg ................. C07K 5/06026
514/19.3

FOREIGN PATENT DOCUMENTS

| EP | 0618221 | 10/1994 |
|---|---|---|
| WO | 02094263 | 11/2002 |
| WO | 2006017295 | 2/2006 |
| WO | 2009136290 | 11/2009 |
| WO | 2010080503 | 7/2010 |
| WO | 2011059763 | 5/2011 |

OTHER PUBLICATIONS

The English translation of the letter of opposition in the corresponding Costa Rican Application No. 2015-0148, which was notified by the Costa Rican Patent Office on Aug. 3, 2015.
The International Search Report and Written Opinion, mailed on Nov. 13, 2013, in the corresponding PCT Appl. No. PCT/EP2013/070881.
Willoughby et al., "Discovery of Potent, Selective Human Granzyme B Inhibitors that Inhibit CTL Mediated Apoptosis," Bioorganic & Medicinal Chemistry Letters 12 (2002) 2197-2200.
Leftheris et al., "Development of Highly Potent Inhibitors of Ras Farnesyltransferase Possessing Cellular and in Vivo Activity," J. Med. Chem. 1996, 39, 224-236.

\* cited by examiner

*Primary Examiner* — Niloofar Rahmani

(57) ABSTRACT

Disclosed are compounds of Formula (I), or pharmaceutically acceptable salts thereof, wherein W, Y, Z, $R^1$, $R^2$, $R^3$ and $R^4$ are as described in this application, and methods of using the compounds in the treatment of cancer.

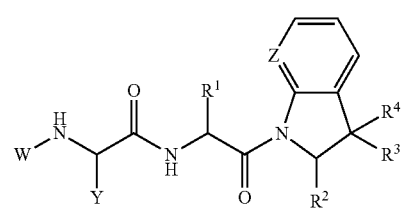

30 Claims, No Drawings

AZAINDOLINES

CROSS-REFERENCE TO RELATED APPLICATIONS

This application is a National Stage Application of PCT/EP2013/070881 filed Oct. 8, 2013, which claims priority from U.S. Provisional Patent Application No. 61/712,305, filed on Oct. 11, 2012. The priority of both said PCT and U.S. Provisional Patent Application are claimed. Each of the prior mentioned applications is hereby incorporated by reference herein in its entirety.

FIELD OF THE INVENTION

The present invention relates to azaindolines which act as inhibitors of SMAC protein binding to Inhibitor of Apoptosis Proteins (IAPs), and/or inhibitors of activated caspase protein binding to IAPs. These molecules are useful in the amelioration, treatment or control of cancer, especially solid tumors. These compounds bind to the BIR2 and/or BIR3 regions of IAP proteins, including XIAP and cIAP, resulting in activation or reactivation of the caspase cascade and, as such, are useful for the treatment of proliferative diseases, including cancer.

BACKGROUND OF THE INVENTION

Cancer is a disease of uncontrolled cell growth causing local expansion of a tumor and, potentially, distant metastases. One mechanism by which cancer cells grow is by avoidance of apoptosis, or programmed cell death. Alterations in apoptotic pathways have been linked to cancer cells being resistant to standard treatments, e.g., chemotherapeutics or radiation, and to the incidence and progression of cancer. See, e.g., E. Dean et al., "X-linked inhibitor of apoptosis protein as a therapeutic target," Expert Opin. Ther. Targets (2007) 11(11):1459-1471

The two basic pathways for apoptotic cell death are the intrinsic pathway and the extrinsic pathway. The intrinsic apoptotic pathway can be initiated by various mechanisms including cellular stress and drug-induced DNA damage. The extrinsic pathway can be initiated by activation of the death receptors by a chemokine. Initiation of either pathway results in the activation of a family of proteases called caspases. Once activated, the caspases can act to cleave a variety of substrates creating a cascade of events that lead to the activation of the effector caspases 3 and 7 and eventual cell death. The IAP family of proteins can bind to and inhibit the activity of caspases thus inhibiting apoptosis. See, e.g., Dean, supra at 1460.

The IAPs can contain up to three copies of homologous structural domains called baculoviral IAP repeat (BIR) domains, BIR1, BIR2 and BIR3. The BIR3 domain of the prototypical IAPs, cIAP and XIAP, can bind to and inhibit activated caspase 9. The BIR2 domain, in contrast, binds to and inhibits caspases 3 and 7. The proapoptotic protein Smac (also known as DIABLO) can block the BIR2 and BIR3 domains of IAPs competing with activated caspases resulting in release of the activated caspases from the IAPs and completion of the apoptotic program. See, e.g., S. Wang, "Design of Small-Molecule Smac Mimetics as IAP Antagonists," Current Topics in Microbiology and Immunology 348, DOI 10.100782_2010_111, pp. 89-113.

Peptides and small molecules have been reported to bind to the BIR3 region of XIAP and cIAP, mimicking the action of Smac protein and releasing activated caspases. See, e.g., Dean, supra; and M. Gyrd-Hansen et al., "IAPs: From caspase inhibitors to modulators of NF-κB, inflammation and cancer," Nature Review/Cancer, August 2010, Vol 10:561-574.

SUMMARY OF THE INVENTION

One aspect of the present invention is a compound of Formula I

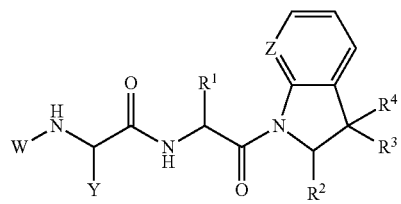

or pharmaceutically acceptable salts thereof, wherein W, Y, Z, $R^1$, $R^2$, $R^3$ and $R^4$ are as described in this application.

The present invention also relates to pharmaceutical compositions comprising one or more compounds of the invention, or a pharmaceutically acceptable salt thereof, and a pharmaceutically acceptable carrier or excipient.

The present invention further relates to a method of ameliorating, controlling or treating cancer, including specifically solid tumors, for example lung, pancreatic, colon, breast, bone and prostate cancers in a mammal, specifically a human, comprising administering to said mammal a therapeutically effective amount of a compound according to the invention or a pharmaceutically acceptable salt thereof.

DETAILED DESCRIPTION OF THE INVENTION

Definitions

Unless otherwise defined, all technical and scientific terms used herein have the same meaning as commonly understood by one of ordinary skill in the art to which this invention belongs.

As used herein, the following terms shall have the following definitions.

"Alkyl" means a monovalent linear or branched saturated hydrocarbon of 1 to 12 carbon atoms. In particular embodiments, alkyl has 1 to 6 carbon atoms, and in more particular embodiments 1 to 4 carbon atoms. As used herein, "lower alkyl" denotes an alkyl group having from 1-6 carbon atoms ("$C_{1-6}$-alkyl"). Examples of alkyl include methyl (Me), ethyl (Et), propyl, isopropyl, butyl (also known as n-butyl), isobutyl, sec-butyl, tert-butyl, pentyl, hexyl, and the like. The alkyl group can be optionally enriched in deuterium, e.g., —$CD_3$, —$CD_2CD_3$ and the like.

"Alkoxy" refers to an alkyl-O-group, whereby the alkyl is as defined herein. "$C_{1-6}$-alkoxy" refers to a $C_{1-6}$-alkyl-O-group, whereby the $C_{1-6}$-alkyl is as defined herein. Examples include methoxy (OMe), ethoxy (OEt) and the like.

"Aryl" means a monovalent aromatic carbocyclic mono-, bi- or tricyclic ring system comprising 6 to 19 carbon ring atoms. Examples of aryl moieties include, but are not limited to, phenyl, naphthyl (also known as naphthalenyl), tolyl, xylyl, pyridinyl, quinolinyl, pyrimidinyl, imidazolyl, thiazolyl, anthracenyl, tetrazolyl, and fluorenyl.

"Benzoyl" means the moiety phenyl-CO—.

"Benzyl" means the moiety phenyl-$CH_2$—

"Carbamoyl" means the moiety —CO—N—, "$C_{1-6}$-alkyl-carbamoyl" means —CO—N($C_{1-6}$-alkyl)$_2$.

"Cyano" means —C≡N.

"Cycloalkyl" means a substituted on unsubstituted stable monovalent saturated monocyclic, bicyclic or tricyclic system which consists of 3 to 10 ring carbon atoms. In particular embodiments, cycloalkyl denotes a monovalent saturated monocyclic hydrocarbon group of 3 to 8 ring carbon atoms, more particular 3-7 ring carbon atoms "$C_{3-7}$-cycloalkyl"). Particular cycloalkyl groups are monocyclic. Examples for monocyclic cycloalkyl are cyclopropyl, cyclobutnyl, cyclopentyl, cyclohexyl or cycloheptyl. Bicyclic means consisting of two saturated carbocycles having one or more carbon atoms in common. Examples for bicyclic cycloalkyl are bicyclo[2.2.1]heptanyl, or bicyclo[2.2.2]octanyl. Tricyclic means consisting of three saturated carbocycles having two or more carbon atoms in common. Examples of tricyclic cycloalkyl include adamantane "Halogen" or "Halo" means at atom selected from F, Cl, Br or I. In particular embodiments Halogen means F and Cl.

"Halogenalkyl" refers to an alkyl group as defined herein substituted by one or more halogen as defined herein. "Halogen-$C_{1-6}$-alkoxy" refers to a $C_{1-6}$-alkyl-group as defined herein substituted by one or more halogen as defined herein. Examples are $CF_3$, $CH_2$—$CF_3$ and the like.

"Heteroatom" means at atom selected from N, O or S.

"Heteroaryl" means a substituted or unsubstituted aromatic heterocyclic ring system containing up to two rings, at least one ring of which includes 1, 2, or 3 heteroatoms, the remaining ring atoms being carbon. Examples of heteroaryl groups include, but are not limited to, thienyl (also known as thiophenyl), furyl (also known as furanyl), indolyl, pyrrolyl, pyridinyl, pyrazinyl, oxazolyl, isoxazolyl, oxadiazolyl, thiazolyl, quinolinyl, isoquinolinyl, indazolyl, pyrimidinyl, imidazolyl, triazolyl, tetrazolyl, triazinyl, pyrazolyl, benzo[d]isoxazolyl, benzothiazolyl, 2-oxo-2H-chromen-4-yl, benzo[d]isoxazolyl, benzothiophenyl, benzoimidazolyl, naphthyridinyl and cinnolinyl.

In the case of a heteroaryl that is bicyclic it should be understood that one ring may be aryl while the other is heteroaryl and both may be independently substituted or unsubstituted.

"Heterocyclyl," "heterocycle" or "heterocyclic ring" means a substituted or unsubstituted monovalent saturated or partly unsaturated mono- or bicyclic ring, non-aromatic hydrocarbon system of 3 to 9 ring atoms, comprising 1, 2, or 3 ring heteroatoms selected from N, O and S, the remaining ring atoms being carbon. In particular embodiments, heterocycloalkyl is a monovalent saturated monocyclic ring system of 4 to 7 ring atoms, comprising 1, 2, or 3 ring heteroatoms selected from N, O and S, the remaining ring atoms being carbon. Examples for monocyclic saturated heterocycloalkyl are aziridinyl, oxiranyl, azetidinyl, oxetanyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, tetrahydrofuranyl, piperazinyl, morpholinyl, thiomorpholinyl, 1,1-dioxo-thiomorpholin-4-yl, azepanyl, diazepanyl, homopiperazinyl, or oxazepanyl. Examples of partly unsaturated heterocycloalkyl are dihydrofuryl, imidazolinyl, dihydro-oxazolyl, dihydro-oxadiazolyl, dihydro-triazolyl, tetrahydro-pyridinyl, tetrahydro-triazinyl or dihydropyranyl.

"oxo" means =O.

In the case of a heterocycle that is bicyclic it should be understood that one ring may be heterocycle while the other is cycloalkyl, and either or both may be independently substituted. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl.

"$IC_{50}$" refers to the concentration of a particular compound required to inhibit 50% of a specific measured activity. $IC_{50}$ can be measured, inter alia, as is described subsequently in Example 100.

"Oxo" or ("Oxy") means =O.

"Pharmaceutically acceptable," such as pharmaceutically acceptable carrier, excipient, etc., means pharmacologically acceptable and substantially non-toxic to the subject to which the particular compound is administered.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, trifluoroacetic acid and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., Ansel et al., Pharmaceutical Dosage Forms and Drug Delivery Systems (1995) at pgs. 456-457.

"Substituted," as in substituted alkyl, aryl or heteroaryl means that the substitution (i.e. replacement of one hydrogen atom) can occur at one or more positions and, unless otherwise indicated, that the substituents at each substitution site are independently selected from the specified options. The term "optionally substituted" refers to the fact that one or more hydrogen atoms of a chemical group (with one or more hydrogen atoms) can be, but does not necessarily have to be, substituted with another substituent.

The definitions described herein apply irrespective of whether the terms in question appear alone or in combination. It is contemplated that the definitions described herein can be appended to form chemically-relevant combinations, such as e.g. "heterocycloalkylaryl", "haloalkylheteroaryl", "arylalkylheterocycloalkyl", or "alkoxyalkyl". The last member of the combination is the radical which is binding to the rest of the molecule. The other members of the combination are attached to the binding radical in reversed order in respect of the literal sequence, e.g. the combination arylalkylheterocycloalkyl refers to a heterocycloalkyl-radical which is substituted by an alkyl which is substituted by an aryl.

As used in this application, if a formula or group appears to be missing a substituent, that is it appears the valence is not complete, it is presumed the missing substituent is an H.

In the structural formulae presented herein a broken bond (a) denotes that the substituent is below the plane of the paper and a wedged bond (b) denotes that the substituent is above the plane of the paper.

In one embodiment, the present invention relates to compounds of Formula I

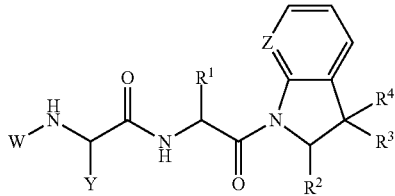

wherein
W is selected from the group
a) H,
b) alkyl that optionally includes 1-3 deuterium atoms,
c) alkyl that optionally may be substituted with $SO_2R^5$ and $OR^5$;
Y is alkyl that optionally may be substituted with $OR^5$;
Z is N;
$R^1$ is selected from the group
a) lower alkyl that optionally may be substituted with $SO_2R^5$,
b) cycloalkyl,
c) heterocyclyl, and
d) aryl;
$R^2$ is selected from the group
a) H
b) $C(O)NHR^6$,
c) heterocyclyl, and
d) heteroaryl;
$R^3$ and $R^4$ may be the same or different and each is independently selected from the group
a) H, and
b) lower alkyl;
$R^5$ is selected from the group
a) H,
b) lower alkyl,
c) $NR^7R^8$, and
d) aryl;
$R^6$ is selected from the group
a) H
b) aryl that optionally may be substituted with lower alkyl, $OR^5$, halogen, $C(O)OR^5$, $C(O)NR^7R^8$, aryl, heterocyclyl, $C(O)R^9$, $SO_2R^5$, cyano and $CF_3$,
c) lower alkyl that optionally may be substituted with $CF_3$, $SO_2R^5$ and aryl that optionally may be substituted with lower alkyl and halogen,
d) heteroaryl that optionally may be substituted with lower alkyl, $OR^5$, halogen, aryl and oxo, and
e) heterocyclyl;
$R^7$ and $R^8$ may be the same or different and each is independently selected from the group
a) H,
b) lower alkyl, and
c) aryl;
$R^9$ is selected from the group
a) lower alkyl, and
b) aryl;
or a pharmaceutically acceptable salt thereof.
In one embodiment, the present invention relates to compounds of Formula I wherein
W is selected from the group
a) H,
b) $C_{1-6}$-alkyl that optionally includes 1-3 deuterium atoms,
c) $C_{1-6}$-alkyl that optionally may be substituted with $SO_2R^5$ and $OR^5$;
Y is $C_{1-6}$-alkyl that optionally may be substituted with $OR^5$;
Z is N;
$R^1$ is selected from the group
a) $C_{1-6}$-alkyl that optionally may be substituted with $SO_2R^5$,
b) $C_{3-7}$-cycloalkyl,
c) heterocyclyl, and
d) aryl;
$R^2$ is selected from the group
a) H
b) $C(O)NHR^6$,
c) heterocyclyl, and
d) heteroaryl;
$R^3$ and $R^4$ may be the same or different and each is independently selected from the group
a) H, and
b) $C_{1-6}$-alkyl;
$R^5$ is selected from the group
a) H,
b) $C_{1-6}$-alkyl,
c) $NR^7R^8$, and
d) aryl;
$R^6$ is selected from the group
a) H
b) aryl that optionally may be substituted with $C_{1-6}$-alkyl, $OR^5$, halogen, $C(O)OR^5$, $C(O)NR^7R^8$, aryl, heterocyclyl, $C(O)R^9$, $SO_2R^5$, cyano and $CF_3$,
c) $C_{1-6}$-alkyl that optionally may be substituted with $CF_3$, $SO_2R^5$ and aryl that optionally may be substituted with $C_{1-6}$-alkyl and halogen,
d) heteroaryl that optionally may be substituted with $C_{1-6}$-alkyl, $OR^5$, halogen, aryl and oxo, and
e) heterocyclyl;
$R^7$ and $R^8$ may be the same or different and each is independently selected from the group
a) H,
b) $C_{1-6}$-alkyl, and
c) aryl;
$R^9$ is selected from the group
a) $C_{1-6}$-alkyl, and
b) aryl;
or a pharmaceutically acceptable salt thereof.
In one embodiment, the present invention relates to compounds of Formula I wherein
W is selected from $C_{1-6}$-alkyl, optionally substituted once by $CH_3$—O—, $CH_3$—$SO_2$— or OH;
Y is $C_{1-6}$-alkyl;
Z is N;
$R^1$ is selected from $C_{1-6}$-alkyl that is optionally substituted once by $CH_3$—$SO_2$—, $C_{3-7}$-cycloalkyl and heterocyclyl;
$R^2$ is selected from $C(O)NHR^6$, H and heteroaryl;
$R^3$ and $R^4$ may be the same or different and each is independently selected from H and $C_{1-6}$-alkyl;
$R^6$ is selected from,
a) H;
b) phenyl, optionally substituted by one, two or three substituents selected from benzoyl, $C_{1-6}$-alkyl, halogen-$C_{1-6}$-alkyl, —COO—$C_{1-6}$-alkyl, cyano, $C_{1-6}$-alkyl-carbamoyl-, $C_{1-6}$-alkoxy, —$SO_2$—$C_{1-6}$-alkyl, phenyl and piperidinyl;
c) benzyl, optionally substituted by one or two substituents selected from $C_{1-6}$-alkyl and halogen;
d) benzothiazolyl
e) $C_{1-6}$-alkyl;
f) halogen-$C_{1-6}$-alkyl g) halogen-phenyl-$CH_2$—;
h) $C_{1-6}$-alkyl-$SO_2$—$(CH_2)_2$—;
i) $C_{1-6}$-alkyl-thiazolyl;
j) $N(C_{1-6}$-alkyl$)_2$-$SO_2$—$(CH_2)_2$—;
k) naphthyl;
l) pyridinyl, optionally substituted by one substituent selected from $C_{1-6}$-alkyl and halogen;
m) pyrimidinyl;
n) 1H-benzoimidazolyl;
o) 1-methyl-1-phenyl-ethyl; and
p) 1-phenyl-ethyl
or a pharmaceutically acceptable salt thereof.

In one embodiment, the present invention relates to compounds of Formula I wherein
W is selected from $CD_3$, $CH_3$—O—$(CH_2)_2$—, $CH_3$—$SO_2$—$(CH_2)_2$—, ethyl, H, methyl and OH-ethyl;
Y is selected from methyl or ethyl;
Z is N;
$R^1$ is selected from $CH_3$—$SO_2$—$(CH_2)_2$—, $CH_3$—$CH_2$—$C(H,CH_3)$—, cyclohexyl, isopropyl and tetrahydropyranyl;
$R^2$ is selected from 1H-benzoimidazol-2-yl, $C(O)NHR^6$ and H;
$R^3$ and $R^4$ may be the same or different and each is independently selected from H and methyl;
$R^6$ is selected from,
a) H;
b) phenyl, optionally substituted by one, two or three substituents selected from benzoyl, Br, $CF_3$, Cl, $COOCH_3$, cyano, dimethylcarbamoyl, ethyl, F, methoxy, methyl, methylcarbamoyl, methyl-$SO_2$, phenyl and piperidinyl;
c) benzyl, optionally substituted by one or two substituents selected from Cl, F and methyl;
d) benzothiazolyl
e) $CF_3$—$CH_2$—;
f) ethyl;
g) methyl-$SO_2$—$(CH_2)_2$—;
h) methyl-thiazolyl;
i) $N(methyl)_2$-$SO_2$—$(CH_2)_2$—;
j) naphthyl;
k) pyridinyl, optionally substituted by one substituent selected from F and methyl;
l) pyrimidinyl;
m) 1H-benzoimidazolyl;
n) 1-methyl-1-phenyl-ethyl; and
o) 1-phenyl-ethyl
or a pharmaceutically acceptable salt thereof.

In one embodiment, the present invention relates to compounds of Formula I wherein
W is methyl;
Y is methyl;
Z is N;
$R^1$ is isopropyl;
$R^2$ is $C(O)NHR^6$;
$R^3$ and $R^4$ are H;
$R^6$ is selected from,
a) phenyl, optionally substituted by one, two or three substituents selected from benzoyl, Br, $CF_3$, Cl, $COOCH_3$, cyano, dimethylcarbamoyl, ethyl, F, methoxy, methyl, methylcarbamoyl, methyl-$SO_2$, phenyl and piperidinyl;
b) benzyl, optionally substituted by one or two substituents selected from Cl, F and methyl;
c) naphthyl;
d) 1-methyl-1-phenyl-ethyl; and
e) 1-phenyl-ethyl
or a pharmaceutically acceptable salt thereof.

One embodiment of the invention relates to compounds of Formula I wherein W is $C_{1-6}$-alkyl that optionally may be substituted as defined above, or a pharmaceutically acceptable salt of said compound. In a particular embodiment W is methyl.

Another embodiment of the invention relates to compounds of Formula I wherein Y is $C_{1-6}$-alkyl that optionally may be substituted as defined above, or a pharmaceutically acceptable salt of said compound. In a particular embodiment Y is methyl or ethyl.

Another embodiment of the invention relates to compounds of Formula I where I wherein $R^1$ is $C_{1-6}$-alkyl that optionally may be substituted as defined above, or a pharmaceutically acceptable salt of said compound. In a particular embodiment $R^1$ is propanyl.

Another embodiment of the invention relates to compounds of Formula I where $R^1$ is $C_{3-7}$-cycloalkyl, or a pharmaceutically acceptable salt of said compound. In a particular embodiment $R^1$ is cyclohexyl.

Another embodiment of the invention relates to compounds of Formula I where $R^1$ is heterocyclyl, or a pharmaceutically acceptable salt of said compound. In a particular embodiment $R^1$ is tetrahydropyranyl.

Another embodiment of the invention relates to compounds of Formula I where $R^1$ is aryl, or a pharmaceutically acceptable salt of said compound. In a particular embodiment $R^1$ is phenyl.

Another embodiment of the invention relates to compounds of Formula I where $R^2$ is H, or a pharmaceutically acceptable salt of said compound.

Another embodiment of the invention relates to compounds of Formula I where $R^2$ is heteroaryl, or a pharmaceutically acceptable salt of said compound. In a particular embodiment, $R^2$ is benzoimidazolyl.

Another embodiment of the invention relates to compounds of Formula I where $R^2$ is $C(O)NHR^6$, or a pharmaceutically acceptable salt of said compound. In a particular embodiment, $R^6$ is aryl that optionally may be substituted as defined above, including specifically phenyl and naphthalenyl. In another embodiment $R^6$ is $C_{1-6}$-alkyl that optionally may be substituted as defined above, including specifically methyl and ethyl. In another embodiment $R^6$ is heteroaryl that optionally may be substituted as defined above, including specifically pyridinyl, pyrimidinyl, thiazolyl and benzothiazolyl.

Another embodiment of the invention relates to compounds of Formula I wherein $R^3$ and $R^4$ are H, or a pharmaceutically acceptable salt of said compound.

Another embodiment of the invention relates to compounds of Formula I wherein one of $R^3$ and $R^4$ is H and the other is methyl, or a pharmaceutically acceptable salt of said compound.

Another embodiment of the invention relates to compounds of Formula I wherein $R^3$ and $R^4$ are methyl, or a pharmaceutically acceptable salt of said compound.

Another embodiment of the invention relates to compounds of Formula I wherein $R^5$ is $C_{1-6}$-alkyl, or a pharmaceutically acceptable salt of said compound. In a particular embodiment $R^5$ is methyl.

Another embodiment of the invention relates to compounds of Formula I wherein $R^5$ is aryl, or a pharmaceutically acceptable salt of said compound. In a particular embodiment $R^5$ is phenyl.

Another embodiment of the invention relates to compounds of Formula I where $R^6$ is aryl that optionally may be substituted with $C_{1-6}$-alkyl, $OR^5$, halogen, $C(O)OR^5$, $C(O)NR^7R^8$, aryl, heterocyclyl, $C(O)R^9$, $SO_2R^5$, cyano and $CF_3$, or a pharmaceutically acceptable salt of said compound.

Another embodiment of the invention relates to compounds of Formula I where $R^6$ is $C_{1-6}$-alkyl that optionally may be substituted with $CF_3$, $SO_2R^5$ and aryl that optionally may be substituted with $C_{1-6}$-alkyl and halogen, or a pharmaceutically acceptable salt of said compound.

Another embodiment of the invention relates to compounds of Formula I where $R^6$ is heteroaryl that optionally may be substituted with $C_{1-6}$-alkyl, $OR^5$, halogen, aryl and oxo, or a pharmaceutically acceptable salt of said compound.

Another embodiment of the invention relates to compounds of Formula I where W, Y and $R^1$ are $C_{1-6}$-alkyl; $R^2$ is $C(O)NHR^6$; $R^6$ is aryl that optionally may be substituted with halogen, $C_{1-6}$-alkyl, and $OR^5$; and $R^5$ is $C_{1-6}$-alkyl, or a pharmaceutically acceptable salt of said compound.

Another embodiment of the invention relates to compounds of Formula I where W, Y are $C_{1-6}$-alkyl; $R^1$ is heterocyclyl; $R^2$ is $C(O)NHR^6$; and $R^6$ is aryl that optionally may be substituted with halogen and $C_{1-6}$-alkyl, or a pharmaceutically acceptable salt thereof.

Compounds according to the invention wherein $R^2$ is $CONHR^6$ include:

(R,S)-1-[(S)-3-Methyl-2-((S)-2-methylamino-propionylamino)-butyryl]-2,3-dihydro-1H-pyrrolo[2,3-b]pyridine-2-carboxylic acid ethylamide (Example 1);

(R,S)-1-[(S)-2-Cyclohexyl-2-((S)-2-methylamino-propionylamino)-acetyl]-2,3-dihydro-1H-pyrrolo[2,3-b]pyridine-2-carboxylic acid ethylamide (Example 4);

(R,S)-1-[(S)-2-Cyclohexyl-2-((S)-2-methylamino-butyrylamino)-acetyl]-2,3-dihydro-1H-pyrrolo[2,3-b]pyridine-2-carboxylic acid ethylamide (Example 5);

(R,S)-1-[(2S,3S)-3-Methyl-2-((S)-2-methylamino-propionylamino)-pentanoyl]-2,3-dihydro-1H-pyrrolo[2,3-b]pyridine-2-carboxylic acid ethylamide (Example 6);

(R,S)-1-[(2S,3S)-3-Methyl-2-((S)-2-methylamino-butyrylamino)-pentanoyl]-2,3-dihydro-1H-pyrrolo[2,3-b]pyridine-2-carboxylic acid ethylamide (Example 7);

(R,S)-1-[(S)-3-Methyl-2-((S)-2-methylamino-propionylamino)-butyryl]-2,3-dihydro-1H-pyrrolo[2,3-b]pyridine-2-carboxylic acid amide (Example 8);

(R)-1-[(S)-3-Methyl-2-((S)-2-methylamino-propionylamino)-butyryl]-2,3-dihydro-1H-pyrrolo[2,3-b]pyridine-2-carboxylic acid (2-methoxy-phenyl)-amide (Example 9);

(S)-1-[(S)-3-Methyl-2-((S)-2-methylamino-propionylamino)-butyryl]-2,3-dihydro-1H-pyrrolo[2,3-b]pyridine-2-carboxylic acid (2-methoxy-phenyl)-amide (Example 10);

(S)-1-[(S)-3-Methyl-2-((S)-2-methylamino-propionylamino)-butyryl]-2,3-dihydro-1H-pyrrolo[2,3-b]pyridine-2-carboxylic acid phenylamide (Example 11);

(R)-1-[(S)-3-Methyl-2-((S)-2-methylamino-propionylamino)-butyryl]-2,3-dihydro-1H-pyrrolo[2,3-b]pyridine-2-carboxylic acid phenylamide (Example 12);

(R)-1-[(S)-3-Methyl-2-((S)-2-methylamino-propionylamino)-butyryl]-2,3-dihydro-1H-pyrrolo[2,3-b]pyridine-2-carboxylic acid o-tolylamide (Example 13);

(S)-1-[(S)-3-Methyl-2-((S)-2-methylamino-propionylamino)-butyryl]-2,3-dihydro-1H-pyrrolo[2,3-b]pyridine-2-carboxylic acid o-tolylamide (Example 14);

(R)-1-[(S)-3-Methyl-2-((S)-2-methylamino-propionylamino)-butyryl]-2,3-dihydro-1H-pyrrolo[2,3-b]pyridine-2-carboxylic acid benzylamide (Example 15);

(S)-1-[(S)-3-Methyl-2-((S)-2-methylamino-propionylamino)-butyryl]-2,3-dihydro-1H-pyrrolo[2,3-b]pyridine-2-carboxylic acid benzylamide (Example 16);

(S)-1-[(S)-3-Methyl-2-((S)-2-methylamino-propionylamino)-butyryl]-2,3-dihydro-1H-pyrrolo[2,3-b]pyridine-2-carboxylic acid 5-chloro-2-methyl-benzylamide (Example 17);

(S)-1-[(S)-3-Methyl-2-((S)-2-methylamino-propionylamino)-butyryl]-2,3-dihydro-1H-pyrrolo[2,3-b]pyridine-2-carboxylic acid biphenyl-2-ylamide (Example 18);

(S)-1-[(S)-3-Methyl-2-((S)-2-methylamino-propionylamino)-butyryl]-2,3-dihydro-1H-pyrrolo[2,3-b]pyridine-2-carboxylic acid naphthalen-1-ylamide (Example 19);

(R)-1-[(S)-3-Methyl-2-((S)-2-methylamino-propionylamino)-butyryl]-2,3-dihydro-1H-pyrrolo[2,3-b]pyridine-2-carboxylic acid (4-methyl-pyridin-3-yl)-amide (Example 20);

(S)-1-[(S)-3-Methyl-2-((S)-2-methylamino-propionylamino)-butyryl]-2,3-dihydro-1H-pyrrolo[2,3-b]pyridine-2-carboxylic acid (4-fluoro-phenyl)-amide (Example 21);

(S)-1-[(S)-3-Methyl-2-((S)-2-methylamino-propionylamino)-butyryl]-2,3-dihydro-1H-pyrrolo[2,3-b]pyridine-2-carboxylic acid (4-fluoro-2-methyl-phenyl)-amide (Example 22);

(S)-1-[(S)-3-Methyl-2-((S)-2-methylamino-propionylamino)-butyryl]-2,3-dihydro-1H-pyrrolo[2,3-b]pyridine-2-carboxylic acid (3,5-difluoro-phenyl)-amide (Example 23);

(S)-1-[(S)-3-Methyl-2-((S)-2-methylamino-propionylamino)-butyryl]-2,3-dihydro-1H-pyrrolo[2,3-b]pyridine-2-carboxylic acid 4-fluoro-benzylamide (Example 24);

(S)-1-[(S)-3-Methyl-2-((S)-2-methylamino-propionylamino)-butyryl]-2,3-dihydro-1H-pyrrolo[2,3-b]pyridine-2-carboxylic acid (2-chloro-phenyl)-amide (Example 25);

(S)-1-[(S)-3-Methyl-2-((S)-2-methylamino-propionylamino)-butyryl]-2,3-dihydro-1H-pyrrolo[2,3-b]pyridine-2-carboxylic acid (2-benzoyl-phenyl)-amide (Example 26);

(R)-1-[(S)-3-Methyl-2-((S)-2-methylamino-propionylamino)-butyryl]-2,3-dihydro-1H-pyrrolo[2,3-b]pyridine-2-carboxylic acid (2-benzoyl-phenyl)-amide (Example 27);

(S)-1-[(S)-3-Methyl-2-((S)-2-methylamino-propionylamino)-butyryl]-2,3-dihydro-1H-pyrrolo[2,3-b]pyridine-2-carboxylic acid (2,6-difluoro-phenyl)-amide (Example 28);

(R)-1-[(S)-3-Methyl-2-((S)-2-methylamino-propionylamino)-butyryl]-2,3-dihydro-1H-pyrrolo[2,3-b]pyridine-2-carboxylic acid (2,6-difluoro-phenyl)-amide (Example 29);

(S)-1-[(S)-3-Methyl-2-((S)-2-methylamino-propionylamino)-butyryl]-2,3-dihydro-1H-pyrrolo[2,3-b]pyridine-2-carboxylic acid (2-phenoxy-phenyl)-amide (Example 30);

(R)-1-[(S)-3-Methyl-2-((S)-2-methylamino-propionylamino)-butyryl]-2,3-dihydro-1H-pyrrolo[2,3-b]pyridine-2-carboxylic acid (2-phenoxy-phenyl)-amide (Example 31);

(S)-1-[(S)-3-Methyl-2-((S)-2-methylamino-propionylamino)-butyryl]-2,3-dihydro-1H-pyrrolo[2,3-b]pyridine-2-carboxylic acid (2-fluoro-6-methyl-phenyl)-amide (Example 32);

(S)-1-[(S)-3-Methyl-2-((S)-2-methylamino-propionylamino)-butyryl]-2,3-dihydro-1H-pyrrolo[2,3-b]pyridine-2-carboxylic acid (2,6-dimethyl-phenyl)-amide (Example 33);

(S)-1-[(S)-3-Methyl-2-((S)-2-methylamino-propionylamino)-butyryl]-2,3-dihydro-1H-pyrrolo[2,3-b]pyridine-2-carboxylic acid (2-fluoro-phenyl)-amide (Example 36);

(S)-1-[(S)-3-Methyl-2-((S)-2-methylamino-propionylamino)-butyryl]-2,3-dihydro-1H-pyrrolo[2,3-b]pyridine-2-carboxylic acid (2,2,2-trifluoro-ethyl)-amide (Example 37);

(S)-1-[(S)-3-Methyl-2-((S)-2-methylamino-propionylamino)-butyryl]-2,3-dihydro-1H-pyrrolo[2,3-b]pyridine-2-carboxylic acid (4-methyl-pyridin-3-yl)-amide (Example 38);

(S)-1-[(S)-3-Methyl-2-((S)-2-methylamino-propionylamino)-butyryl]-2,3-dihydro-1H-pyrrolo[2,3-b]pyridine-2-carboxylic acid (3-fluoro-phenyl)-amide (Example 39);

(S)-1-[(S)-3-Methyl-2-((S)-2-methylamino-propionylamino)-butyryl]-2,3-dihydro-1H-pyrrolo[2,3-b]pyridine-2-carboxylic acid (2-ethyl-phenyl)-amide (Example 40);

(S)-1-[(S)-3-Methyl-2-((S)-2-methylamino-propionylamino)-butyryl]-2,3-dihydro-1H-pyrrolo[2,3-b]pyridine-2-carboxylic acid (4-piperidin-4-yl-phenyl)-amide (Example 41);

(S)-1-[(S)-3-Methyl-2-((S)-2-methylamino-propionylamino)-butyryl]-2,3-dihydro-1H-pyrrolo[2,3-b]pyridine-2-carboxylic acid (4-benzoyl-phenyl)-amide (Example 42);

(S)-1-[(S)-3-Methyl-2-((S)-2-methylamino-propionylamino)-butyryl]-2,3-dihydro-1H-pyrrolo[2,3-b]pyridine-2-carboxylic acid (2,3-dimethyl-phenyl)-amide (Example 43);

(S)-1-[(S)-3-Methyl-2-((S)-2-methylamino-propionylamino)-butyryl]-2,3-dihydro-1H-pyrrolo[2,3-b]pyridine-2-carboxylic acid (2-fluoro-5-methyl-phenyl)-amide (Example 44);

(S)-1-[(S)-3-Methyl-2-((S)-2-methylamino-propionylamino)-butyryl]-2,3-dihydro-1H-pyrrolo[2,3-b]pyridine-2-carboxylic acid (3,5-dimethyl-phenyl)-amide (Example 45);

(S)-1-[(S)-3-Methyl-2-((S)-2-methylamino-propionylamino)-butyryl]-2,3-dihydro-1H-pyrrolo[2,3-b]pyridine-2-carboxylic acid (2-fluoro-4-methyl-phenyl)-amide (Example 46);

(S)-1-[(S)-3-Methyl-2-((S)-2-methylamino-propionylamino)-butyryl]-2,3-dihydro-1H-pyrrolo[2,3-b]pyridine-2-carboxylic acid (2-fluoro-4-methoxy-phenyl)-amide (Example 47);

(S)-1-[(S)-3-Methyl-2-((S)-2-methylamino-propionylamino)-butyryl]-2,3-dihydro-1H-pyrrolo[2,3-b]pyridine-2-carboxylic acid (2-cyano-phenyl)-amide (Example 48);

3-Fluoro-4-({(S)-1-[(S)-3-methyl-2-((S)-2-methylamino-propionylamino)-butyryl]-2,3-dihydro-1H-pyrrolo[2,3-b]pyridine-2-carbonyl}-amino)-benzoic acid methyl ester (Example 49);

(S)-1-[(S)-3-Methyl-2-((S)-2-methylamino-propionylamino)-butyryl]-2,3-dihydro-1H-pyrrolo[2,3-b]pyridine-2-carboxylic acid (2-fluoro-4-methanesulfonyl-phenyl)-amide (Example 50);

(S)-1-[(S)-3-Methyl-2-((S)-2-methylamino-propionylamino)-butyryl]-2,3-dihydro-1H-pyrrolo[2,3-b]pyridine-2-carboxylic acid (2-methanesulfonyl-ethyl)-amide (Example 51);

(S)-1-[(S)-3-Methyl-2-((S)-2-methylamino-propionylamino)-butyryl]-2,3-dihydro-1H-pyrrolo[2,3-b]pyridine-2-carboxylic acid (1-phenyl-ethyl)-amide (Example 52);

(S)-1-[(S)-3-Methyl-2-((S)-2-methylamino-propionylamino)-butyryl]-2,3-dihydro-1H-pyrrolo[2,3-b]pyridine-2-carboxylic acid (2-dimethylsulfamoyl-ethyl)-amide (Example 53);

(S)-1-[(S)-3-Methyl-2-((S)-2-methylamino-propionylamino)-butyryl]-2,3-dihydro-1H-pyrrolo[2,3-b]pyridine-2-carboxylic acid (1-methyl-1-phenyl-ethyl)-amide (Example 54);

(S)-1-[(S)-3-Methyl-2-((S)-2-methylamino-propionylamino)-butyryl]-2,3-dihydro-1H-pyrrolo[2,3-b]pyridine-2-carboxylic acid 5-fluoro-2-methyl-benzylamide (Example 55);

(S)-1-[(S)-3-Methyl-2-((S)-2-methylamino-propionylamino)-butyryl]-2,3-dihydro-1H-pyrrolo[2,3-b]pyridine-2-carboxylic acid pyrimidin-5-ylamide (Example 56);

(S)-1-[(S)-3-Methyl-2-((S)-2-methylamino-propionylamino)-butyryl]-2,3-dihydro-1H-pyrrolo[2,3-b]pyridine-2-carboxylic acid naphthalen-2-ylamide (Example 57);

(S)-1-[(S)-3-Methyl-2-((S)-2-methylamino-propionylamino)-butyryl]-2,3-dihydro-1H-pyrrolo[2,3-b]pyridine-2-carboxylic acid (4-cyano-2-fluoro-phenyl)-amide (Example 58);

(S)-1-[(S)-3-Methyl-2-((S)-2-methylamino-propionylamino)-butyryl]-2,3-dihydro-1H-pyrrolo[2,3-b]pyridine-2-carboxylic acid (2-fluoro-4-trifluoromethyl-phenyl)-amide (Example 59);

(S)-1-[(S)-3-Methyl-2-((S)-2-methylamino-propionylamino)-butyryl]-2,3-dihydro-1H-pyrrolo[2,3-b]pyridine-2-carboxylic acid (2,3-difluoro-phenyl)-amide (Example 60);

(S)-1-[(S)-3-Methyl-2-((S)-2-methylamino-propionylamino)-butyryl]-2,3-dihydro-1H-pyrrolo[2,3-b]pyridine-2-carboxylic acid (2,5-difluoro-phenyl)-amide (Example 61);

(S)-1-[(S)-3-Methyl-2-((S)-2-methylamino-propionylamino)-butyryl]-2,3-dihydro-1H-pyrrolo[2,3-b]pyridine-2-carboxylic acid (4-dimethylcarbamoyl-2-fluoro-phenyl)-amide (Example 62);

(S)-1-[(S)-3-Methyl-2-((S)-2-methylamino-propionylamino)-butyryl]-2,3-dihydro-1H-pyrrolo[2,3-b]pyridine-2-carboxylic acid (4-bromo-2-fluoro-phenyl)-amide (Example 63);

(S)-1-[(S)-3-Methyl-2-((S)-2-methylamino-propionylamino)-butyryl]-2,3-dihydro-1H-pyrrolo[2,3-b]pyridine-2-carboxylic acid (2-fluoro-4-methylcarbamoyl-phenyl)-amide (Example 64);

(S)-1-[(S)-3-Methyl-2-((S)-2-methylamino-propionylamino)-butyryl]-2,3-dihydro-1H-pyrrolo[2,3-b]pyridine-2-carboxylic acid (2,4-difluoro-phenyl)-amide (Example 65);

(S)-1-[(S)-3-Methyl-2-((S)-2-methylamino-propionylamino)-butyryl]-2,3-dihydro-1H-pyrrolo[2,3-b]pyridine-2-carboxylic acid (4-methyl-thiazol-2-yl)-amide (Example 66);

(S)-1-[(S)-3-Methyl-2-((S)-2-methylamino-propionylamino)-butyryl]-2,3-dihydro-1H-pyrrolo[2,3-b]pyridine-2-carboxylic acid (5-methyl-thiazol-2-yl)-amide (Example 67);

(S)-1-[(S)-3-Methyl-2-((S)-2-methylamino-propionylamino)-butyryl]-2,3-dihydro-1H-pyrrolo[2,3-b]pyridine-2-carboxylic acid benzothiazol-2-ylamide (Example 68);

(S)-1-[(S)-3-Methyl-2-((S)-2-methylamino-propionylamino)-butyryl]-2,3-dihydro-1H-pyrrolo[2,3-b]pyridine-2-carboxylic acid (3-fluoro-pyridin-4-yl)-amide (Example 69);

(S)-1-[(S)-3-Methyl-2-((S)-2-methylamino-propionylamino)-butyryl]-2,3-dihydro-1H-pyrrolo[2,3-b]pyridine-2-carboxylic acid (2-chloro-6-fluoro-phenyl)-amide (Example 70);

(S)-1-[(S)-3-Methyl-2-((S)-2-methylamino-propionylamino)-butyryl]-2,3-dihydro-1H-pyrrolo[2,3-b]pyridine-2-carboxylic acid (2-chloro-6-methyl-phenyl)-amide (Example 71);

(S)-1-[(S)-3-Methyl-2-((S)-2-methylamino-propionylamino)-butyryl]-2,3-dihydro-1H-pyrrolo[2,3-b]pyridine-2-carboxylic acid (2,4,6-trichloro-phenyl)-amide (Example 72);

(S)-1-[(S)-3-Methyl-2-((S)-2-methylamino-propionylamino)-butyryl]-2,3-dihydro-1H-pyrrolo[2,3-b]pyridine-2-carboxylic acid (2-fluoro-6-trifluoromethyl-phenyl)-amide (Example 73);

(S)-1-[(S)-3-Methyl-2-((S)-2-methylamino-propionylamino)-butyryl]-2,3-dihydro-1H-pyrrolo[2,3-b]pyridine-2-carboxylic acid (2,6-dichloro-phenyl)-amide (Example 74);

(S)-1-[(S)-3-Methyl-2-((S)-2-methylamino-propionylamino)-butyryl]-2,3-dihydro-1H-pyrrolo[2,3-b]pyridine-2-carboxylic acid (2-chloro-6-trifluoromethyl-phenyl)-amide (Example 75);

(S)-1-[(S)-2-Cyclohexyl-2-((S)-2-ethylamino-propionylamino)-acetyl]-2,3-dihydro-1H-pyrrolo[2,3-b]pyridine-2-carboxylic acid phenylamide (Example 76);

(S)-1-[(S)-2-((S)-2-Ethylamino-propionylamino)-3-methyl-butyryl]-2,3-dihydro-1H-pyrrolo[2,3-b]pyridine-2-carboxylic acid (2,6-difluoro-phenyl)-amide (Example 77);

(S)-1-[(S)-3-Methyl-2-((S)-2-methylamino-butyrylamino)-butyryl]-2,3-dihydro-1H-pyrrolo[2,3-b]pyridine-2-carboxylic acid (2,6-difluoro-phenyl)-amide (Example 78);

(R)-1-[(S)-2-Cyclohexyl-2-((S)-2-methylamino-propionylamino)-acetyl]-2,3-dihydro-1H-pyrrolo[2,3-b]pyridine-2-carboxylic acid phenylamide (Example 79);

(S)-1-[(S)-2-Cyclohexyl-2-((S)-2-methylamino-propionylamino)-acetyl]-2,3-dihydro-1H-pyrrolo[2,3-b]pyridine-2-carboxylic acid phenylamide (Example 80);

(R)-1-[(S)-2-Cyclohexyl-2-((S)-2-methylamino-butyrylamino)-acetyl]-2,3-dihydro-1H-pyrrolo[2,3-b]pyridine-2-carboxylic acid phenylamide (Example 81);

1-[(S)-2-Cyclohexyl-2-((S)-2-methylamino-butyrylamino)-acetyl]-2,3-dihydro-1H-pyrrolo[2,3-b]pyridine-2-carboxylic acid phenylamide (Example 82);

1-[(S)-2-Cyclohexyl-2-((S)-2-(d3-methyl)amino-butyrylamino)-acetyl]-2,3-dihydro-1H-pyrrolo[2,3-b]pyridine-2-carboxylic acid phenylamide (Example 83);

(S)-1-[(S)-2-((S)-2-Amino-propionylamino)-2-cyclohexyl-acetyl]-2,3-dihydro-1H-pyrrolo[2,3-b]pyridine-2-carboxylic acid phenylamide (Example 84);

(S)-1-[(S)-3-Methyl-2-((S)-2-methylamino-butyrylamino)-butyryl]-2,3-dihydro-1H-pyrrolo[2,3-b]pyridine-2-carboxylic acid phenylamide (Example 85);

(S)-1-[(S)-3-Methyl-2-((S)-2-(d3-methyl)amino-butyrylamino)-butyryl]-2,3-dihydro-1H-pyrrolo[2,3-b]pyridine-2-carboxylic acid phenylamide (Example 86);

(S)-1-[(S)-2-((S)-2-Ethylamino-propionylamino)-3-methyl-butyryl]-2,3-dihydro-1H-pyrrolo[2,3-b]pyridine-2-carboxylic acid phenylamide (Example 87);

(S)-1-[(S)-2-((S)-2-Ethylamino-butyrylamino)-3-methyl-butyryl]-2,3-dihydro-1H-pyrrolo[2,3-b]pyridine-2-carboxylic acid phenylamide (Example 88);

(S)-1-{(S)-2-[(S)-2-(2-Hydroxy-ethylamino)-propionylamino]-3-methyl-butyryl}-2,3-dihydro-1H-pyrrolo[2,3-b]pyridine-2-carboxylic acid phenylamide (Example 89);

(S)-1-{(S)-2-[(S)-2-(2-Hydroxy-ethylamino)-butyrylamino]-3-methyl-butyryl}-2,3-dihydro-1H-pyrrolo[2,3-b]pyridine-2-carboxylic acid phenylamide (Example 90);

(S)-1-{(S)-2-Cyclohexyl-2-[(S)-2-(2-hydroxy-ethylamino)-propionylamino]-acetyl}-2,3-dihydro-1H-pyrrolo[2,3-b]pyridine-2-carboxylic acid phenylamide (Example 91);

(S)-1-{(S)-2-[(S)-2-(2-Methanesulfonyl-ethylamino)-propionylamino]-3-methyl-butyryl}-2,3-dihydro-1H-pyrrolo[2,3-b]pyridine-2-carboxylic acid (2,6-difluoro-phenyl)-amide (Example 92);

(S)-1-{(S)-2-[(S)-2-(2-Methoxy-ethylamino)-propionylamino]-3-methyl-butyryl}-2,3-dihydro-1H-pyrrolo[2,3-b]pyridine-2-carboxylic acid (2,6-difluoro-phenyl)-amide (Example 93);

(S)-1-[(S)-2-((S)-2-Methylamino-propionylamino)-2-(tetrahydro-pyran-4-yl)-acetyl]-2,3-dihydro-1H-pyrrolo[2,3-b]pyridine-2-carboxylic acid (2,6-difluoro-phenyl)-amide (Example 94);

(R)-1-[(S)-2-((S)-2-Methylamino-propionylamino)-2-(tetrahydro-pyran-4-yl)-acetyl]-2,3-dihydro-1H-pyrrolo[2,3-b]pyridine-2-carboxylic acid (2,6-difluoro-phenyl)-amide (Example 95);

1-[(S)-4-Methanesulfonyl-2-((S)-2-methylamino-propionylamino)-butyryl]-2,3-dihydro-1H-pyrrolo[2,3-b]pyridine-2-carboxylic acid phenylamide (Example 96);

1-[(S)-4-Methanesulfonyl-2-((S)-2-methylamino-propionylamino)-butyryl]-2,3-dihydro-1H-pyrrolo[2,3-b]pyridine-2-carboxylic acid phenylamide (Example 97);

3-Methyl-1-[(S)-3-methyl-2-((S)-2-methylamino-propionylamino)-butyryl]-2,3-dihydro-1H-pyrrolo[2,3-b]pyridine-2-carb oxylic acid (2,6-difluoro-phenyl)-amide (Example 98);

(S)-1-[(S)-2-((S)-2-Methylamino-propionylamino)-2-(tetrahydro-pyran-4-yl)-acetyl]-2,3-dihydro-1H-pyrrolo[2,3-b]pyridine-2-carboxylic acid (2-fluoro-6-methyl-phenyl)-amide (Example 99); or a pharmaceutically acceptable salt of any of the foregoing compounds.

Compounds according to the invention wherein $R^2$ is heteroaryl include:

(S)—N—{(S)-1-[(S)-2-(1H-Benzoimidazol-2-yl)-2,3-dihydro-pyrrolo[2,3-b]pyridine-1-carbonyl]-2-methyl-propyl}-2-methylamino-propionamide (Example 34); and (S)—N—{(S)-1-[(R)-2-(1H-Benzoimidazol-2-yl)-2,3-dihydro-pyrrolo[2,3-b]pyridine-1-carbonyl]-2-methyl-propyl}-2-methylamino-propionamide (Example 35);

or a pharmaceutically acceptable salt of any of the foregoing compounds.

Compounds according to the invention wherein $R^2$ is H include:

(S)—N—[(S)-1-(3,3-Dimethyl-2,3-dihydro-pyrrolo[2,3-b]pyridine-1-carbonyl)-2-methyl-propyl]-2-methylamino-propionamide (Example 2); and (S)—N—[(S)-1-(3,3-Dimethyl-2,3-dihydro-pyrrolo[2,3-b]pyridine-1-carbonyl)-2-methyl-propyl]-2-methylamino-butyramide (Example 3);

or a pharmaceutically acceptable salt of any of the foregoing compounds.

Another embodiment of the invention relates to a compound selected from:

(S)—N—[(S)-1-(3,3-Dimethyl-2,3-dihydro-pyrrolo[2,3-b]pyridine-1-carbonyl)-2-methyl-propyl]-2-methylamino-butyramide (Example 3);

(S)-1-[(S)-3-Methyl-2-((S)-2-methylamino-propionylamino)-butyryl]-2,3-dihydro-1H-pyrrolo[2,3-b]pyridine-2-carboxylic acid o-tolylamide (Example 14);

(S)-1-[(S)-3-Methyl-2-((S)-2-methylamino-propionylamino)-butyryl]-2,3-dihydro-1H-pyrrolo[2,3-b]pyridine-2-carboxylic acid (2-chloro-phenyl)-amide (Example 25);

(S)-1-[(S)-3-Methyl-2-((S)-2-methylamino-propionylamino)-butyryl]-2,3-dihydro-1H-pyrrolo[2,3-b]pyridine-2-carboxylic acid (2,6-difluoro-phenyl)-amide (Example 28);

(S)-1-[(S)-3-Methyl-2-((S)-2-methylamino-propionylamino)-butyryl]-2,3-dihydro-1H-pyrrolo[2,3-b]pyridine-2-carboxylic acid (2-fluoro-6-methyl-phenyl)-amide (Example 32);

(S)-1-[(S)-3-Methyl-2-((S)-2-methylamino-propionylamino)-butyryl]-2,3-dihydro-1H-pyrrolo[2,3-b]pyridine-2-carboxylic acid (2-fluoro-phenyl)-amide (Example 36);

(S)-1-[(S)-3-Methyl-2-((S)-2-methylamino-propionylamino)-butyryl]-2,3-dihydro-1H-pyrrolo[2,3-b]pyridine-2-carboxylic acid (2-fluoro-5-methyl-phenyl)-amide (Example 44);

(S)-1-[(S)-3-Methyl-2-((S)-2-methylamino-propionylamino)-butyryl]-2,3-dihydro-1H-pyrrolo[2,3-b]pyridine-2-carboxylic acid (2-fluoro-4-methyl-phenyl)-amide (Example 46);

(S)-1-[(S)-3-Methyl-2-((S)-2-methylamino-propionylamino)-butyryl]-2,3-dihydro-1H-pyrrolo[2,3-b]pyridine-2-carboxylic acid (2-fluoro-4-methoxy-phenyl)-amide (Example 47);

(S)-1-[(S)-3-Methyl-2-((S)-2-methylamino-propionylamino)-butyryl]-2,3-dihydro-1H-pyrrolo[2,3-b]pyridine-2-carboxylic acid (2,5-difluoro-phenyl)-amide (Example 61);

(S)-1-[(S)-3-Methyl-2-((S)-2-methylamino-propionylamino)-butyryl]-2,3-dihydro-1H-pyrrolo[2,3-b]pyridine-2-carboxylic acid (4-bromo-2-fluoro-phenyl)-amide (Example 63);

(S)-1-[(S)-3-Methyl-2-((S)-2-methylamino-propionylamino)-butyryl]-2,3-dihydro-1H-pyrrolo[2,3-b]pyridine-2-carboxylic acid (2-chloro-6-fluoro-phenyl)-amide (Example 70);

(S)-1-[(S)-3-Methyl-2-((S)-2-methylamino-propionylamino)-butyryl]-2,3-dihydro-1H-pyrrolo[2,3-b]pyridine-2-carboxylic acid (2-chloro-6-methyl-phenyl)-amide (Example 71);

(S)-1-[(S)-3-Methyl-2-((S)-2-methylamino-propionylamino)-butyryl]-2,3-dihydro-1H-pyrrolo[2,3-b]pyridine-2-carboxylic acid (2,4,6-trichloro-phenyl)-amide (Example 72);

(S)-1-[(S)-3-Methyl-2-((S)-2-methylamino-propionylamino)-butyryl]-2,3-dihydro-1H-pyrrolo[2,3-b]pyridine-2-carboxylic acid (2,6-dichloro-phenyl)-amide (Example 74);

(S)-1-[(S)-3-Methyl-2-((S)-2-methylamino-butyrylamino)-butyryl]-2,3-dihydro-1H-pyrrolo[2,3-b]pyridine-2-carboxylic acid (2,6-difluoro-phenyl)-amide (Example 78);

(S)-1-[(S)-2-((S)-2-Methylamino-propionylamino)-2-(tetrahydro-pyran-4-yl)-acetyl]-2,3-dihydro-1H-pyrrolo[2,3-b]pyridine-2-carboxylic acid (2,6-difluoro-phenyl)-amide (Example 94);

3-Methyl-1-[(S)-3-methyl-2-((S)-2-methylamino-propionylamino)-butyryl]-2,3-dihydro-1H-pyrrolo[2,3-b]pyridine-2-carb oxylic acid (2,6-difluoro-phenyl)-amide (Example 98); and (S)-1-[(S)-2-((S)-2-Methylamino-propionylamino)-2-(tetrahydro-pyran-4-yl)-acetyl]-2,3-dihydro-1H-pyrrolo[2,3-b]pyridine-2-carboxylic acid (2-fluoro-6-methyl-phenyl)-amide (Example 99); or a pharmaceutically acceptable salt of any of the foregoing compounds.

The compounds of Formula I as well as their salts have at least one asymmetric carbon atom and therefore may be present as mixtures of different stereoisomers. The various isomers can be isolated by known separation methods, e.g., chromatography.

Compounds disclosed herein and covered by formula I above may exhibit tautomerism or structural isomerism. It is intended that the invention encompasses any tautomeric or structural isomeric form of these compounds, or mixtures of such forms, and is not limited to any one tautomeric or structural isomeric form depicted in the formulas above.

Dosages

The compounds of the invention preferably bind to BIR domains of an IAP preventing the IAP from binding to other proteins. Examples of Bir binding proteins include, but are not limited to, caspase 3, caspase 7, caspase 9, Smac and the like. Examples of IAPs include, but are not limited to, XIAP, cIAP1, cIAP2 or NAIP. In one aspect, the compound of the invention bind to the BIR2 and/or BIR3 domains of XIAP, cIAP1 and/or cIAP2. In another aspect, the compounds of the invention bind to the BIR2 domain of XIAP, cIAP1 and/or cIAP2.

Compounds of the invention are useful for inducing apoptosis in cells or sensitizing cells to apoptotic signals, in particular cancer cells. Apoptotic signals can be induced in cancer cells by, e.g., radiation therapy or antineoplastic chemotherapy. Alternatively, apoptotic signals can be induced in cancer cells by activation of the death receptors by death receptor agonists. Death receptor agonists can be naturally occurring, e.g., tumor necrosis factor α, (TNF-α) or non-naturally occurring, e.g., a synthetic antibody such as a DR4 or DR5 antibody.

The compounds of the present invention are thus useful in the amelioration, control or treatment of cell proliferative disorders such as, in particular, oncological disorders. These compounds and formulations containing said compounds are anticipated to be useful in the treatment or control of blood cancers, such as, for example, acute myeloid leukemia, or solid tumors, such as, for example, breast, colon, lung and prostate tumors.

A "therapeutically effective amount" or "effective amount" of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as one or more bolus injections or as a continuous infusion.

Pharmaceutical preparations useful in the practice of the invention, i.e., comprising the compounds of the invention can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions). Moreover, administration can be effected topically (e.g. in the form of ointments, creams or oils).

Compositions/Formulations

In an alternative embodiment, the present invention includes pharmaceutical compositions comprising at least one compound of formula I, or a pharmaceutically acceptable salt thereof, and a pharmaceutically acceptable excipient and/or carrier.

These pharmaceutical compositions can be suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, as well as the particular mode of administration. The amount of active ingredient which can be combined with a carrier material to produce a single dosage form will generally be that amount of a formula I compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

The compounds of Formula I and their pharmaceutically acceptable salts and esters can be processed with pharmaceutically inert, inorganic or organic adjuvants for the production of tablets, coated tablets, dragées and hard gelatin capsules. Lactose, polyvinylpyrrolidone, hydroxypropylmethylcellulose, hydroxypropylcellulose, microcrystalline cellulose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc. Suitable adjuvants for the production of solutions and syrups are, for example, H$_2$O, polyols, saccharose, invert sugar, glucose, etc. Suitable adjuvants for injection solutions are, for example, H$_2$O, alcohols, polyols, glycerol, vegetable oils, etc. Suitable adjuvants for suppositories are, for example, natural or hardened oils, waxes, fats, semi-solid or liquid polyols, etc. Suitable adjuvants for topical preparations are glycerides, semi-synthetic and synthetic glycerides, hydrogenated oils, liquid waxes, liquid paraffins, liquid fatty alcohols, sterols, polyethylene glycols and cellulose derivatives.

Moreover, the pharmaceutical preparations can contain preservatives, solubilizers, viscosity-increasing substances, stabilizers, wetting agents, emulsifiers, sweeteners, colorants, flavors, salts for varying the osmotic pressure, buffers, masking agents or antioxidants. They can also contain other therapeutic substances.

The compounds in the present invention (compounds of general Formula I) can be prepared using the general reaction scheme set out in the schemes below.

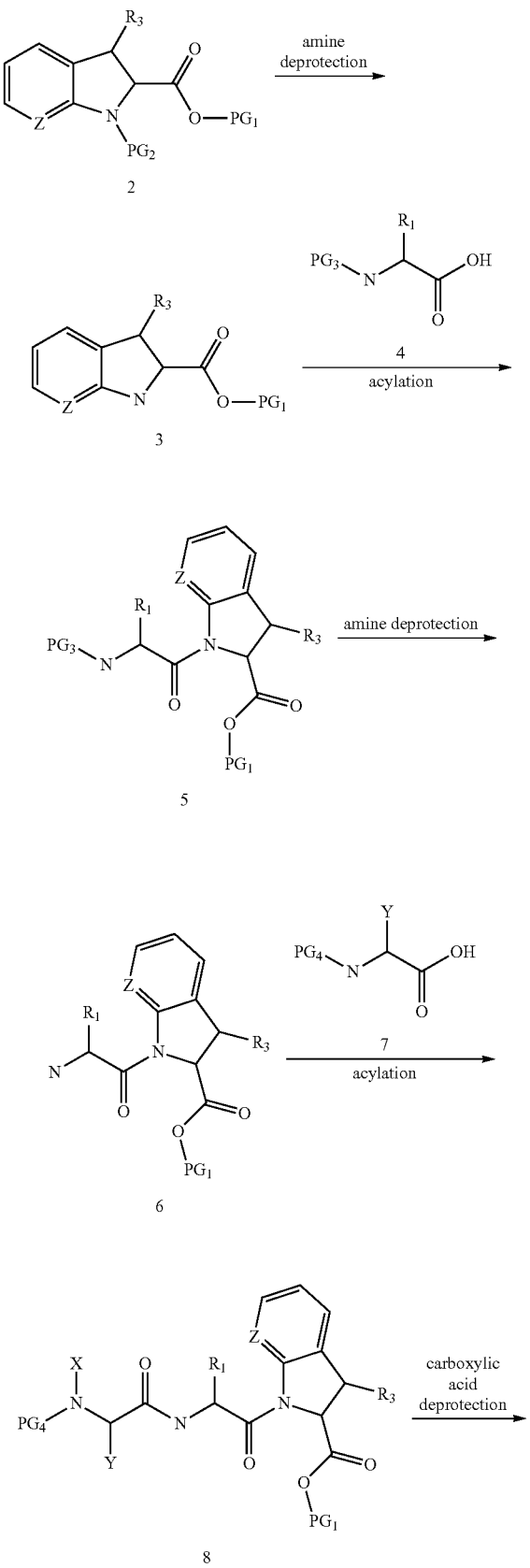

Scheme 1

-continued

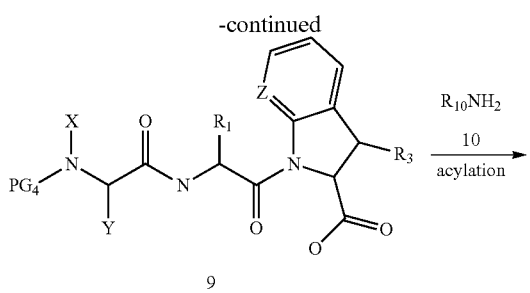

9

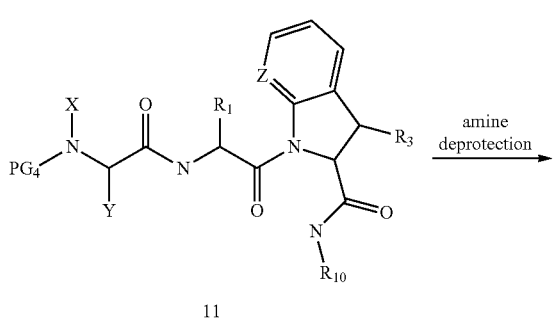

11

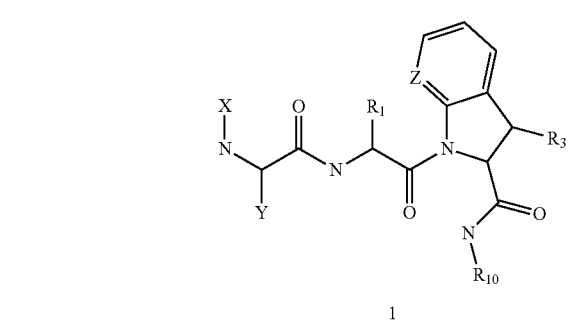

1

The amine protecting group PG2 of a suitably protected azaindoline of general structure 2 can be removed to afford compounds of general formula 3. Compounds of general formula 3 can be acylated with compounds of general formula 4 to give compounds of general formula 5. The acylation methods include, but are not limited to, acyl halides, acyl azides, and standard peptide coupling reagents. The amine protecting group PG3 in compounds of general formula 5 can be removed to afford compounds of general formula 6. Compounds of general formula 6 can be acylated with compounds of general formula 7 to give compounds of general formula 8. The acylation methods include, but are not limited to, standard peptide coupling reagents. The carboxylic acid protecting group PG1 of compounds of general structure 8 can be removed to form compounds of general structure 9. Compounds of general formula 9 can be treated with acylation reagents and an appropriate amine of general structure 10 to provide compounds of general formula 11. The amine protecting group PG4 can be removed to afford compound of general formula 1.

The order of the steps can be varied, as shown in Scheme 2 and Scheme 3.

Scheme 2

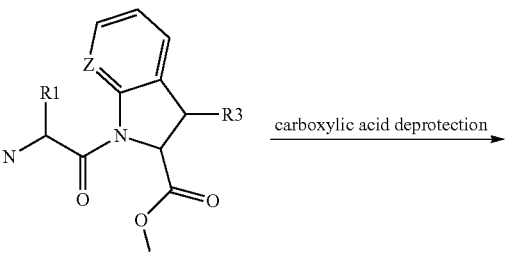

5

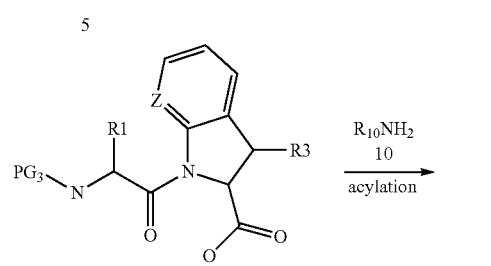

12

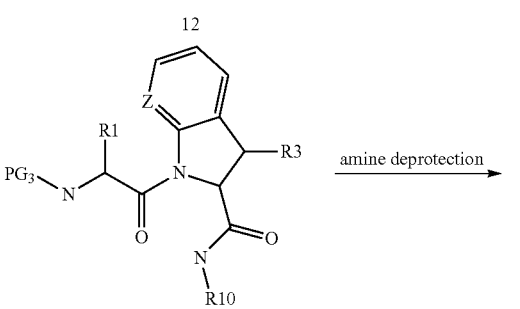

13

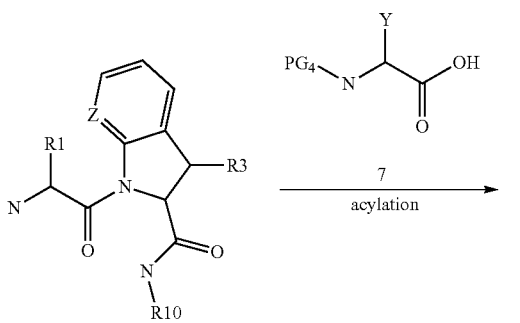

14

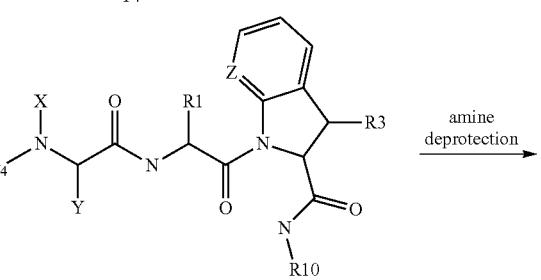

11

-continued

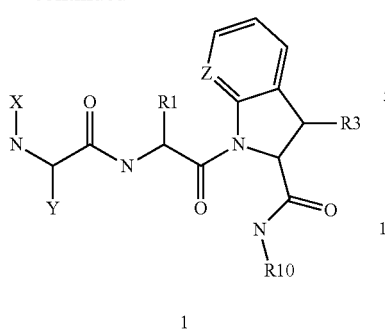

1

Scheme 3

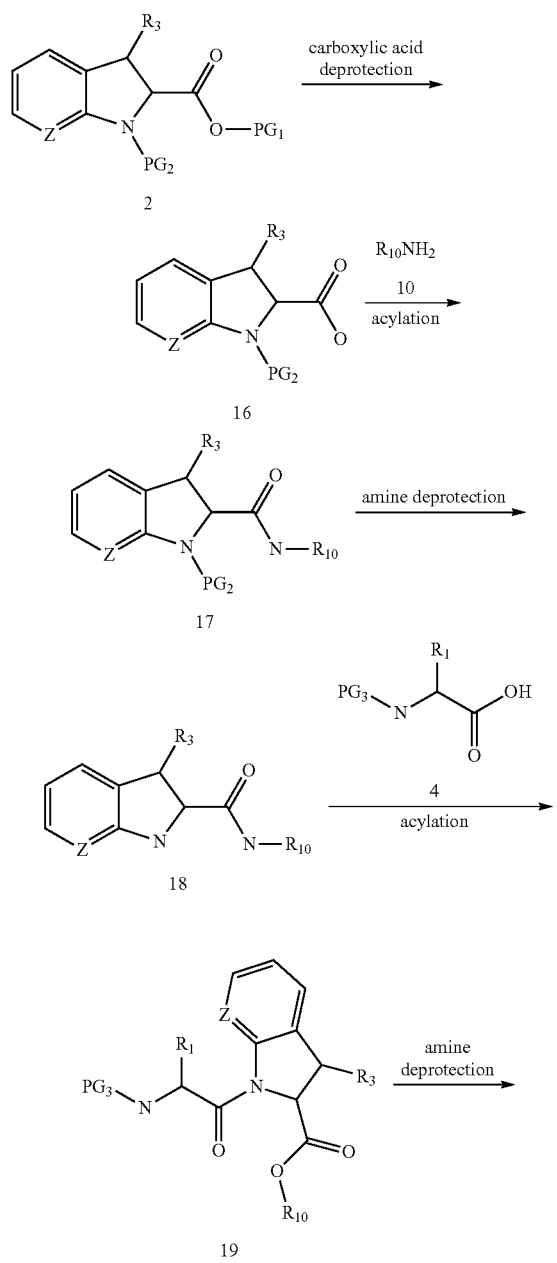

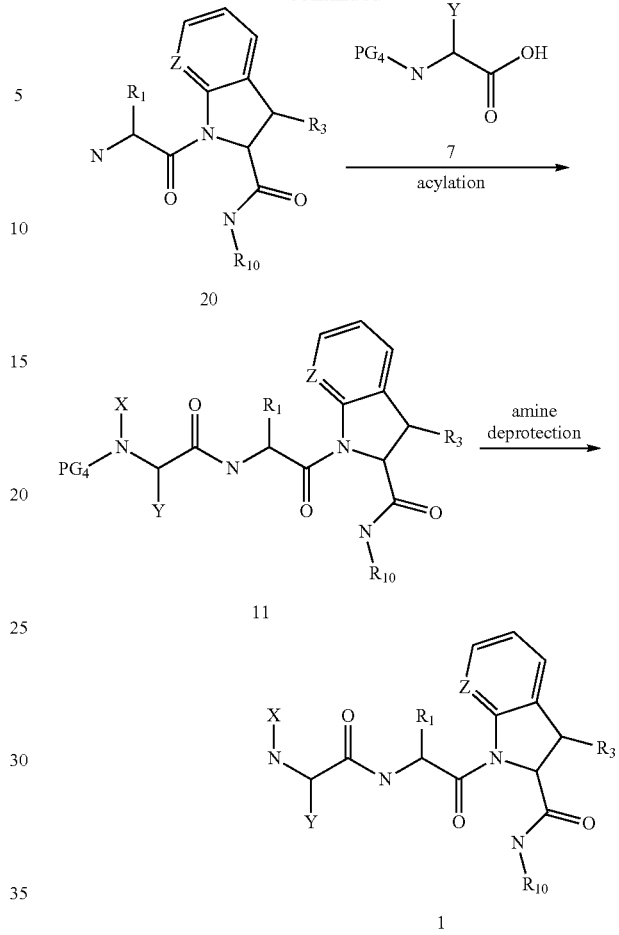

Methods to perform the above described reactions and processes would be apparent to those of ordinary skill in the art based on the present disclosure, or can be deduced in analogy from the examples. Starting materials are commercially available or can be made by methods analogous to those described in the Examples below.

Crystal Forms

When the compounds of the invention are solids, it is understood by those skilled in the art that these compounds, and their salts, may exist in different crystal or polymorphic forms, all of which are intended to be within the scope of the present invention and specified formulas.

EXAMPLES

The compounds of the present invention may be synthesized according to known techniques. The following examples and references are provided to aid the understanding of the present invention. The examples are not intended, however, to limit the invention, the true scope of which is set forth in the appended claims. The names of the reactants and final products in the examples were generated using AutoNom 2000 Add-in v4.0 SP2 (function in ISIS Draw, Elsevier/MDL), or AutoNom 2000 TT v4.01.305 (Elsevier/

Preparation of Intermediates

Intermediate 1

(R,S)-2,3-Dihydro-1H-pyrrolo[2,3-b]pyridine-2-carboxylic acid ethylamide

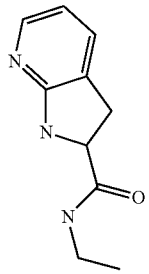

Step 1: In a 250 mL round-bottomed flask, 1-tert-butyl 2-methyl 2,3-dihydro-1H-pyrrolo[2,3-b]pyridine-1,2-dicarboxylate (prepared using methods of M Boehringer, et al. U.S. Pat. No. 7,417,144) (3.0 g, 10.8 mmol, Eq: 1.00) was combined with THF (18 mL) and MeOH (12 mL) to give a colorless solution. Lithium hydroxide monohydrate (452 mg, 10.8 mmol, Eq: 1.00) was added and the reaction was stirred at rt overnight. The crude reaction mixture was concentrated in vacuo to give lithium 1-(tert-butoxycarbonyl)-2,3-dihydro-1H-pyrrolo[2,3-b]pyridine-2-carboxylate as an off-white solid (2.9 g), m/z=265 (M+H).

Step 2: In a 100 mL round-bottomed flask, lithium 1-(tert-butoxycarbonyl)-2,3-dihydro-1H-pyrrolo[2,3-b]pyridine-2-carboxylate (400 mg, 1.48 mmol, Eq: 1.00), ethanamine hydrochloride (145 mg, 1.78 mmol, Eq: 1.2) and HATU (675 mg, 1.78 mmol, Eq: 1.2) were combined in DMF (6 mL) to give a light yellow suspension. Triethylamine (0.45 mL, 3.2 mmol, Eq: 2.2) was added. The reaction was stirred overnight then diluted with ethyl acetate (30 mL) and saturated aqueous NaHCO$_3$ (20 mL). The aqueous layer was separated, extracted with DCM (20 mL×2) and the combined organic layers were washed with 1 M aqueous NaOH (10 mL), dried over Na$_2$SO$_4$ and concentrated in vacuo. The residue was azeotroped with n-heptane (30 mL×3) to give tert-butyl 2-(ethylcarbamoyl)-2,3-dihydro-1H-pyrrolo[2,3-b]pyridine-1-carboxylate (322 mg), m/z=292 (M+H).

Step 3: In a 100 mL round-bottomed flask, tert-butyl 2-(ethylcarbamoyl)-2,3-dihydro-1H-pyrrolo[2,3-b]pyridine-1-carboxylate (402 mg, 1.38 mmol, Eq: 1.00) was combined with DCM (8 mL) to give a colorless solution. TFA (2 mL, 26.0 mmol, Eq: 18.8) was added and the reaction was stirred at rt for 6 h. The reaction mixture was concentrated in vacuo, saturated aqueous NaHCO$_3$ (30 mL) was added and the resulting mixture was extracted with DCM (20 mL×3). The organic layers were dried over Na$_2$SO$_4$ and concentrated in vacuo to give 2,3-dihydro-1H-pyrrolo[2,3-b]pyridine-2-carboxylic acid ethylamide as an off-white solid (210 mg), m/z=192 (M+H).

Intermediate 2

2,3-Dihydro-1H-pyrrolo[2,3-b]pyridine-2-carboxylic acid amide, trifluoroacetate salt

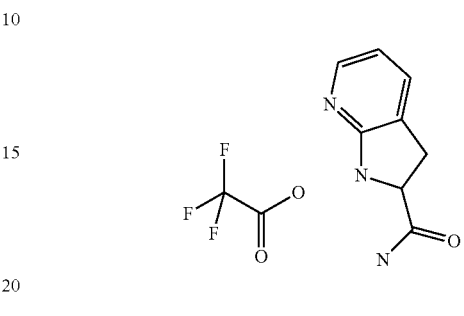

Step 1: To a solution of 1-tert-butyl 2-ethyl 2,3-dihydro-1H-pyrrolo[2,3-b]pyridine-1,2-dicarboxylate (prepared using methods of M Boehringer, et al. U.S. Pat. No. 7,417,144) (200 mg, 684 µmol, Eq: 1.00) in THF (1.2 mL) and MeOH (0.8 mL) was added LiOH (16.4 mg, 684 µmol, Eq: 1.00) in one portion. The reaction mixture was stirred at rt for 72 h. The reaction mixture was concentrated in vacuo and the residue treated with DCM (10 mL) to give lithium 1-(tert-butoxycarbonyl)-2,3-dihydro-1H-pyrrolo[2,3-b]pyridine-2-carboxylate as an off-white solid (200 mg) which was used without further purification.

Step 2: To a suspension of lithium 1-(tert-butoxycarbonyl)-2,3-dihydro-1H-pyrrolo[2,3-b]pyridine-2-carboxylate (100 mg, 370 µmol, Eq: 1.00) in DMF (5.00 mL) was added sequentially ammonium bicarbonate (90.0 mg, 1.14 mmol, Eq: 3.08), HATU (210 mg, 552 µmol, Eq: 1.49) and triethylamine (100 µL, 717 µmol, Eq: 1.94). The resulting dark yellow mixture was stirred at rt for 2 h. The reaction mixture was diluted with saturated aqueous NaHCO$_3$ (10 mL) and 1 M aqueous NaOH (0.5 mL) and extracted with DCM. The combined organic layers were dried (Na$_2$SO$_4$) and concentrated in vacuo, using n-heptane to azeotrope off residual DMF. The resulting residue was purified by flash chromatography (silica gel, 12 g, 0% to 10% MeOH in DCM) to give tert-butyl 2-carbamoyl-2,3-dihydro-1H-pyrrolo[2,3-b]pyridine-1-carboxylate as a white solid (100 mg), m/z=264 (M+H).

Step 3: To a solution of tert-butyl 2-carbamoyl-2,3-dihydro-1H-pyrrolo[2,3-b]pyridine-1-carboxylate (100 mg, 380 µmol, Eq: 1.00) in DCM (3 mL) was added TFA (2 mL, 26.0 mmol, Eq: 68.3) and the resulting mixture was stirred overnight. The reaction mixture was concentrated in vacuo and azeotroped with DCM (2×10 mL). The resulting residue was triturated with ether to give 2,3-dihydro-1H-pyrrolo[2,3-b]pyridine-2-carboxylic acid amide, trifluoroacetate salt as an off-white solid (95 mg)

Intermediate 3

(S)-1-((S)-2-Amino-2-cyclohexyl-acetyl)-2,3-dihydro-1H-pyrrolo[2,3-b]pyridine-2-carboxylic acid phenylamide

Intermediate 4

(R)-1-((S)-2-Amino-2-cyclohexyl-acetyl)-2,3-dihydro-1H-pyrrolo[2,3-b]pyridine-2-carboxylic acid phenylamide

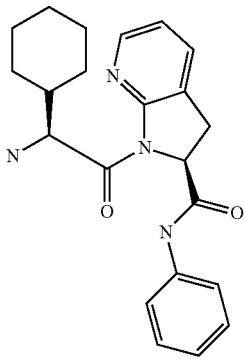

3

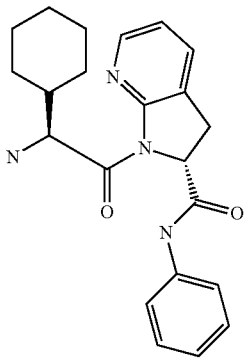

4

Step 1: In a 100 mL round-bottomed flask, (S)-2-(tert-butoxycarbonylamino)-2-cyclohexylacetic acid (2.6 g, 10.1 mmol, Eq: 3.6) was combined with DCM (31 mL) to give a colorless solution. The solution was cooled in an ice-bath and triethylamine (2.27 mL, 16.3 mmol, Eq: 5.8) and bis(2-methoxyethyl) aminosulfur trifluoride (2.23 g, 1.86 mL, 10.1 mmol, Eq: 3.6) were added. After 10 min, methyl (R,S)-2,3-dihydro-1H-pyrrolo[2,3-b]pyridine-2-carboxylate (500 mg, 2.81 mmol, Eq: 1.00) in DCM (2 mL) was added and the reaction was allowed to warm to rt and then stirred for 4 h. The reaction mixture was diluted with DCM, and then washed with saturated aqueous $NaHCO_3$, water, and brine. The organic layer was dried over $Na_2SO_4$ and concentrated in vacuo. The crude material was purified by flash chromatography (silica gel, 24 g, 0% to 20% EtOAc in hexanes) followed by a second purification by flash chromatography (silica gel, 40 g, 0% to 2% EtOAc in DCM) to give methyl 1-((S)-2-(tert-butoxycarbonylamino)-2-cyclohexylacetyl)-2,3-dihydro-1H-pyrrolo[2,3-b]pyridine-2-carboxylate (660 mg).

Step 2: In a 50 mL round-bottomed flask, methyl 1-((S)-2-(tert-butoxycarbonylamino)-2-cyclohexylacetyl)-2,3-dihydro-1H-pyrrolo[2,3-b]pyridine-2-carboxylate (660 mg, 1.58 mmol, Eq: 1.00) was combined with THF (14.8 mL) and methanol (4.95 mL) to give a colorless solution. The solution was cooled in an ice-bath and 1 M aqueous lithium hydroxide (4.74 mL, 4.74 mmol, Eq: 3) was added. The cooling bath was removed and the reaction was stirred at rt for 1 h. 0.1 M Aqueous $KHSO_4$ (4 mL) was added and the resulting mixture was extracted with EtOAc. The combined organic layers were dried over $Na_2SO_4$ and concentrated in vacuo to give 1-((S)-2-(tert-butoxycarbonylamino)-2-cyclohexylacetyl)-2,3-dihydro-1H-pyrrolo[2,3-b]pyridine-2-carboxylic acid as a white solid (600 mg), m/z=404 (M+H).

Step 3: In a 50 mL round-bottomed flask, 1-((S)-2-(tert-butoxycarbonylamino)-2-cyclohexylacetyl)-2,3-dihydro-1H-pyrrolo[2,3-b]pyridine-2-carboxylic acid (300 mg, 744 µmol, Eq: 1.00) and HATU (339 mg, 892 µmol, Eq: 1.2) were combined with DMF (7 mL) to give a colorless solution. Triethylamine (124 µL, 892 µmol, Eq: 1.2) and aniline (83 mg, 892 µmol, Eq: 1.2) were added and the reaction was stirred at rt overnight. The reaction mixture was poured into water (10 mL) and extracted with EtOAc (2×25 mL). The combined organic layers were washed with brine, dried over $Na_2SO_4$ and concentrated in vacuo. The crude material was purified by flash chromatography (silica gel, 24 g, 5% to 25% EtOAc in hexanes) to give tert-butyl (R)-(1S)-1-cyclohexyl-2-oxo-2-(2-(phenylcarbamoyl)-2,3-dihydro-1H-pyrrolo[2,3-b]pyridin-1-yl)ethylcarbamate (eluted first, 160 mg) and tert-butyl (S)-(1S)-1-cyclohexyl-2-oxo-2-(2-(phenylcarbamoyl)-2,3-dihydro-1H-pyrrolo[2,3-b]pyridin-1-yl)ethylcarbamate (eluted second, 130 mg), m/z=479 (M+H).

For Intermediate 3: In a 100 mL round-bottomed flask, tert-butyl (S)-(1S)-1-cyclohexyl-2-oxo-2-(2-(phenylcarbamoyl)-2,3-dihydro-1H-pyrrolo[2,3-b]pyridin-1-yl)ethylcarbamate (130 mg, 272 µmol, Eq: 1.00) was combined with DCM (2.6 mL) to give a colorless solution. TFA (2.6 mL, 33.7 mmol, Eq: 124) was added and the reaction was stirred for 1 h. The crude reaction mixture was concentrated in vacuo. The residue was dissolved in DCM (20 mL), washed with saturated aqueous $NaHCO_3$ (5 mL). The organic layer was dried over $Na_2SO_4$ and concentrated in vacuo to give (S)-1-((S)-2-amino-2-cyclohexyl-acetyl)-2,3-dihydro-1H-pyrrolo[2,3-b]pyridine-2-carboxylic acid phenylamide as a colorless oil (80 mg), m/z=379 (M+H).

For Intermediate 4: In a 100 mL round-bottomed flask, tert-butyl (R)-(1S)-1-cyclohexyl-2-oxo-2-(2-(phenylcarbamoyl)-2,3-dihydro-1H-pyrrolo[2,3-b]pyridin-1-yl)ethylcarbamate (100 mg, 209 µmol, Eq: 1.00) was combined with DCM (2 mL) to give a colorless solution. TFA (2 mL, 26.0 mmol, Eq: 124) was added and the reaction was stirred for 1 h. The crude reaction mixture was concentrated in vacuo. The residue was dissolved in DCM (20 mL) and washed with saturated aqueous $NaHCO_3$ (5 mL). The organic layer was dried over $Na_2SO_4$ and concentrated in vacuo to give (R)-1-((S)-2-amino-2-cyclohexyl-acetyl)- 2,3-dihydro-1H-pyrrolo

[2,3-b]pyridine-2-carboxylic acid phenylamide as a white solid (56 mg), m/z=379 (M+H).

Intermediate 5

(S)-1-((S)-2-Amino-3-methyl-butyryl)-2,3-dihydro-1H-pyrrolo[2,3-b]pyridine-2-carboxylic acid phenylamide

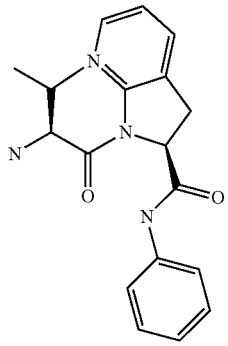

The title compound was synthesized essentially as Intermediate 3 with the following modification:

Step 1: (S)-2-(tert-butoxycarbonylamino)-3-methylbutanoic acid was used in place of (S)-2-(tert-butoxycarbonylamino)-2-cyclohexylacetic acid Intermediate 6

(S)-1-((S)-2-Amino-3-methyl-butyryl)-2,3-dihydro-1H-pyrrolo[2,3-b]pyridine-2-carboxylic acid (2,6-difluorophenyl)-amide

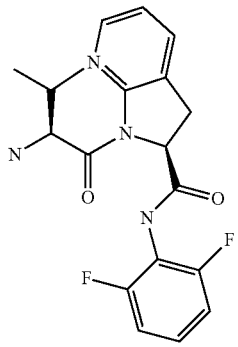

The title compound was synthesized as described for Intermediate 3 with the following modifications.

Step 1: (S)-2-(tert-butoxycarbonylamino)-3-methylbutanoic acid was used in place of (S)-2-(tert-butoxycarbonylamino)-2-cyclohexylacetic acid Step 3: To a solution of 1-((S)-2-(tert-butoxycarbonylamino)-3-methylbutanoyl)-2,3-dihydro-1H-pyrrolo[2,3-b]pyridine-2-carboxylic acid (260 mg, 715 μmol, Eq: 1.00) and diisopropylethylamine (375 μL, 2.15 mmol, Eq: 3) in DCM (7.8 mL) was added diphenylphosphinic chloride (372 mg, 300 μL, 1.57 mmol, Eq: 2.2). After stirring for 5 min, 2,6-difluoroaniline (109 μL, 1.07 mmol, Eq: 1.5) was added and the resulting solution was stirred at rt overnight. The reaction mixture was poured into 0.1 M aqueous KHSO₄ (20 mL) and the resulting mixture was extracted with EtOAc. The organic layers were concentrated in vacuo and the crude material was purified by flash chromatography (silica gel, 40 g, 0% to 30% EtOAc in hexanes) to give tert-butyl (S)-1-((S)-2-(2,6-difluorophenylcarbamoyl)-2,3-dihydro-1H-pyrrolo[2,3-b]pyridin-1-yl)-3-methyl-1-oxobutan-2-ylcarbamate (100 mg) and tert-butyl (R)-1-((S)-2-(2,6-difluorophenylcarbamoyl)-2,3-dihydro-1H-pyrrolo[2,3-b]pyridin-1-yl)-3-methyl-1-oxobutan-2-ylcarbamate white solid (80 mg), m/z=497 (M+Na).

Intermediate 7

(R,S)-1-{(S)-2-[(S)-2-(tert-Butoxycarbonyl-methyl-amino)-propionylamino]-3-methyl-butyryl}-2,3-dihydro-1H-pyrrolo[2,3-b]pyridine-2-carboxylic acid

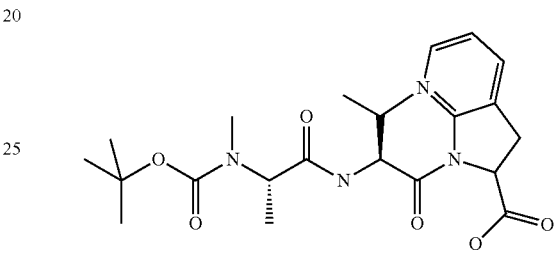

Step 1: To a solution of (S)-2-(tert-butoxycarbonylamino)-3-methylbutanoic acid (2.22 g, 10.2 mmol, Eq: 1.00) in DCM at rt was added pyridine (1.4 mL, 17.3 mmol, Eq: 1.7) followed by cyanuric fluoride (2.05 g, 1.3 mL, 15.2 mmol, Eq: 1.49). The resulting mixture was stirred at rt for 2 h. Ice (80 mL) was added and the resulting mixture was stirred rapidly for 10 min and then the mixture was filtered through a coarse frit funnel, using DCM (2×30 mL) to wash the precipitate. The filtrate was put into a separatory funnel and the organic layer separated. The organic layer was then washed with cold water (50 mL), dried briefly over Na₂SO₄, then concentrated in vacuo to a volume of ~10 mL. This solution was added to a solution of (R,S)-ethyl 2,3-dihydro-1H-pyrrolo[2,3-b]pyridine-2-carboxylate (657 mg, 3.42 mmol, Eq: 1.00) and N-methylmorpholine (2.08 g, 2.26 mL, 20.5 mmol, Eq: 6) in DCM (20 mL) and the reaction was stirred at rt overnight. The reaction mixture was diluted with EtOAc (100 mL) and washed with 1 M aqueous KHSO₄ (100 mL). The organic layer was separated and the aqueous layer was re-extracted with EtOAc (2×100 mL). The combined organic layers were washed with saturated aqueous NaHCO₃ (100 mL), 0.1 M aqueous NaOH (50 mL) and brine and concentrated in vacuo. The crude material was purified by flash chromatography (silica gel, 40 g, 0% to 30% EtOAc in hexanes). The combined fractions containing product were washed with 0.1 M NaOH (50 mL), dried over Na₂SO₄ and concentrated in vacuo to give (R,S)-ethyl 1-((S)-2-(tert-butoxycarbonylamino)-3-methylbutanoyl)-2,3-dihydro-1H-pyrrolo[2,3-b]pyridine-2-carboxylate (1.05 g), m/z=392 (M+H).

Step 2: In a 250 mL round-bottomed flask, (R,S)-ethyl 1-((S)-2-(tert-butoxycarbonylamino)-3-methylbutanoyl)-2,3-dihydro-1H-pyrrolo[2,3-b]pyridine-2-carboxylate (1 g, 2.55 mmol, Eq: 1.00) was combined with EtOH (5 mL) to give a colorless solution. HCl (2 M in dioxane, 15.3 mL, 30.7 mmol, Eq: 12) was added and the reaction was stirred at rt overnight. The reaction mixture was concentrated in vacuo and the residue co-evaporated with n-heptane to give ethyl 1-((S)-2-amino-3-methylbutanoyl)-2,3-dihydro-1H-pyrrolo[2,3-b]pyridine-2-carboxylate hydrochloride as a pale yellow solid (0.82 g), m/z=292 (M+H).

Step 3: In a 250 mL round-bottomed flask, (S)-2-(tert-butoxycarbonyl(methyl)amino)propanoic acid (610 mg, 3.00 mmol, Eq: 1.2), (R,S)-ethyl 1-((S)-2-amino-3-methylbutanoyl)-2,3-dihydro-1H-pyrrolo[2,3-b]pyridine-2-carboxylate hydrochloride (820 mg, 2.5 mmol, Eq: 1.00) and HATU (1.14 g, 3.00 mmol, Eq: 1.2) were combined with DMF (12 mL) to give a light yellow solution. Diisopropylethylamine (1.09 mL, 6.25 mmol, Eq: 2.5) was added and the reaction was stirred at rt for 1 h. The reaction mixture was diluted with EtOAc, washed with water and brine then dried over $Na_2SO_4$ and concentrated in vacuo. The crude material was purified by flash chromatography (silica gel, g, 0% to 40% EtOAc in hexanes) to give 1-((S)-2-((S)-2-(tert-butoxycarbonyl(methyl)amino)propanamido)-3-methylbutanoyl)-2,3-dihydro-1H-pyrrolo[2,3-b]pyridine-2-carboxylate as a colorless oil (0.9 g), m/z=477 (M+H).

Step 4: In a 250 mL round-bottomed flask, (R,S)-ethyl 1-((S)-2-((S)-2-(tert-butoxycarbonyl(methyl)amino)propanamido)-3-methylbutanoyl)-2,3-dihydro-1H-pyrrolo[2,3-b]pyridine-2-carboxylate (0.9 g, 1.89 mmol, Eq: 1.00) was combined with THF (17 mL) and methanol (5.67 mL) to give a light yellow solution. Aqueous lithium hydroxide (1 M, 5.7 mL, 5.7 mmol, Eq: 3) was added dropwise and the reaction was stirred at rt for 1 h. Aqueous $KHSO_4$ (0.1 M, 30 mL) was added and the resulting mixture was extracted with DCM (50 mL×2). The combined organic layers were dried over $Na_2SO_4$ and concentrated in vacuo to give (R,S)-1-((S)-2-((S)-2-(tert-butoxycarbonyl(methyl)amino)propanamido)-3-methylbutanoyl)-2,3-dihydro-1H-pyrrolo[2,3-b]pyridine-2-carboxylic acid (0.82 g), m/z=449 (M+H).

Intermediate 8

(S)-1-{(S)-2-[(S)-2-(tert-Butoxycarbonyl-methyl-amino)-propionylamino]-3-methyl-butyryl}-2,3-dihydro-1H-pyrrolo[2,3-b]pyridine-2-carboxylic acid

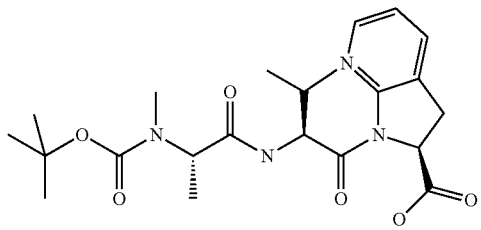

Step 1: To a solution of (S)-2-(tert-butoxycarbonylamino)-3-methylbutanoic acid (6.3 g, 29.0 mmol, Eq: 1.00) in DCM at rt was added pyridine (4.01 g, 4.1 mL, 50.7 mmol, Eq: 1.75) followed by cyanuric fluoride (5.98 g, 3.8 mL, 44.3 mmol, Eq: 1.53). The resulting mixture was stirred at rt for 2 h. Ice (160 mL) was added and the resulting mixture was stirred rapidly for 15 min. The resulting mixture was filtered through a coarse frit funnel, using DCM (2×60 mL) to wash the precipitate. The combined filtrate was put into a separatory funnel and the layers were separated. The aqueous layer was extracted with DCM (1×50 mL) and then the organic layers were combined and washed with ice-cold water (2×100 mL), dried briefly over $Na_2SO_4$, and concentrated in vacuo to a volume of ~20 mL This solution was added to a solution of ethyl (R,S)-2,3-dihydro-1H-pyrrolo[2,3-b]pyridine-2-carboxylate (2.7 g, 14.0 mmol, Eq: 1.00) and N-methylmorpholine (5.7 g, 6.2 mL, 56.4 mmol, Eq: 4.01) in DCM (50 mL) and the reaction mixture was stirred at rt overnight. The reaction mixture was diluted with EtOAc (200 mL) and washed with 0.1 M aqueous $KHSO_4$. The aqueous layer was back-extracted with EtOAc (50 mL at a time) to until all product was in the EtOAc layer. The combined EtOAc layers were concentrated to ~250 mL, washed with 0.2 M aqueous NaOH and brine and concentrated in vacuo. The crude material was purified by flash chromatography (silica gel, 80 g, 0% to 30% EtOAc in hexanes). The material obtained was taken up in EtOAc/hexanes (~200 mL), washed with 0.1 M NaOH, and concentrated in vacuo to give the racemic desired product (4.48 g) as a colorless viscous oil. The diastereomers were then separated by flash chromatography (silica gel, 120 g, 0% to 20% EtOAc/toluene) to give (S)-ethyl 1-((S)-2-(tert-butoxycarbonylamino)-3-methylbutanoyl)-2,3-dihydro-1H-pyrrolo[2,3-b]pyridine-2-carboxylate (1.9 g) and (R)-ethyl 1-((S)-2-(tert-butoxycarbonylamino)-3-methylbutanoyl)-2,3-dihydro-1H-pyrrolo[2,3-b]pyridine-2-carboxylate (2.1 g), m/z=392 (M+H).

Step 2: To a solution of (S)-ethyl 1-((S)-2-(tert-butoxycarbonylamino)-3-methylbutanoyl)-2,3-dihydro-1H-pyrrolo[2,3-b]pyridine-2-carboxylate (1.9 g, 4.85 mmol, Eq: 1.00) in EtOH (10 mL) was added HCl (2 M in ether, 38.0 mL, 76.0 mmol, Eq: 15.7) and the resulting solution was stirred at rt overnight. The reaction mixture was concentrated in vacuo and azeotroped with n-heptane (1×75 mL) to give(S)-ethyl 1-((S)-2-amino-3-methylbutanoyl)-2,3-dihydro-1H-pyrrolo[2,3-b]pyridine-2-carboxylate hydrochloride as a white solid (1.6 g).

Step 3: To a solution of (S)-ethyl 1-((S)-2-amino-3-methylbutanoyl)-2,3-dihydro-1H-pyrrolo[2,3-b]pyridine-2-carboxylate hydrochloride (1.6 g, 4.88 mmol, Eq: 1.00) in DMF (20 mL) was added (S)-2-(tert-butoxycarbonyl(methyl)amino)propanoic acid (1.2 g, 5.9 mmol, Eq: 1.21) and HATU (2.2 g, 5.79 mmol, Eq: 1.19). Diisopropylethylamine (2.2 mL, 12.6 mmol, Eq: 2.58) was then added and the resulting yellow solution was stirred at rt for 1 h. The reaction mixture was diluted with EtOAc (100 mL) and hexanes (50 mL) and washed with 0.1 M aqueous $KHSO_4$, 0.1 M aqueous NaOH, and brine and concentrated in vacuo. The crude material was purified by flash chromatography (silica gel, 80 g, 0% to 20% EtOAc/DCM:hexanes 1:1) then 20% to 40% EtOAc/DCM:hexanes 1:1) after first spot has eluted) to give (S)-ethyl 1-((S)-2-((S)-2-(tert-butoxycarbonyl(methyl)amino)propanamido)-3-methylbutanoyl)-2,3-dihydro-1H-pyrrolo[2,3-b]pyridine-2-carboxylate (eluted second 1.9 g), m/z=477 (M+H).

Step 4: A solution of (S)-ethyl 1-((S)-2-((S)-2-(tert-butoxycarbonyl(methyl)amino)propanamido)-3-methylbutanoyl)-2,3-dihydro-1H-pyrrolo[2,3-b]pyridine-2-carboxylate (1.9 g, 3.99 mmol, Eq: 1.00) in THF (36 mL) and MeOH (12 mL) was cooled in an ice bath. To this solution was added a solution of lithium hydroxide monohydrate (0.5 g, 11.9 mmol, Eq: 2.99) in water (12 mL) and the cooling bath was removed. After 1 h, the reaction was quenched by adding 0.1 M aqueous $KHSO_4$ (200 mL) and the mixture was extracted with DCM (2×100 mL). The combined DCM layers were dried over $Na_2SO_4$ and concentrated in vacuo. The residue was azeotroped with n-heptane (1×100 mL) to give (S)-1-((S)-2-((S)-2-(tert-butoxycarbonyl(methyl)amino)propanamido)-3-methylbutanoyl)-2,3-dihydro-1H-pyrrolo[2,3-b]pyridine-2-carboxylic acid (1.8 g) as a white solid, m/z=449 (M+H).

Intermediate 9

(S)-2-[Benzyloxycarbonyl-(2-methanesulfonyl-ethyl)-amino]-propionic acid

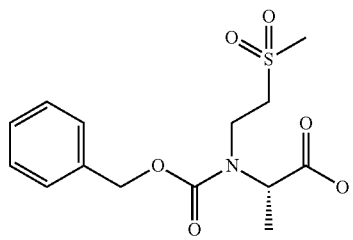 [SMILES: C[C@@H](C(=O)O)N(CCS(C)(=O)=O)C(=O)OCc1ccccc1]

Step 1: In a 50 mL round-bottomed flask, 2-(methylsulfonyl)ethanol (1.24 g, 9.99 mmol, Eq: 1.00) was combined with DCM (5 mL). To the resulting solution was added diisopropylethylamine (2.1 mL, 12.0 mmol, Eq: 1.2) and methanesulfonyl chloride (1.37 g, 931 µL, 12.0 mmol, Eq: 1.2). The ice bath was removed and the reaction was stirred at rt overnight. The crude reaction mixture was concentrated in vacuo and the residue was partitioned between EtOAc and water. The organic layer was dried over $Na_2SO_4$ and concentrated in vacuo. The crude material was purified by flash chromatography (silica gel, 80 g, 10% to 80% EtOAc in hexanes) to give 2-(methylsulfonyl)ethyl methanesulfonate (1.01 g).

Step 2: In a 100 mL round-bottomed flask, (S)-2-(benzyloxycarbonylamino)propanoic acid (331 mg, 1.48 mmol, Eq: 1.00) was combined with THF (9 mL) to give a colorless solution. Sodium hydride (131 mg, 3.26 mmol, Eq: 2.2) was added. The reaction was stirred at rt for 30 min, then 2-(methylsulfonyl)ethyl methanesulfonate (300 mg, 1.48 mmol, Eq: 1.00) was added and the reaction was stirred at rt overnight. The reaction was quenched with saturated aqueous $NH_4Cl$ and extracted with EtOAc. The combined organic layers were washed with water and brine then dried over $Na_2SO_4$ and concentrated in vacuo. The crude material was purified by flash chromatography (silica gel, 40 g, 10% to 60% EtOAc in hexanes) to give (S)-2-[benzyloxycarbonyl-(2-methanesulfonyl-ethyl)-amino]-propionic acid (201 mg).

Intermediate 10

(S)-2-[Benzyloxycarbonyl-(2-methoxy-ethyl)-amino]-propionic acid

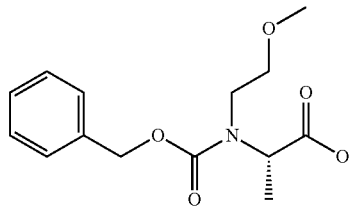 [SMILES: COCCN(C(=O)OCc1ccccc1)[C@@H](C)C(=O)O]

In a 100 mL round-bottomed flask, (S)-2-(benzyloxycarbonylamino) propanoic acid (1 g, 4.48 mmol, Eq: 1.00) was combined with DMF (9 mL) to give a colorless solution. Sodium hydride (394 mg, 9.86 mmol, Eq: 2.2) was added. After 30 min, 1-bromo-2-methoxyethane (747 mg, 505 µL, 5.38 mmol, Eq: 1.2) was added and the reaction was stirred at rt overnight. The reaction was quenched with saturated aqueous $NH_4Cl$ and extracted with EtOAc. The combined organic layers were washed with water and brine then dried over $Na_2SO_4$ and concentrated in vacuo. The crude material was purified by flash chromatography (silica gel, 40 g, 0% to 10% MeOH in DCM) to give (S)-2-[benzyloxycarbonyl-(2-methoxy-ethyl)-amino]-propionic acid (0.15 g).

Intermediate 11

3-Methyl-2,3-dihydro-pyrrolo[2,3-b]pyridine-1,2-dicarboxylic acid 1-tert-butyl ester

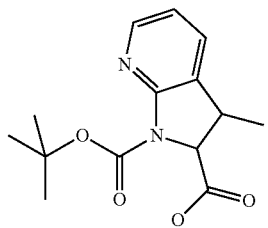 [SMILES: CC1c2cccnc2N(C(=O)OC(C)(C)C)C1C(=O)O]

Step 1: In a 50 mL round-bottomed flask, dimethylamine hydrochloride (4.91 g, 60.3 mmol, Eq: 6) was added to 37% aqueous formaldehyde (4.49 mL, 60.3 mmol, Eq: 6). Ethyl 1H-pyrrolo[2,3-b]pyridine-2-carboxylate (1.91 g, 10.0 mmol, Eq: 1.00) in ethanol (50 mL) was added followed by acetic acid (5.00 mL, 87.3 mmol, Eq: 8.7). The reaction mixture was heated to 85° C. and stirred over the weekend. The crude reaction mixture was filtered through a pad of Celite, concentrated in vacuo to ~20% of its original volume, water (100 mL) was added, and this was then washed with DCM (50 mL). The aqueous layer was cooled, basified to pH 11 through the addition of 3 M aqueous NaOH and extracted with DCM. The organic layers were dried over $Na_2SO_4$ and concentrated in vacuo to give 3-dimethylaminomethyl-1H-pyrrolo[2,3-b]pyridine-2-carboxylic acid ethyl ester as light yellow solid (1.9 g), m/z=248 (M+H).

Step 2: In a 500 mL hydrogenation jar, ethyl 3-((dimethylamino)methyl)-1H-pyrrolo[2,3-b]pyridine-2-carboxylate (0.8 g, 3.24 mmol, Eq: 1.00) and 10% palladium on carbon (344 mg, 324 µmol, Eq: 0.1) were combined with ethanol (200 mL) to give a black suspension. Perchloric acid (6 drops) was added and the mixture was shaken under a hydrogen atmosphere (50 psi) overnight. The reaction mixture was filtered through a pad of Celite and concentrated in vacuo.

The residue was partitioned between DCM (200 mL), water (100 mL) and acetic acid (0.2 mL). The organic layer was dried over $Na_2SO_4$ and concentrated in vacuo to give ethyl 3-methyl-1H-pyrrolo[2,3-b]pyridine-2-carboxylate (0.235 g), m/z=205 (M+H).

Step 3: In a 250 mL round-bottomed flask, ethyl 3-methyl-1H-pyrrolo[2,3-b]pyridine-2-carboxylate (235 mg, 1.15 mmol, Eq: 1.00) was combined with acetonitrile (10 mL) to give a grey suspension. Boc-anhydride (301 mg, 321 µL, 1.38 mmol, Eq: 1.2) and DMAP (7.03 mg, 57.5 µmol, Eq: 0.05) were added. After stirring at rt over the weekend, additional Boc-anhydride (301 mg, 321 µL, 1.38 mmol, Eq: 1.2) and DMAP (7.03 mg, 57.5 µmol, Eq: 0.05) were added and the reaction was heated at 70° C. overnight. The crude reaction mixture was concentrated in vacuo and the crude material was purified by flash chromatography (silica gel, 40 g, 0% to 15% EtOAc in hexanes) to give 1-tert-butyl 2-ethyl 3-methyl-1H-pyrrolo[2,3-b]pyridine-1,2-dicarboxylate (235 mg), m/z=305 (M+H).

Step 4: In a 100 mL round-bottomed flask, 1-tert-butyl 2-ethyl 3-methyl-1H-pyrrolo[2,3-b]pyridine-1,2-dicarboxylate (235 mg, 772 µmol, Eq: 1.00) was combined with EtOH (34 mL) to give a colorless solution. 10% Palladium on carbon (82.2 mg, 77.2 µmol, Eq: 0.1) was added and the reaction was stirred under a hydrogen atmosphere (balloon) at rt overnight. The reaction mixture was filtered through Celite and concentrated in vacuo to give 1-tert-butyl 2-ethyl 3-methyl-2,3-dihydro-1H-pyrrolo[2,3-b]pyridine-1,2-dicarboxylate (235 mg), m/z=307 (M+H).

Step 5: In a 100 mL round-bottomed flask, 1-tert-butyl 2-ethyl 3-methyl-2,3-dihydro-1H-pyrrolo[2,3-b]pyridine-1,2-dicarboxylate (235 mg, 767 µmol, Eq: 1.00) was combined with THF (7.0 mL) and ethanol (2.3 mL) to give a colorless suspension. 1 M aqueous LiOH (2.3 mL, 2.3 mmol, Eq: 3) was added and the reaction was stirred at rt for 7 d. 0.1 M Aqueous KHSO$_4$ was added and the resulting mixture was extracted with DCM (50 mL×3). The combined organic layers were dried over Na$_2$SO$_4$ and concentrated in vacuo to give 3-methyl-2,3-dihydro-pyrrolo[2,3-b]pyridine-1,2-dicarboxylic acid 1-tert-butyl ester (103 mg), m/z=277.

Intermediate 12

3,3-Dimethyl-2,3-dihydro-1H-pyrrolo[2,3-b]pyridine

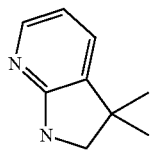

To a solution of 3,3-dimethyl-1H-pyrrolo[2,3-b]pyridin-2(3H)-one (prepared according to B. Atkinson et al. WO201192293) (153 mg, 943 µmol, Eq: 1.00) in THF (5 mL) at rt was added lithium aluminum hydride, (2 M in THF, 0.95 mL, 1.9 mmol, Eq: 2.01) and the resulting mixture was stirred at rt for 1 h. Additional lithium aluminum hydride, (2 M in THF, 0.95 mL, 1.9 mmol, Eq: 2.01) was added and stirring was continued at rt for 1 h. The reaction mixture was quenched by adding EtOAc (~2 mL) followed by water (~1 mL). To the resulting slurry was added aqueous Rochelle's salt solution (20 mL) and the mixture was extracted with EtOAc (2×20 mL). The crude material was purified by flash chromatography (silica gel, 12 g, 0% to 100% EtOAc in hexanes) to give 3,3-dimethyl-2,3-dihydro-1H-pyrrolo[2,3-b]pyridine (73 mg), m/z=149 (M+H).

Example 1

(R,S)-1-[(S)-3-Methyl-2-((S)-2-methylamino-propionylamino)-butyryl]-2,3-dihydro-1H-pyrrolo[2,3-b]pyridine-2-carboxylic acid ethylamide

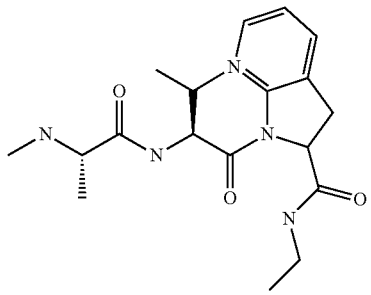

Step 1: To a solution of (R,S)-2,3-dihydro-1H-pyrrolo[2,3-b]pyridine-2-carboxylic acid ethylamide (Intermediate 1) (32 mg, 167 µmol, Eq: 1.00) in DCM (5 mL) was added (S)-(9H-fluoren-9-yl)methyl 1-chloro-3-methyl-1-oxobutan-2-ylcarbamate (71.9 mg, 201 µmol, Eq: 1.2) followed by pyridine (26.4 mg, 27 µL, 334 µmol, Eq: 1.99) and the reaction mixture was stirred at rt. After 1 h additional (S)-(9H-fluoren-9-yl)methyl 1-chloro-3-methyl-1-oxobutan-2-ylcarbamate (35 mg, 97.8 µmol, Eq: 0.585) and pyridine (26.5 mg, 27 µL, 335 µmol, Eq: 2.00) were added and stirring was continued for 2 h. Saturated aqueous NH$_4$Cl (20 mL) was added and the product was extracted into EtOAc (3×20 mL). The combined organic layers were concentrated in vacuo and the crude material was purified by flash chromatography (silica gel, 12 g, 0% to 100% EtOAc in hexanes) to give (9H-fluoren-9-yl)methyl (2S)-1-(2-(ethylcarbamoyl)-2,3-dihydro-1H-pyrrolo[2,3-b]pyridin-1-yl)-3-methyl-1-oxobutan-2-ylcarbamate (93 mg), m/z=513 (M+H).

Step 2: To a solution of (9H-fluoren-9-yl)methyl (2S)-1-(2-(ethylcarbamoyl)-2,3-dihydro-1H-pyrrolo[2,3-b]pyridin-1-yl)-3-methyl-1-oxobutan-2-ylcarbamate (85 mg, 166 µmol, Eq: 1.00) in acetonitrile (4 mL) was added piperidine (0.1 mL, 1.01 mmol, Eq: 6.09) and the resulting solution was stirred at rt for 1 h. The reaction mixture was concentrated in vacuo and the residue was treated with saturated aqueous NaHCO$_3$. The aqueous layer was extracted with DCM/EtOAc (~1:10) and the combined organic layers were concentrated in vacuo. The crude material was purified by flash chromatography (silica gel, 12 g, 0% to 10% MeOH in DCM) to give 1-((S)-2-amino-3-methylbutanoyl)-N-ethyl-2,3-dihydro-1H-pyrrolo[2,3-b]pyridine-2-carboxamide (39 mg), m/z=291 (M+H).

Step 3: To a solution of (S)-2-(tert-butoxycarbonyl(methyl)amino)propanoic acid (40.9 mg, 201 µmol, Eq: 1.5) and 1-((S)-2-amino-3-methylbutanoyl)-N-ethyl-2,3-dihydro-1H-pyrrolo[2,3-b]pyridine-2-carboxamide (39 mg, 134 µmol, Eq: 1.00) in DMF (1 mL) was added HATU (76.6 mg, 201 µmol, Eq: 1.5) followed by triethylamine (30 µL, 215 µmol, Eq: 1.6) and the resulting solution was stirred at rt for 2 h. The reaction was poured into saturated aqueous NaHCO$_3$ (10 mL) and the mixture was extracted with EtOAc (10 mL). The EtOAc layer was concentrated in vacuo and the crude material was purified by flash chromatography (silica gel, 12 g, 0% to 100% EtOAc in hexanes) to give tert-butyl (2S)-1-((2S)-1-(2-(ethylcarbamoyl)-2,3-dihydro-1H-pyrrolo[2,3-b]pyridin-1-yl)-3-methyl-1-oxobutan-2-ylamino)-1-oxopropan-2-yl(methyl)carbamate (50 mg), m/z=476 (M+H).

Step 4: To a solution of tert-butyl (2S)-1-((2S)-1-(2-(ethylcarbamoyl)-2,3-dihydro-1H-pyrrolo[2,3-b]pyridin-1-yl)-3-methyl-1-oxobutan-2-ylamino)-1-oxopropan-2-yl(methyl)carbamate (50 mg, 105 µmol, Eq: 1.00) in DCM (1 mL) was added TFA (0.5 mL, 6.49 mmol, Eq: 61.7) and the resulting mixture was stirred at rt for 2 h. The reaction mixture was concentrated in vacuo and the residue was treated with saturated aqueous NaHCO$_3$ (5 mL). The resulting aqueous layer was extracted with DCM (3×5 mL) and the combined organic layers were dried over MgSO$_4$ and then concentrated in vacuo. Treatment of the resulting residue with ethyl ether and hexanes gave (S)-1-[(S)-3-methyl-2-((S)-2-methylaminopropionylamino)-butyryl]-2,3-dihydro-1H-pyrrolo[2,3-b]pyridine-2-carboxylic acid ethylamide as a white solid (33 mg), m/z=376 (M+H).

The following examples in Table 1 were prepared using the same procedures as for Example 1 with the noted reactant modifications.

TABLE 1

| EX # | | Step 1 | Step 3 | (M + H) |
|---|---|---|---|---|
| 2 | | 3,3-Dimethyl-2,3-dihydro-1H-indole (Intermediate 12) | | 333 |
| 3 | | 3,3-Dimethyl-2,3-dihydro-1H-indole (Intermediate 12) | (S)-2-(tert-butoxy-carbonyl (ethyl)amino) propanoic acid | 347 |
| 4 | | ((S)-Chlorocarbonyl-cyclohexyl-methyl)-carbamic acid 9H-fluoren-9-ylmethyl ester | | 416 |
| 5 | | ((S)-Chlorocarbonyl-cyclohexyl-methyl)-carbamic acid 9H-fluoren-9-ylmethyl ester | (S)-2-(tert-butoxycarbonyl (ethyl)amino) propanoic acid | 430 |
| 6 | | ((1S,2S)-1-Chlorocarbonyl 2-methyl-butyl)-carbamic acid 9H-fluoren-9-ylmethyl ester | | 390 |
| 7 | | ((1S,2S)-1-Chlorocarbonyl 2-methyl-butyl)-carbamic acid 9H-fluoren-9-ylmethyl ester | (S)-2-(tert-butoxycarbonyl (ethyl)amino) propanoic acid | 404 |

TABLE 1-continued

| EX # | | Step 1 | Step 3 | (M + H) |
|---|---|---|---|---|
| 8 | | | (R,S)-2,3-Dihydro-1H-pyrrolo[2,3-b]pyridine-2-carboxylic acid amide, trifluoroacetate salt (Intermediate 2) | 348 |

Example 9

(R)-1-[(S)-3-Methyl-2-((S)-2-methylamino-propionylamino)-butyryl]-2,3-dihydro-1H-pyrrolo[2,3-b]pyridine-2-carboxylic acid (2-methoxy-phenyl)-amide

Example 10

(S)-1-[(S)-3-Methyl-2-((S)-2-methylamino-propionylamino)-butyryl]-2,3-dihydro-1H-pyrrolo[2,3-b]pyridine-2-carboxylic acid (2-methoxy-phenyl)-amide

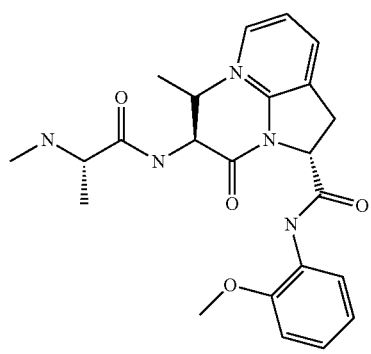

9

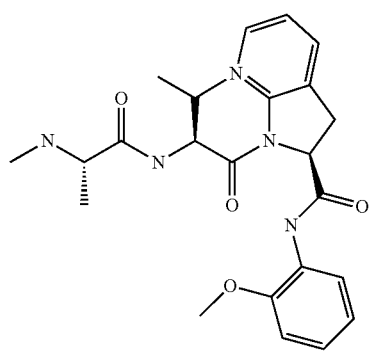

10

Step 1: To a solution of (R,S)-1-((S)-2-((S)-2-(tert-butoxycarbonyl(methyl)amino)propanamido)-3-methylbutanoyl)-2,3-dihydro-1H-pyrrolo[2,3-b]pyridine-2-carboxylic acid (Intermediate 7) (59.7 mg, 133 μmol, Eq: 1.00), o-anisidine (0.15 mL, Eq: 10), and diisopropylethylamine (35 μL, 200 μmol, Eq: 1.5) in DMF (2.00 mL) was added HATU (65.7 mg, 173 μmol, Eq: 1.3) and the resulting pale orange solution was stirred at rt overnight. The reaction mixture was diluted with saturated aqueous NaHCO$_3$ (10 mL) and 1 M aqueous NaOH (1 mL) and the resulting mixture was extracted with EtOAc (2×10 mL). The combined organic extracts were diluted with hexanes (5 mL) and washed with brine (1×5 mL) and concentrated in vacuo. The crude material was purified by flash chromatography (silica gel, 12 g, 0% to 100% EtOAc in hexanes) to give tert-butyl (R)-(2S)-1-((2S)-1-(2-(2-methoxyphenylcarbamoyl)-2,3-dihydro-1H-pyrrolo[2,3-b]pyridin-1-yl)-3-methyl-1-oxobutan-2-ylamino)-1-oxopropan-2-yl(methyl)carbamate (eluted first, 36 mg) and tert-butyl (S)-(2S)-1-((2S)-1-(2-(2-methoxyphenyl carbamoyl)-2,3-dihydro-1H-pyrrolo[2,3-b]pyridin-1-yl)-3-methyl-1-oxobutan-2-ylamino)-1-oxopropan-2-yl(methyl)carbamate (eluted second, 40 mg), m/z=554 (M+H).

For Example 10: To a solution of tert-butyl (S)-(2S)-1-((2S)-1-(2-(2-methoxyphenylcarbamoyl)-2,3-dihydro-1H-pyrrolo[2,3-b]pyridin-1-yl)-3-methyl-1-oxobutan-2-ylamino)-1-oxopropan-2-yl(methyl)carbamate (40 mg, 72.2 μmol, Eq: 1.00) in DCM (2 mL) was added TFA (1 mL, 13.0 mmol, Eq: 180) and the resulting solution was stirred at rt. After 2 h, the reaction mixture was concentrated in vacuo, the residue was treated with saturated aqueous NaHCO$_3$ (5 mL) and the resulting mixture was extracted with DCM (2×5 mL). The combined organic layers were concentrated in vacuo. The crude material was purified by flash chromatography (silica gel, 4 g, 0% to 10% MeOH in DCM) to give (S)-1-[(S)-3-methyl-2-((S)-2-methylamino-propionylamino)-butyryl]-2,3-dihydro-1H-pyrrolo[2,3-b]pyridine-2-carboxylic acid (2-methoxyphenyl)-amide (22 mg), m/z=454 (M+H).

For Example 9: To a solution of tert-butyl (R)-(2S)-1-((2S)-1-(2-(2-methoxyphenylcarbamoyl)-2,3-dihydro-1H-pyrrolo[2,3-b]pyridin-1-yl)-3-methyl-1-oxobutan-2-ylamino)-1-oxopropan-2-yl(methyl)carbamate (36 mg, 65.0 μmol, Eq: 1.00) in DCM (2 mL) was added TFA (1 mL, 13.0 mmol, Eq: 200) and the resulting solution was stirred at rt. After 2 h, the reaction mixture was concentrated in vacuo, the residue was treated with saturated aqueous NaHCO$_3$ (5 mL) and the resulting mixture was extracted with DCM (2×5 mL). The combined organic layers were concentrated in vacuo. The crude material was purified by flash chromatography (silica gel, 4 g, 0% to 10% MeOH in DCM) to give (R)-1-[(S)-3-methyl-2-((S)-2-methylamino-propionylamino)-butyryl]-2,3-dihydro-1H-pyrrolo[2,3-b]pyridine-2-carboxylic acid (2-methoxyphenyl)-amide (22 mg), m/z=454 (M+H).

The following examples in Table 2 were prepared using the same procedures as for Example 9 and Example 10 with the noted reactant modifications.

TABLE 2

| EX # | | Step 1 | m/z (M + H) |
|---|---|---|---|
| 11 | | aniline | 424 |
| 12 | | aniline | 424 |
| 13 | | 2-methylaniline | 438 |
| 14 | | 2-methylaniline | 438 |

TABLE 2-continued

| EX # | Step 1 | m/z (M + H) |
|---|---|---|
| 15 | benzylamine | 438 |
| 16 | benzylamine | 438 |
| 17 | 5-chloro-2-methyl-benzylamine | 486 |
| 18 | 2-phenylaniline | 500 |

TABLE 2-continued

| EX # | Structure | Step 1 | m/z (M + H) |
|---|---|---|---|
| 19 | | Naphthalen-1-ylamine | 474 |
| 20 | | 4-Methyl-pyridin-3-ylamine | 439 |
| 21 | | 4-fluoroaniline | 442 |
| 22 | | 4-fluoro-2-methylaniline | 456 |

TABLE 2-continued
| EX # | | Step 1 | m/z (M + H) |
|---|---|---|---|
| 23 | 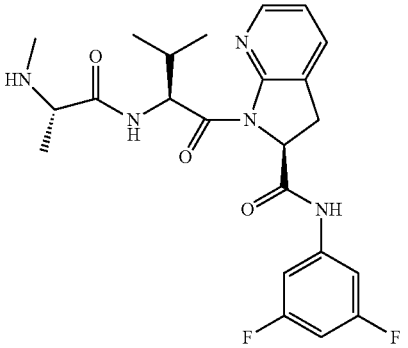 [SMILES: CN[C@@H](C)C(=O)N[C@H](C(=O)N1c2ncccc2C[C@H]1C(=O)Nc1cc(F)cc(F)c1)C(C)C] | 3,5-difluoroaniline | 460 |
| 24 | 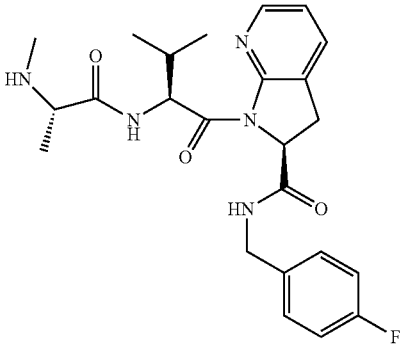 [SMILES: CN[C@@H](C)C(=O)N[C@H](C(=O)N1c2ncccc2C[C@H]1C(=O)NCc1ccc(F)cc1)C(C)C] | 4-fluorobenzyl-amine | 456 |
| 25 | 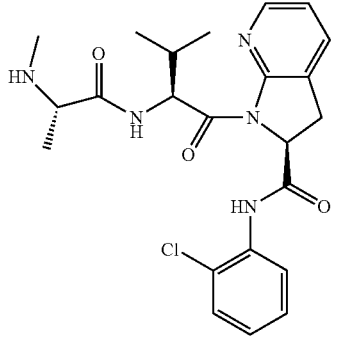 [SMILES: CN[C@@H](C)C(=O)N[C@H](C(=O)N1c2ncccc2C[C@H]1C(=O)Nc1ccccc1Cl)C(C)C] | 2-chloroaniline | 458 |

Example 26

(S)-1-[(S)-3-Methyl-2-((S)-2-methylamino-propionylamino)-butyryl]-2,3-dihydro-1H-pyrrolo[2,3-b]pyridine-2-carboxylic acid (2-benzoyl-phenyl)-amide

Example 27

(R)-1-[(S)-3-Methyl-2-((S)-2-methylamino-propionylamino)-butyryl]-2,3-dihydro-1H-pyrrolo[2,3-b]pyridine-2-carboxylic acid (2-benzoyl-phenyl)-amide

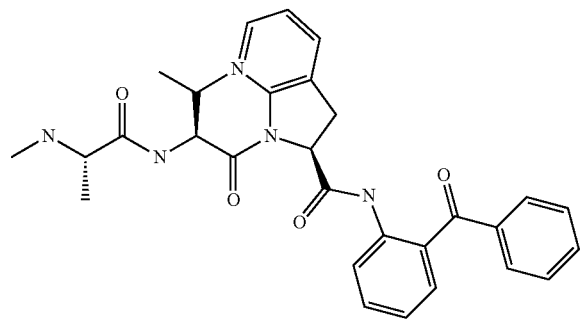

26

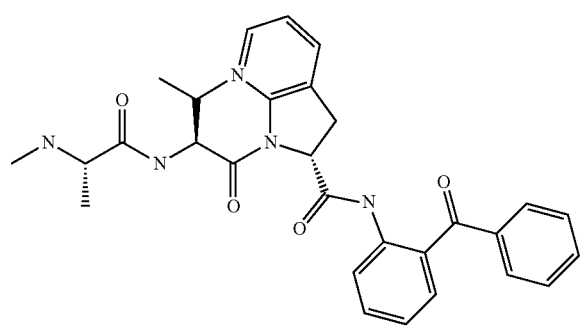

27

Step 1: To a solution of (R,S)-1-((S)-2-((S)-2-(tert-butoxycarbonyl(methyl)amino)propanamido)-3-methylbutanoyl)-2,3-dihydro-1H-pyrrolo[2,3-b]pyridine-2-carboxylic acid (Intermediate 7) (80 mg, 178 µmol, Eq: 1.00) and diisopropylethylamine (95 µL, 544 µmol, Eq: 3.05) in DCM (2.4 mL) was added diphenylphosphinic chloride (93.2 mg, 75 µL, 394 µmol, Eq: 2.21). After stirring for 5 min, (2-aminophenyl)(phenyl)methanone (53 mg, 269 µmol, Eq: 1.51) was added and the resulting solution was stirred at rt over the weekend. The reaction mixture was loaded directly onto a silica column and the crude material was purified by flash chromatography (silica gel, 4 g, 0% to 100% EtOAc in hexanes) to give tert-butyl (R)-(2S)-1-((2S)-1-(2-(2-benzoylphenylcarbamoyl)-2,3-dihydro-1H-pyrrolo[2,3-b]pyridin-1-yl)-3-methyl-1-oxobutan-2-ylamino)-1-oxopropan-2-yl(methyl)carbamate (eluted first, 32 mg) and tert-butyl (S)-(2S)-1-((2S)-1-(2-(2-benzoylphenyl-carbamoyl)-2,3-dihydro-1H-pyrrolo[2,3-b]pyridin-1-yl)-3-methyl-1-oxobutan-2-ylamino)-1-oxopropan-2-yl(methyl)carbamate (eluted second, 27 mg), m/z=628 (M+H).

Example 26

TFA (0.5 mL, 6.49 mmol, Eq: 145) was added to a solution of tert-butyl (S)-(2S)-1-((2S)-1-(2-(2-benzoylphenylcarbamoyl)-2,3-dihydro-1H-pyrrolo[2,3-b]pyridin-1-yl)-3-methyl-1-oxobutan-2-ylamino)-1-oxopropan-2-yl(methyl)carbamate (28 mg, 44.6 µmol, Eq: 1.00) in DCM (0.5 mL) and the resulting solution was stirred at rt for 2 h. The reaction mixture was concentrated in vacuo and the residue treated with saturated aqueous NaHCO$_3$ (10 mL). The resulting mixture was extracted with EtOAc (1×10 mL) and the organic layer was concentrated in vacuo. The crude residue was treated with MeOH/DCM/ether to give (S)-1-[(S)-3-methyl-2-((S)-2-methylamino-propionylamino)-butyryl]-2,3-dihydro-1H-pyrrolo[2,3-b]pyridine-2-carboxylic acid (2-benzoyl-phenyl)-amide as an off-white solid (21 mg), m/z=528 (M+H).

Example 27

TFA (0.5 mL, 6.49 mmol, Eq: 127) was added to a solution of tert-butyl (R)-(2S)-1-((2S)-1-(2-(2-benzoylphenylcarbamoyl)-2,3-dihydro-1H-pyrrolo[2,3-b]pyridin-1-yl)-3-methyl-1-oxobutan-2-ylamino)-1-oxopropan-2-yl(methyl)carbamate (32 mg, 51.0 µmol, Eq: 1.00) in DCM (0.5 mL) and the resulting solution was stirred at rt for 2 h. The reaction mixture was concentrated in vacuo and the residue treated with saturated aqueous NaHCO$_3$ (10 mL). The resulting mixture was extracted with EtOAc (1×10 mL) and the organic layer was concentrated in vacuo. The crude residue was treated with MeOH/DCM/ether to give (R)-1-[(S)-3-methyl-2-((S)-2-methylamino-propionylamino)-butyryl]-2,3-dihydro-1H-pyrrolo[2,3-b]pyridine-2-carboxylic acid (2-benzoyl-phenyl)-amide as an off-white solid (24 mg), m/z=528 (M+H).

The following examples in Table 3 were prepared using the same procedures as for Example 26 and Example 27 with the noted reactant modifications.

TABLE 3

| EX # | | Step 1 | m/z (M + H) |
|---|---|---|---|
| 28 | | 2,6-difluoro-aniline | 460 |
| 29 | | 2,6-difluoro-aniline | 460 |

TABLE 3-continued

| EX # | | Step 1 | m/z (M+H) |
|---|---|---|---|
| 30 | | 2-phenoxy-phenyl-amine | 516 |
| 31 | | 2-phenoxy-phenyl-amine | 516 |
| 32 | | 2-fluoro-6-methyl-aniline | 456 |
| 33 | | 2,6-dimethyl-aniline | 452 |

Example 34

(S)—N—{(S)-1-[(S)-2-(1H-Benzoimidazol-2-yl)-2,3-dihydro-pyrrolo[2,3-b]pyridine-1-carbonyl]-2-methyl-propyl}-2-methylamino-propionamide

Example 35

(R)—N—{(S)-1-[(S)-2-(1H-Benzoimidazol-2-yl)-2,3-dihydro-pyrrolo[2,3-b]pyridine-1-carbonyl]-2-methyl-propyl}-2-methylamino-propionamide

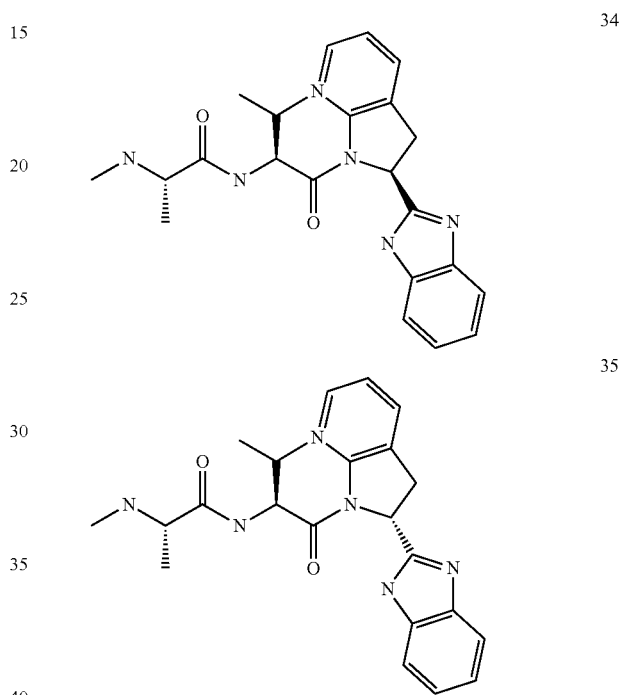

Step 1: To a solution of (R,S)-1-((S)-2-((S)-2-(tert-butoxycarbonyl(methyl)amino)propanamido)-3-methylbutanoyl)-2,3-dihydro-1H-pyrrolo[2,3-b]pyridine-2-carboxylic acid (Intermediate 7) (100 mg, 223 μmol, Eq: 1.00) and diisopropylethylamine (80 μL, 458 μmol, Eq: 2.05) in DMF (3.5 mL) was added HATU (102 mg, 268 μmol, Eq: 1.2) followed by benzene-1,2-diamine (29 mg, 268 μmol, Eq: 1.2) and the resulting mixture was stirred at rt overnight. The reaction mixture was diluted with saturated aqueous NaHCO$_3$ (15 mL) and the resulting mixture was extracted with EtOAc (2×20 mL). The crude material was purified by flash chromatography (silica gel, 12 g, 0% to 100% EtOAc in hexanes).

Step 2: In a 25 mL flask, tert-butyl (R,S)-(2S)-1-((2S)-1-(2-(2-aminophenylcarbamoyl)-2,3-dihydro-1H-pyrrolo[2,3-b]pyridin-1-yl)-3-methyl-1-oxobutan-2-ylamino)-1-oxopropan-2-yl(methyl)carbamate (0.155 g, 230 μmol, Eq: 1.00) was combined with acetic acid (2 mL) and the resulting solution was heated at 90° C. for 1 h. The reaction mixture was concentrated in vacuo and the residue was treated with saturated aqueous NaHCO$_3$ (10 mL). The resulting mixture was extracted with EtOAc (2×10 mL). A quick column was run (silica gel, 12 g, 0% to 10% MeOH in DCM) to remove lower running spots to give tert-butyl (R,S)-(2S)-1-((2S)-1-(2-(1H-benzo[d]imidazol-2-yl)-2,3-dihydro-1H-pyrrolo[2,3-b]pyridin-1-yl)-3-methyl-1-oxobutan-2-ylamino)-1-oxopropan-2-yl(methyl)carbamate (95 mg), m/z=521 (M+H).

Step 3: TFA (1 mL, 13.0 mmol, Eq: 75.1) was added to a solution of tert-butyl (R,S)-(2S)-1-((2S)-1-(2-(1H-benzo[d]imidazol-2-yl)-2,3-dihydro-1H-pyrrolo[2,3-b]pyridin-1-yl)-3-methyl-1-oxobutan-2-ylamino)-1-oxopropan-2-yl(methyl)carbamate (90 mg, 173 µmol, Eq: 1.00) in DCM (1 mL) and the resulting solution was stirred for 2 h. The reaction mixture was concentrated in vacuo and saturated aqueous NaHCO₃ (10 mL) was added to the residue. The products were extracted into DCM, the combined organic layers were concentrated in vacuo and the crude material was purified by flash chromatography (silica gel, 4 g, 0% to 10% MeOH in DCM). The isolated materials were treated with MeOH/DCM/ether to give (R)—N—{(S)-1-[(S)-2-(1H-Benzoimidazol-2-yl)-2,3-dihydro-pyrrolo[2,3-b]pyridine-1-carbonyl]-2-methyl-propyl}-2-methylamino-propionamide (eluted first, 33 mg) and (S)—N—{(S)-1-[(S)-2-(1H-Benzoimidazol-2-yl)-2,3-dihydro-pyrrolo[2,3-b]pyridine-1-carbonyl]-2-methyl-propyl}-2-methylamino-propionamide (eluted second, 34 mg) as off-white solids, m/z=421 (M+H).

Example 36

(S)-1-[(S)-3-Methyl-2-((S)-2-methylamino-propionylamino)-butyryl]-2,3-dihydro-1H-pyrrolo[2,3-b]pyridine-2-carboxylic acid (2-fluoro-phenyl)-amide

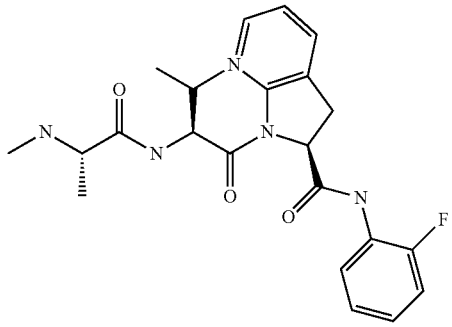

Step 1: In a 50 mL round-bottomed flask, (S)-1-((S)-2-((S)-2-(tert-butoxycarbonyl(methyl)amino)propanamido)-3-methylbutanoyl)-2,3-dihydro-1H-pyrrolo[2,3-b]pyridine-2-carboxylic acid (Intermediate 8) (50 mg, 111 µmol, Eq: 1.00) and HATU (50.9 mg, 134 µmol, Eq: 1.2) were combined in DMF to give a colorless solution. Diisopropylethylamine (23.4 µL, 134 µmol, Eq: 1.2) and 2-fluoroaniline (14.9 mg, 134 µmol, Eq: 1.2) were added. The reaction was stirred at rt for 1 h and then partitioned between ethyl acetate and water. The organic layer was washed with brine, dried over Na₂SO₄ and concentrated in vacuo. The crude material was purified by flash chromatography (silica gel, 12 g, 10% to 40% EtOAc in hexanes) to give tert-butyl (S)-1-((S)-1-((S)-2-(2-fluorophenylcarbamoyl)-2,3-dihydro-1H-pyrrolo[2,3-b]pyridin-1-yl)-3-methyl-1-oxobutan-2-ylamino)-1-oxopropan-2-yl(methyl)carbamate as a colorless oil (39 mg), m/z=542 (M+H).

Step 2: In a 50 mL round-bottomed flask, tert-butyl (S)-1-((S)-1-((S)-2-(2-fluorophenylcarbamoyl)-2,3-dihydro-1H-pyrrolo[2,3-b]pyridin-1-yl)-3-methyl-1-oxobutan-2-ylamino)-1-oxopropan-2-yl(methyl)carbamate (39 mg, 72.0 µmol, Eq: 1.00) was combined with DCM (3.00 mL) to give a colorless solution. TFA (1.00 mL, 13.0 mmol, Eq: 180) was added the reaction was stirred at rt for 30 min and then concentrated in vacuo. The residue was taken up in DCM, washed with saturated aqueous NaHCO₃, dried over Na₂SO₄ and concentrated in vacuo to give (S)—N-(2-fluorophenyl)-1-((S)-3-methyl-2-((S)-2-(methylamino)propanamido)butanoyl)-2,3-dihydro-1H-pyrrolo[2,3-b]pyridine-2-carboxamide as an off-white solid (25 mg), m/z=442 (M+H).

The following examples in Table 4 were prepared using the same procedures as for Example 36 with the noted reactant modifications.

TABLE 4

| EX # | | | Step 1 | m/z (M + H) |
|---|---|---|---|---|
| 37 | | | 2,2,2-trifluoroethylamine | 430 |
| 38 | | | 4-Methylpyridin-3-ylamine | 439 |
| 39 | | | 3-fluoroaniline | 442 |

TABLE 4-continued

| EX # | | Step 1 | m/z (M + H) |
|---|---|---|---|
| 40 | 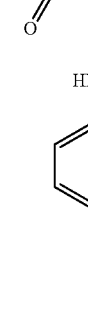 | 2-ethyl-aniline | 452 |
| 41 | 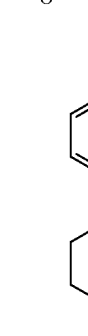 | 4-(4-Amino-phenyl)-piperidine-1-carboxylic acid tert-butyl ester | 507 |
| 42 | 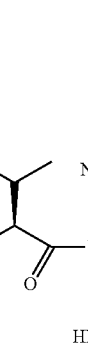 | (4-Amino-phenyl)-phenyl-methanone | 528 |

TABLE 4-continued

| EX # | | Step 1 | m/z (M + H) |
|---|---|---|---|
| 43 | 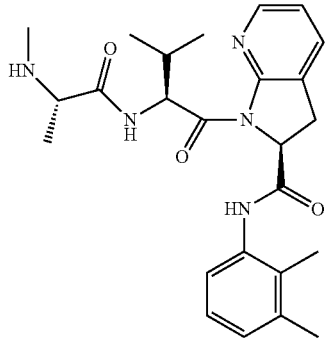 [SMILES: CN[C@@H](C)C(=O)N[C@H](C(=O)N1c2ncccc2C[C@H]1C(=O)Nc1cccc(C)c1C)C(C)C] | 2,3-dimethyl-aniline | 452 |

Example 44

(S)-1-[(S)-3-Methyl-2-((S)-2-methylamino-propionylamino)-butyryl]-2,3-dihydro-1H-pyrrolo[2,3-b]pyridine-2-carboxylic acid (2-fluoro-5-methyl-phenyl)-amide

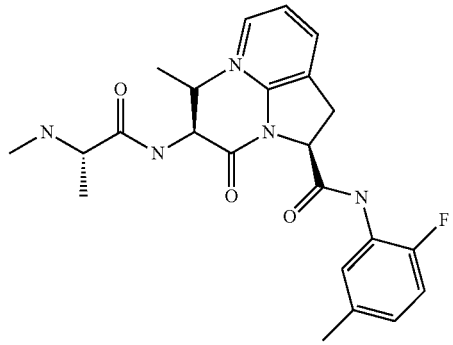

Step 1: To a solution of (S)-1-((S)-2-((S)-2-(tert-butoxycarbonyl(methyl)amino)propanamido)-3-methylbutanoyl)-2,3-dihydro-1H-pyrrolo[2,3-b]pyridine-2-carboxylic acid (Intermediate 8) (50 mg, 111 µmol, Eq: 1.00) and diisopropylethylamine (58.4 µL, 334 µmol, Eq: 3) in DCM (1.5 mL) was added diphenylphosphinic chloride (58.0 mg, 46.7 µL, 245 µmol, Eq: 2.2). After stirring for 5 min, 2-fluoro-5-methylaniline (21 mg, 167 µmol, Eq: 1.5) was added and the resulting solution was stirred at rt for 2 days. The reaction mixture was poured into 0.1 M aqueous $KHSO_4$ (20 mL) and extracted with EtOAc. The crude material was purified by flash chromatography (silica gel, 12 g, 0% to 40% EtOAc in hexanes) to give tert-butyl (S)-1-((S)-1-((S)-2-(2-fluoro-5-methylphenylcarbamoyl)-2,3-dihydro-1H-pyrrolo[2,3-b]pyridin-1-yl)-3-methyl-1-oxobutan-2-ylamino)-1-oxopropan-2-yl(methyl)carbamate as a colorless oil (49 mg), m/z=556 (M+H).

Step 2: In a 50 mL round-bottomed flask, tert-butyl (S)-1-((S)-1-((S)-2-(2-fluoro-5-methylphenylcarbamoyl)-2,3-dihydro-1H-pyrrolo[2,3-b]pyridin-1-yl)-3-methyl-1-oxobutan-2-ylamino)-1-oxopropan-2-yl(methyl)carbamate (49 mg, 88.2 µmol, Eq: 1.00) was combined with DCM (3 mL) to give a colorless solution. TFA (1.00 mL, 13.0 mmol, Eq: 147) was added. The reaction was stirred at rt for 1 h and then concentrated in vacuo. The residue taken up in DCM, washed with saturated aqueous NaHCO$_3$, dried over Na$_2$SO$_4$ and concentrated in vacuo to give (S)-1-[(S)-3-Methyl-2-((S)-2-methylamino-propionylamino)-butyryl]-2,3-dihydro-1H-pyrrolo[2,3-b]pyridine-2-carboxylic acid (2-fluoro-5-methyl-phenyl)-amide as a white foam (37 mg), m/z=456 (M+H).

The following examples in Table 5 were prepared using the same procedures as for Example 44 with the noted reactant modifications.

TABLE 5

| EX # | | | m/z (M+H) |
|---|---|---|---|
| 45 | | 3,5-dimethyl-aniline | 452 |
| 46 | | 2-fluoro-4-methyl-aniline | 456 |
| 47 | | 2-fluoro-4-methoxy-aniline | 472 |
| 48 | | 2-cyano-aniline | 449 |
| 49 | | 4-Amino-3-fluoro-benzoic acid methyl ester | 500 |
| 50 | | 2-Fluoro-4-methane-sulfonyl-phenyl-amine | 520 |
| 51 | | 2-Methane-sulfonyl-ethyl-amine | 454 |

TABLE 5-continued
| EX # | | | m/z (M + H) |
|---|---|---|---|
| 52 | 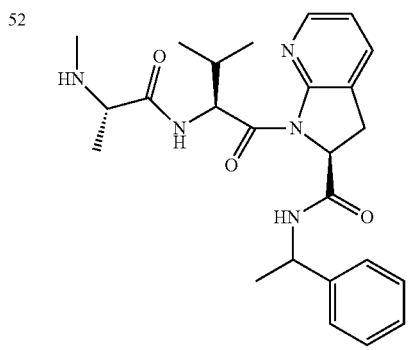 | 1-phenyl-ethyl-amine | 452 |
| 53 | 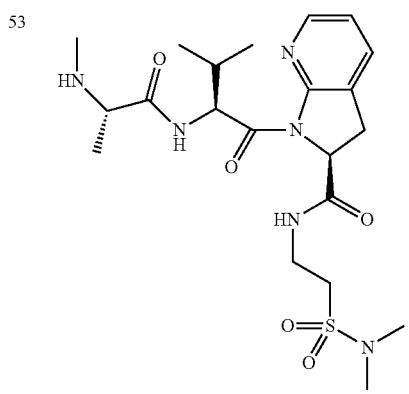 | 2-Amino-ethane-sulfonic acid dimethyl-amide | 483 |
| 54 | 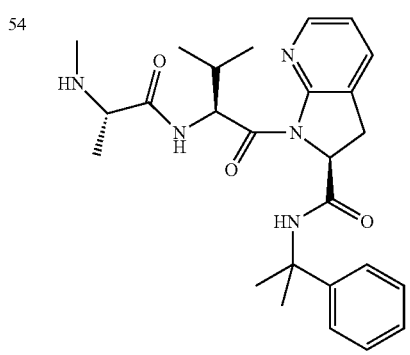 | 1-methyl-1-phenyl-ethyl-amine | 466 |
| 55 | 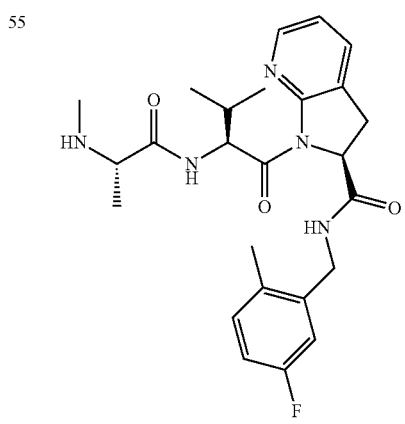 | 5-fluoro-2-methyl-benzyl-amine | 470 |
TABLE 5-continued
| EX # | | | m/z (M + H) |
|---|---|---|---|
| 56 | 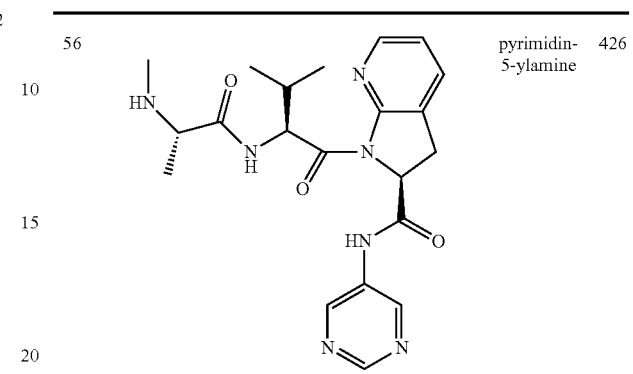 | pyrimidin-5-ylamine | 426 |
| 57 | 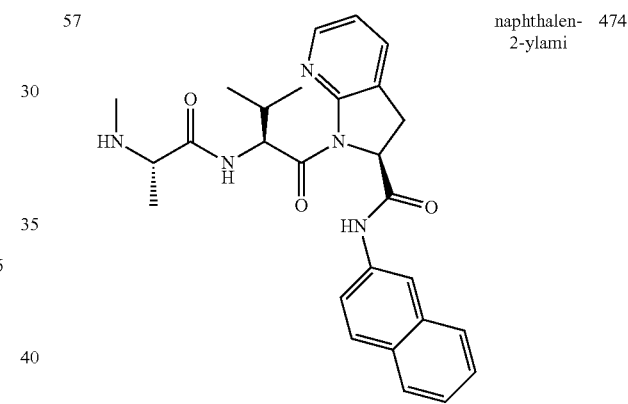 | naphthalen-2-ylami | 474 |
| 58 | 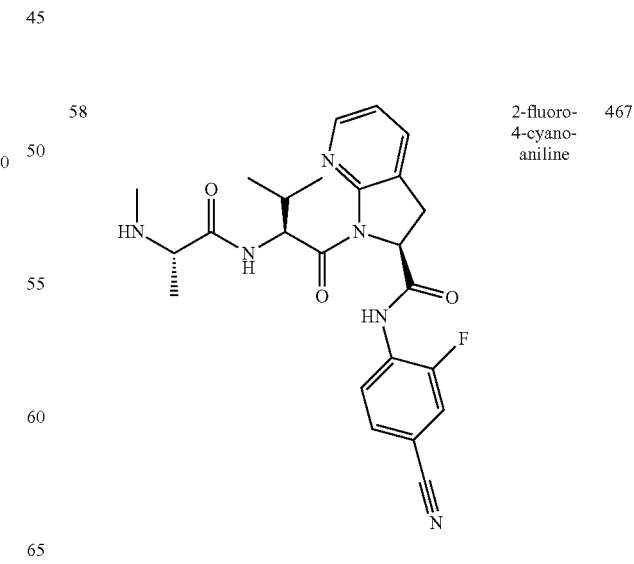 | 2-fluoro-4-cyano-aniline | 467 |

TABLE 5-continued
| EX # | | | m/z (M + H) |
|---|---|---|---|
| 59 | 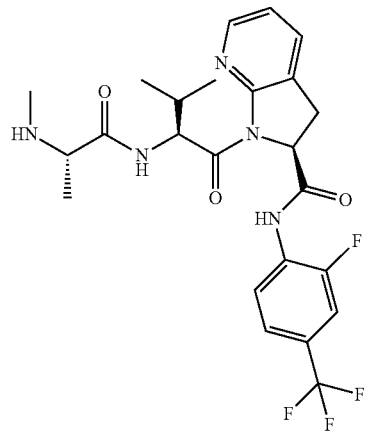 [SMILES: CN[C@@H](C)C(=O)N[C@H](C(=O)N1c2ncccc2C[C@H]1C(=O)Nc1ccc(C(F)(F)F)cc1F)C(C)C] | 2-fluoro-4-trifluoro-methyl-aniline | 510 |
| 60 | 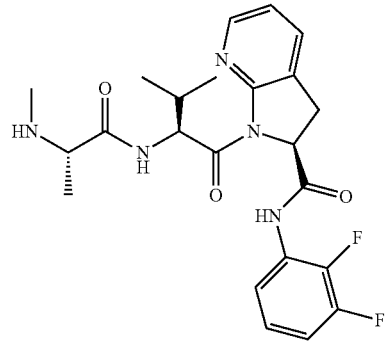 [SMILES: CN[C@@H](C)C(=O)N[C@H](C(=O)N1c2ncccc2C[C@H]1C(=O)Nc1cccc(F)c1F)C(C)C] | 2,3-difluoro-aniline | 460 |
| 61 | | 2,5-difluoro-aniline | 460 |
TABLE 5-continued
| EX # | | | m/z (M + H) |
|---|---|---|---|
| 62 | 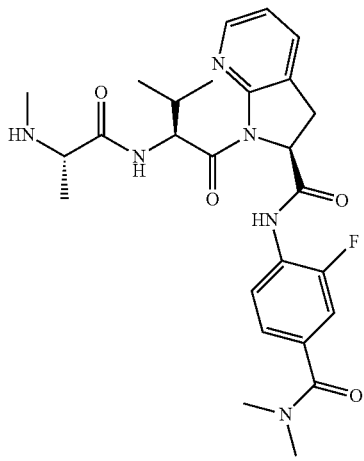 [SMILES: CN[C@@H](C)C(=O)N[C@H](C(=O)N1c2ncccc2C[C@H]1C(=O)Nc1ccc(C(=O)N(C)C)cc1F)C(C)C] | 4-amino-3-fluoro-N,N-dimethyl-benzamide | 513 |
| 63 | 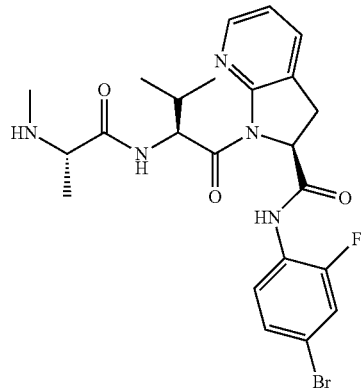 [SMILES: CN[C@@H](C)C(=O)N[C@H](C(=O)N1c2ncccc2C[C@H]1C(=O)Nc1ccc(Br)cc1F)C(C)C] | 2-fluoro-4-bromo-aniline | 520 |
| 64 | | 4-amino-3-fluoro-N-methyl-benzamide | 499 |

TABLE 5-continued

| EX # | Structure | Name | m/z (M+H) |
|---|---|---|---|
| 65 | | 2,4-difluoro-aniline | 460 |
| 66 | | 4-Methyl-thiazol-2-ylamine | 445 |
| 67 | | 5-Methyl-thiazol-2-ylamine | 445 |
| 68 | | Benzo-thiazol-2-ylamine | 481 |
| 69 | | 3-Fluoro-pyridin-4-ylamine | 443 |
| 70 | | 2-chloro-6-fluoro-aniline | 476 |
| 71 | | 2-chloro-6-methyl-aniline | 472 |
| 72 | | 2,4,6-trichloro-aniline | 526 |

Example 73

(S)—N-(2-fluoro-6-(trifluoromethyl)phenyl)-1-((S)-3-methyl-2-((S)-2-(methylamino)propanamido)butanoyl)-2,3-dihydro-1H-pyrrolo[2,3-b]pyridine-2-carboxamide

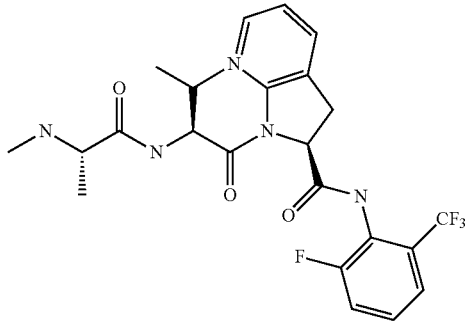

Step 1: In a 50 mL round-bottomed flask, DMF (12.2 mg, 12.9 μL, 167 μmol Eq: 1.5) was combined with DCM (1 mL) to give a colorless solution. The reaction mixture was cooled in an ice bath and oxalyl chloride (21.2 mg, 14.6 μL, 167 μmol, Eq: 1.5) was added. Pyridine (13.2 mg, 13.5 μL, 167 μmol, Eq: 1.5) was then added followed by (S)-1-((S)-2-((S)-2-(tert-butoxycarbonyl(methyl)amino)propanamido)-3-methylbutanoyl)-2,3-dihydro-1H-pyrrolo[2,3-b]pyridine-2-carboxylic acid (Intermediate 8) (50 mg, 111 μmol Eq: 1.00) and the reaction was stirred at rt for 1 h. 2-Fluoro-6-(trifluoromethyl)aniline (30.0 mg, 167 μmol, Eq: 1.5) and N-methylmorpholine (18 μL, 167 μmol, Eq: 1.5) were added and the reaction mixture was stirred at rt over the weekend. The reaction mixture was diluted with DCM and washed with water and brine. The organic layer was dried over $Na_2SO_4$ and concentrated in vacuo. The crude material was purified by flash chromatography (silica gel, 4 g, 0% to 40% EtOAc in hexanes) to give tert-butyl (S)-1-((S)-1-((S)-2-(2-fluoro-6-(trifluoromethyl)phenylcarbamoyl)-2,3-dihydro-1H-pyrrolo[2,3-b]pyridin-1-yl)-3-methyl-1-oxobutan-2-ylamino)-1-oxopropan-2-yl(methyl)carbamate as a colorless oil (20 mg).

Step 2: In a 50 mL round-bottomed flask, tert-butyl (S)-1-((S)-1-((S)-2-(2-fluoro-6-(trifluoromethyl)phenylcarbamoyl)-2,3-dihydro-1H-pyrrolo[2,3-b]pyridin-1-yl)-3-methyl-1-oxobutan-2-ylamino)-1-oxopropan-2-yl(methyl)carbamate (20 mg, 32.8 μmol Eq: 1.00) was combined with DCM (1.5 mL) to give a colorless solution. TFA (500 μL, 6.49 mmol, Eq: 198) was added and the reaction mixture was stirred at rt for 30 min. The crude reaction mixture was concentrated in vacuo. The residue was taken up in DCM, washed with saturated aqueous $NaHCO_3$, dried over $Na_2SO_4$ and concentrated in vacuo to give (S)—N-(2-fluoro-6-(trifluoromethyl)phenyl)-1-((S)-3-methyl-2-((S)-2-(methylamino)propanamido)butanoyl)-2,3-dihydro-1H-pyrrolo[2,3-b]pyridine-2-carboxamide as a white solid (10 mg), m/z=510.

The following examples in Table 6 were prepared using the same procedures as for Example 73 with the noted reactant modifications.

TABLE 6

| EX # | Step 1 | | m/z (M + H) |
|---|---|---|---|
| 74 | | 2,6-dichloroaniline | 492 |
| 75 | | 2-chloro-6-trifluoromethylaniline | 526 |

Example 76

(S)-1-[(S)-2-Cyclohexyl-2-((S)-2-ethylamino-propionylamino)-acetyl]-2,3-dihydro-1H-pyrrolo[2,3-b]pyridine-2-carboxylic acid phenylamide

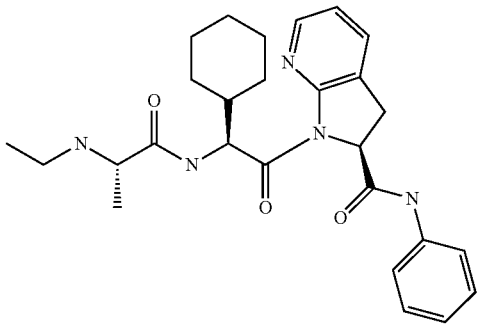 [SMILES: CCN[C@@H](C)C(=O)N[C@H](C(=O)N1c2ncccc2C[C@H]1C(=O)Nc1ccccc1)C1CCCCC1]

Step 1: In a 50 mL round-bottomed flask, 1-((S)-2-amino-2-cyclohexylacetyl)-N-phenyl-2,3-dihydro-1H-pyrrolo[2,3-b]pyridine-2-carboxamide (Intermediate 3) (26 mg, 68.7 μmol, Eq: 1.00), (S)-2-(tert-butoxycarbonyl(ethyl)amino)propanoic acid (17.9 mg, 82.4 μmol, Eq: 1.2) and HATU (31.3 mg, 82.4 μmol, Eq: 1.2) were combined with DMF (1.85 mL) to give a colorless solution. Triethylamine (12 μL, 82.4 μmol, Eq: 1.2) was added. The reaction was stirred at rt overnight and then partitioned between EtOAc and water. The organic layer was washed with brine, dried over $Na_2SO_4$ and concentrated in vacuo. The crude material was purified by flash chromatography (silica gel, 4 g, 10% to 25% EtOAc in hexanes) (33 mg).

Step 2: In a 50 mL round-bottomed flask, tert-butyl (S)-1-((S)-1-cyclohexyl-2-oxo-2-((S)-2-(phenylcarbamoyl)-2,3-dihydro-1H-pyrrolo[2,3-b]pyridin-1-yl)ethylamino)-1-oxo-propan-2-yl(ethyl)carbamate (33 mg, 57.1 µmol, Eq: 1.00) was combined with DCM (3 mL) to give a colorless solution. TFA (1 mL, 13.0 mmol, Eq: 227) was added. After 30 min, the crude reaction mixture was concentrated in vacuo. The residue was taken up in DCM, washed with saturated aqueous NaHCO$_3$, dried over Na$_2$SO$_4$ and concentrated in vacuo to give (S)-1-[(S)-2-Cyclohexyl-2-((S)-2-ethylamino-propionylamino)-acetyl]-2,3-dihydro-1H-pyrrolo[2,3-b]pyridine-2-carboxylic acid phenylamide as a white solid (23 mg), m/z=478 (M+H).

The following examples in Table 7 were prepared using the same procedures as for Example 76 with the noted reactant modifications.

TABLE 7

| EX # | | Step 1 | Step 1 | m/z (M + H) |
|---|---|---|---|---|
| 77 | 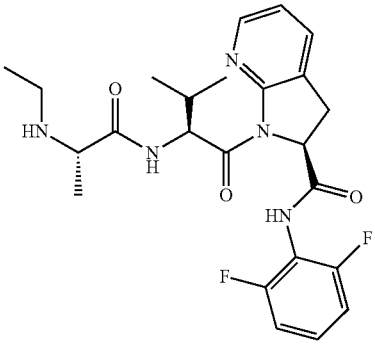 [SMILES: CCN[C@@H](C)C(=O)N[C@H](C(=O)N1c2ncccc2C[C@H]1C(=O)Nc1c(F)cccc1F)C(C)C] | intermediate 6 | (S)-2-(tert-butoxycarbonyl (ethyl)amino) propanoic acid | 474 |
| 78 | 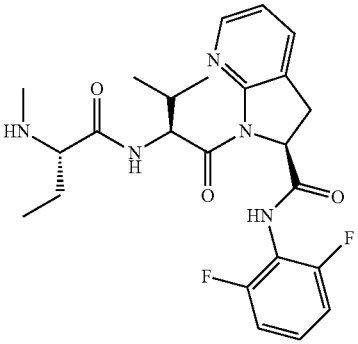 [SMILES: CC[C@H](NC)C(=O)N[C@H](C(=O)N1c2ncccc2C[C@H]1C(=O)Nc1c(F)cccc1F)C(C)C] | intermediate 6 | (S)-2-(tert-butoxycarbonyl (methyl)amino) butanoic acid | 474 |
| 79 | 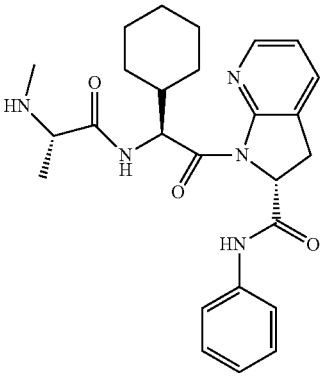 [SMILES: CN[C@@H](C)C(=O)N[C@H](C(=O)N1c2ncccc2C[C@@H]1C(=O)Nc1ccccc1)C1CCCCC1] | intermediate 4 | (S)-2-(tert-butoxycarbonyl (methyl)amino) propanoic acid | 464 |

TABLE 7-continued

| EX # | Structure | Step 1 | Step 1 | m/z (M + H) |
|---|---|---|---|---|
| 80 | | intermediate 3 | (S)-2-(tert-butoxycarbonyl (methyl)amino) propanoic acid | 464 |
| 81 | | intermediate 4 | (S)-2-(tert-butoxycarbonyl (methyl)amino) butanoic acid | 478 |
| 82 | | intermediate 3 | (S)-2-(tert-butoxycarbonyl (methyl)amino) butanoic acid | 478 |
| 83 | | intermediate 3 | (S)-2-(tert-butoxycarbonyl (d3-methyl)amino) propanoic acid | 481 |

TABLE 7-continued

| EX # | Step 1 | Step 1 | m/z (M + H) |
|---|---|---|---|
| 84 | intermediate 3 | (S)-2-(tert-butoxycarbonyl-amino)propanoic acid | 450 |
| 85 | intermediate 5 | (S)-2-(tert-butoxycarbonyl (methyl)amino) butanoic acid | 438 |
| 86 | intermediate 5 | (S)-2-(tert-butoxycarbonyl (d3-methyl)amino) propanoic acid | 441 |

TABLE 7-continued

| EX # | | Step 1 | Step 1 | m/z (M + H) |
|---|---|---|---|---|
| 87 | | intermediate 5 | (S)-2-(tert-butoxycarbonyl (ethyl)amino) propanoic acid | 438 |
| 88 | | intermediate 5 | (S)-2-(tert-butoxycarbonyl (ethyl)amino)butanoic acid | 452 |

Example 89

(S)-1-{(S)-2-[(S)-2-(2-Hydroxy-ethylamino)-propionylamino]-3-methyl-butyryl}-2,3-dihydro-1H-pyrrolo[2,3-b]pyridine-2-carboxylic acid phenylamide

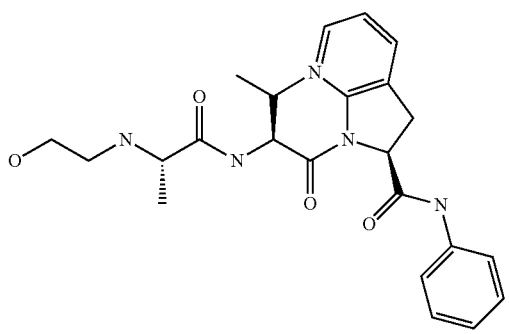

Step 1: In a 50 mL round-bottomed flask, (S)-1-((S)-2-amino-3-methylbutanoyl)-N-phenyl-2,3-dihydro-1H-pyrrolo[2,3-b]pyridine-2-carboxamide (58 mg, 171 µmol, Eq: 1.00), (S)-2-(tert-butoxycarbonylamino)propanoic acid (38.9 mg, 206 µmol, Eq: 1.2) and HATU (78.2 mg, 206 µmol, Eq: 1.2) were combined with DMF (3.98 mL) to give a colorless solution. Triethylamine (30 µL, 206 µmol, Eq: 1.2) was added. The reaction mixture was stirred at rt overnight and then partitioned between EtOAc and water. The organic layer was washed with brine, dried over Na₂SO₄ and concentrated in vacuo. The crude material was purified by flash chromatography (silica gel, 12 g, 10% to 50% EtOAc in hexanes) (75 mg).

Step 2: In a 100 mL round-bottomed flask, tert-butyl (S)-1-((S)-3-methyl-1-oxo-1-((S)-2-(phenylcarbamoyl)-2,3-dihydro-1H-pyrrolo[2,3-b]pyridin-1-yl)butan-2-ylamino)-1-oxopropan-2-ylcarbamate (75 mg, 147 µmol, Eq: 1.00) was combined with DCM (6 mL) to give a colorless solution. TFA (1.9 mL, 24.9 mmol, Eq: 169) was added. The reaction was stirred for 30 min and then concentrated in vacuo. The residue was taken up in DCM, washed with saturated aqueous NaHCO₃, dried over Na₂SO₄ and concentrated in vacuo to give (S)-1-((S)-2-((S)-2-aminopropanamido)-3-methylbutanoyl)-N-phenyl-2,3-dihydro-1H-pyrrolo[2,3-b]pyridine-2-carboxamide (55 mg) which was used without further purification.

Step 3: In a 50 mL round-bottomed flask, (S)-1-((S)-2-((S)-2-aminopropanamido)-3-methylbutanoyl)-N-phenyl-2,3-dihydro-1H-pyrrolo[2,3-b]pyridine-2-carb ox amide (55 mg, 134 µmol, Eq: 1.00) was combined with MeOH (3 mL) to give a colorless solution. 1,4-Dioxane-2,5-diol (8.87 mg, 73.9 µmol, Eq: 0.55) was added followed by acetic acid (8 µL, 134 µmol, Eq: 1.00) and sodium cyanoborohydride (13 mg, 210 µmol, Eq: 1.5). The reaction was stirred at rt for 4 h and then quenched by dropwise addition of 1 M aqueous HCl. The reaction mixture was basified with 0.1 M aqueous NaOH, extracted with EtOAc, washed with brine, dried over Na₂SO₄ and concentrated in vacuo to give (S)-1-{(S)-2-[(S)-2-(2-Hydroxy-ethylamino)-propionylamino]-3-methyl-butyryl}-2,3-dihydro-1H-pyrrolo[2,3-b]pyridine-2-carboxylic acid phenylamide as a white solid (49 mg), m/z=454.

The following examples in Table 8 were prepared using the same procedures as for Example 89 with the noted reactant modifications.

TABLE 8

| EX # | | | Step 1 | Step 1 | m/z (M + H) |
|---|---|---|---|---|---|
| 90 | 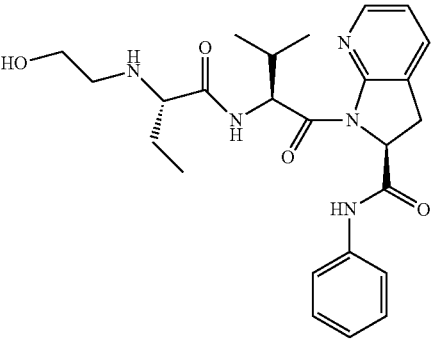 [SMILES: CC[C@H](NCCO)C(=O)N[C@H](C(=O)N1c2ncccc2C[C@H]1C(=O)Nc1ccccc1)C(C)C] | | intermediate 5 | (S)-2-(tert-butoxycarbonyl-amino) butanoic acid | 468 |
| 91 | 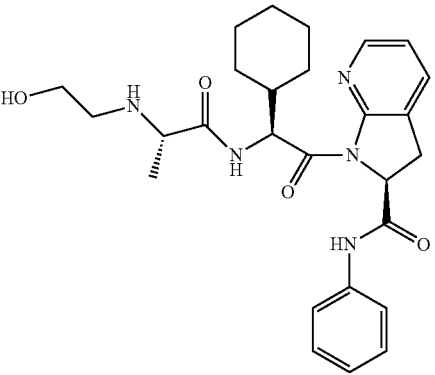 [SMILES: C[C@H](NCCO)C(=O)N[C@H](C(=O)N1c2ncccc2C[C@H]1C(=O)Nc1ccccc1)C1CCCCC1] | | intermediate 3 | (S)-2-(tert-butoxycarbonyl-amino) propanoic acid | 494 |

Example 92

(S)-1-{(S)-2-[(S)-2-(2-Methanesulfonyl-ethylamino)-propionylamino]-3-methyl-butyryl}-2,3-dihydro-1H-pyrrolo[2,3-b]pyridine-2-carb oxylic acid (2,6-difluoro-phenyl)-amide

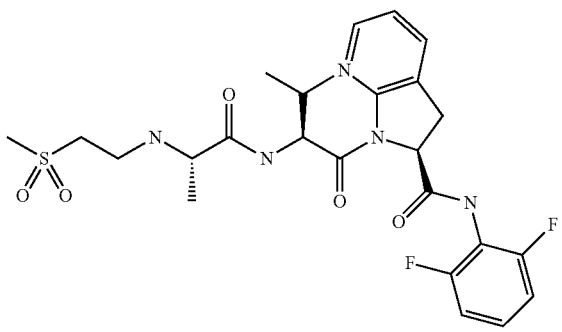

Step 1: In a 50 mL round-bottomed flask, (S)-1-((S)-2-amino-3-methylbutanoyl)-N-(2,6-difluorophenyl)-2,3-dihydro-1H-pyrrolo[2,3-b]pyridine-2-carb ox amide (Intermediate 6) (29 mg, 77.5 μmol, Eq: 1.00), (S)-2-((benzyloxycarbonyl)(2-(methylsulfonyl)ethyl)amino) propanoic acid (Intermediate 9) (30.6 mg, 93.0 μmol, Eq: 1.2), HATU (35.3 mg, 93.0 μmol, Eq: 1.2) and diisopropylethylamine (16 μL, 93.0 μmol, Eq: 1.2) were combined with DMF (2 mL) to give a colorless solution. The reaction mixture was stirred at rt overnight and then partitioned between EtOAc and water. The organic layer was washed with brine, dried over Na$_2$SO$_4$ and concentrated in vacuo. The crude material was purified by flash chromatography (silica gel, 4 g, 0% to 50% EtOAc in hexanes) to give benzyl (S)-1-((S)-1-((S)-2-(2,6-difluorophenylcarbamoyl)-2,3-dihydro-1H-pyrrolo[2,3-b]pyridin-1-yl)-3-methyl-1-oxobutan-2-ylamino)-1-oxopropan-2-yl(2-(methylsulfonyl)ethyl)carbamate (33 mg).

Step 2: In a 100 mL round-bottomed flask, benzyl (S)-1-((S)-1-((S)-2-(2,6-difluorophenylcarbamoyl)-2,3-dihydro-1H-pyrrolo[2,3-b]pyridin-1-yl)-3-methyl-1-oxobutan-2-ylamino)-1-oxopropan-2-yl(2-(methylsulfonyl)ethyl) carbamate (33 mg, 48.1 μmol, Eq: 1.00) and 10% palladium on carbon (5.12 mg, 4.81 μmol, Eq: 0.1) were combined with MeOH (5 mL) to give a black suspension which was stirred under a hydrogen atmosphere (balloon) at rt for 1 h. The reaction mixture was filtered through Celite and the filtrate was concentrated in vacuo to give (S)-1-{(S)-2-[(S)-2-(2-methanesulfonyl-ethylamino)-propionylamino]-3-methyl-butyryl}-2,3-dihydro-1H-pyrrolo[2,3-b]pyridine-2-carboxylic acid (2,6-difluoro-phenyl)-amide (18 mg), m/z=552 (M+H).

The following example in Table 9 was prepared using the same procedures as for Example 92 with the noted reactant modifications.

TABLE 9

| EX # | Step 1 | m/z (M + H) |
|---|---|---|
| 93 | intermediate 10 | 504 |

Example 94

(S)-1-[(S)-2-((S)-2-Methylamino-propionylamino)-2-(tetrahydro-pyran-4-yl)-acetyl]-2,3-dihydro-1H-pyrrolo[2,3-b]pyridine-2-carboxylic acid (2,6-difluoro-phenyl)-amide

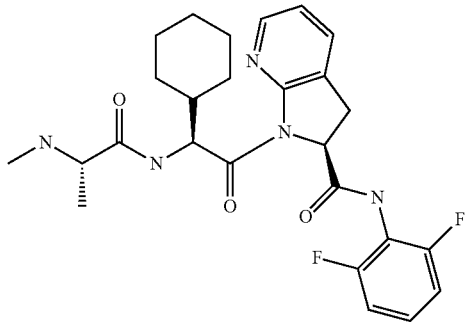 [SMILES: CN[C@@H](C)C(=O)N[C@H](C(=O)N1c2ncccc2C[C@H]1C(=O)Nc1c(F)cccc1F)C1CCCCC1]

Step 1: To a suspension of lithium 1-(tert-butoxycarbonyl)-2,3-dihydro-1H-pyrrolo[2,3-b]pyridine-2-carboxylate (589 mg, 2.18 mmol, Eq: 1.00) and 2,6-difluoroaniline (480 mg, 0.4 mL, 3.72 mmol, Eq: 1.71) in pyridine (7 mL) (ice-bath) was added dropwise phosphoryl trichloride (660 mg, 0.4 mL, 4.3 mmol, Eq: 1.97). The cooling bath was removed and the resulting yellow/orange suspension was stirred at rt for 2 h. The reaction mixture was concentrated in vacuo and the residue was treated with water (20 mL). The resulting mixture was extracted with EtOAc (2×20 mL) and the combined organic layers were washed with brine (1×5 mL). The crude material was purified by flash chromatography (silica gel, 24 g, 0% to 100% EtOAc in DCM/hexanes (1:1)). After the combined fractions were concentrated, the off-white solid was treated with 5% MeOH/ether (~10 mL) to give tert-butyl 2-(2,6-difluorophenylcarbamoyl)-2,3-dihydro-1H-pyrrolo[2,3-b]pyridine-1-carboxylate as a white solid (532 mg).

Step 2: To a solution of tert-butyl 2-(2,6-difluorophenylcarbamoyl)-2,3-dihydro-1H-pyrrolo[2,3-b]pyridine-1-carboxylate (0.2 g, 533 μmol, Eq: 1.00) in DCM (2 mL) was added TFA (2 mL, 26.0 mmol, Eq: 48.7) and the resulting solution was stirred at rt for 2 h. The reaction mixture was concentrated in vacuo and the residue was treated with saturated aqueous NaHCO₃ (10 mL). The resulting mixture was extracted with DCM (3×10 mL) and the combined organic layers were dried over Na₂SO₄ and concentrated in vacuo to give N-(2,6-difluorophenyl)-2,3-dihydro-1H-pyrrolo[2,3-b]pyridine-2-carboxamide as an off-white solid (0.15 g), m/z=276 (M+H).

Step 3: To a solution of (S)-2-(tert-butoxycarbonylamino)-2-(tetrahydro-2 h-pyran-4-yl)acetic acid (94.2 mg, 363 μmol, Eq: 2) and diisopropylethylamine (127 μL, 727 μmol, Eq: 4) in DCM (2 mL) was added N,N,N',N'-tetramethylfluoroformamidinium hexafluorophosphate (115 mg, 436 μmol, Eq: 2.4) and the resulting solution was stirred at rt for 1 h. N-(2,6-difluorophenyl)-2,3-dihydro-1H-pyrrolo[2,3-b]pyridine-2-carboxamide (50 mg, 182 μmol, Eq: 1.00) was added and the reaction was stirred at rt overnight. The reaction mixture was diluted with EtOAc (20 mL) and washed with 0.1 M aqueous KHSO₄, 0.1 M aqueous NaOH and brine and concentrated in vacuo. The crude material was purified by flash chromatography (silica gel, 12 g, 0% to 50% EtOAc in hexanes) to give tert-butyl (1R)-2-(2-(2,6-difluorophenylcarbamoyl)-2,3-dihydro-1H-pyrrolo[2,3-b]pyridin-1-yl)-2-oxo-1-(tetrahydro-2 h-pyran-4-yl)ethylcarbamate (48 mg) and tert-butyl (1S)-2-(2-(2,6-difluorophenylcarbamoyl)-2,3-dihydro-1H-pyrrolo[2,3-b]pyridin-1-yl)-2-oxo-1-(tetrahydro-2 h-pyran-4-yl)ethylcarbamate (46 mg), m/z=517 (M+H).

Step 4: To a solution of tert-butyl (1S)-2-(2-(2,6-difluorophenylcarbamoyl)-2,3-dihydro-1H-pyrrolo[2,3-b]pyridin-1-yl)-2-oxo-1-(tetrahydro-2 h-pyran-4-yl)ethylcarbamate (46 mg, 89.1 μmol, Eq: 1.00) in DCM (1 mL) was added TFA (1 mL, 13.0 mmol, Eq: 146) and the resulting solution was stirred at rt for 1 h. The reaction mixture was concentrated in vacuo. The residue was treated with saturated aqueous NaHCO₃ (5 mL) and the mixture was extracted with DCM (2×5 mL). The combined organic layers were dried over Na₂SO₄ and concentrated in vacuo to give product (37 mg) that was used directly in the next reaction.

Step 5: To a solution of 1-((S)-2-amino-2-(tetrahydropyran-4-yl)acetyl)-N-(2,6-difluorophenyl)-2,3-dihydro-1H-pyrrolo[2,3-b]pyridine-2-carboxamide (37 mg, 88.9 μmol, Eq: 1.00), (S)-2-(tert-butoxycarbonyl(methyl)amino)propanoic acid (27.1 mg, 133 μmol, Eq: 1.5) and diisopropylethylamine (62 μL, 355 μmol, Eq: 4) in DMF was added HATU (60.8 mg, 160 μmol, Eq: 1.8) and the resulting solution was stirred at rt. The reaction mixture was diluted with water (10 mL) and extracted with EtOAc (10 mL). The organic layer was then washed with 0.1 M aqueous NaOH and brine and then concentrated in vacuo. The crude material was purified by flash chromatography (silica gel, 12 g, 0% to 100% EtOAc in hexanes) to give tert-butyl (2S)-1-((1S)-2-(2-(2,6-difluorophenylcarbamoyl)-2,3-dihydro-1H-pyrrolo[2,3-b]pyridin-1-yl)-2-oxo-1-(tetrahydro-2 h-pyran-4-yl)ethylamino)-1-oxopropan-2-yl(methyl)carbamate (54 mg), m/z=602 (M+H).

Step 6: To a solution of tert-butyl (2S)-1-((1S)-2-(2-(2,6-difluorophenylcarbamoyl)-2,3-dihydro-1H-pyrrolo[2,3-b]pyridin-1-yl)-2-oxo-1-(tetrahydropyran-4-yl)ethylamino)-1-oxopropan-2-yl(methyl)carbamate (54 mg, 89.8 μmol, Eq: 1.00) in DCM (1 mL) was added TFA (1 mL, 13.0 mmol, Eq: 145) and the resulting solution was stirred at rt for 1 h. The reaction mixture was concentrated in vacuo and the residue was treated with saturated aqueous NaHCO₃ (10 mL). The resulting mixture was extracted with DCM (2×10 mL), the combined organic layers dried over Na₂SO₄, and then concentrated in vacuo. Treatment of the residue with diethyl ether/hexanes gave (S)-1-[(S)-2-((S)-2-methylamino-propionylamino)-2-(tetrahydropyran-4-yl)-acetyl]-2,3-dihydro-1H-pyrrolo[2,3-b]pyridine-2-carboxylic acid (2,6-difluorophenyl)-amide as a white solid (45 mg), m/z=502 (M+H).

Example 95

(R)-1-[(S)-2-((S)-2-Methylamino-propionylamino)-2-(tetrahydro-pyran-4-yl)-acetyl]-2,3-dihydro-1H-pyrrolo[2,3-b]pyridine-2-carboxylic acid (2,6-difluoro-phenyl)-amide

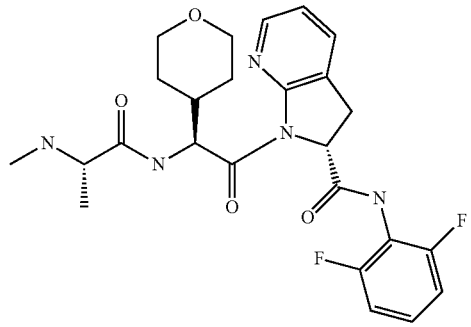 [SMILES: CN[C@@H](C)C(=O)N[C@H](C(=O)N1c2ncccc2C[C@@H]1C(=O)Nc1c(F)cccc1F)C1CCOCC1]

The same procedures as for Example 94 above were carried out with the following modifications.

Steps 4-6 were carried out using tert-butyl (1R)-2-(2-(2,6-difluorophenylcarbamoyl)-2,3-dihydro-1H-pyrrolo[2,3-b]pyridin-1-yl)-2-oxo-1-(tetrahydropyran-4-yl)ethylcarbamate (48 mg) to give (R)-1-[(S)-2-((S)-2-methylamino-propionylamino)-2-(tetrahydropyran-4-yl)-acetyl]-2,3-dihydro-1H-pyrrolo[2,3-b]pyridine-2-carboxylic acid (2,6-difluoro-phenyl)-amide (45 mg), m/z=502 (M+H).

The following examples in Table 10 were prepared using the same procedures as for Example 94 and 95 with the noted reactant modifications.

TABLE 10

| EX # | Structure | Step 1 | Step 3 | m/z (M + H) |
|------|-----------|--------|--------|-------------|
| 96 | | aniline | (S)-2-(tert-butoxycarbonylamino)-4-(methylsulfonyl)butanoic acid | 488 |
| 97 | | aniline | (S)-2-(tert-butoxycarbonylamino)-4-(methylsulfonyl)butanoic acid | 488 |
| 98 | | Intermediate 11 | (S)-2-(tert-butoxycarbonylamino)-3-methylbutanoic acid | 474 |

Example 99

(S)-1-[(S)-2-((S)-2-Methylamino-propionylamino)-2-(tetrahydro-pyran-4-yl)-acetyl]-2,3-dihydro-1H-pyrrolo[2,3-b]pyridine-2-carboxylic acid (2-fluoro-6-methyl-phenyl)-amide

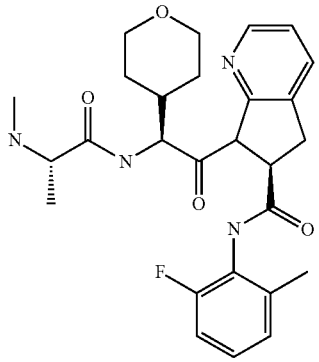 [SMILES: CN[C@@H](C)C(=O)N[C@H](C(=O)C1c2ncccc2C[C@H]1C(=O)Nc1c(C)cccc1F)C1CCOCC1]

Step 1: In a 100 mL round-bottomed flask, (S)-2-(tert-butoxycarbonylamino)-2-(tetrahydro-2H-pyran-4-yl)acetic acid (270 mg, 1.04 mmol, Eq: 1.00) was combined with DCM (10 mL) to give a colorless solution. Diisopropylethylamine (0.73 mL, 4.16 mmol, Eq: 4) was added followed by N,N,N',N'-tetramethylfluoroformamidinium hexafluorophosphate (824 mg, 3.12 mmol, Eq: 3). The reaction was stirred at rt for 1 h and then (S)-ethyl 2,3-dihydro-1H-pyrrolo[2,3-b]pyridine-2-carboxylate (200 mg, 1.04 mmol, Eq: 1.00) was added. After stirring overnight at rt, the reaction mixture was washed with saturated aqueous NaHCO₃ (50 mL), dried over Na₂SO₄ and concentrated in vacuo. The crude material was purified by flash chromatography (silica gel, 24 g, 0% to 30% EtOAc in hexanes) to give (S)-ethyl 1-((S)-2-(tert-butoxycarbonylamino)-2-(tetrahydro-2H-pyran-4-yl)acetyl)-2,3-dihydro-1H-pyrrolo[2,3-b]pyridine-2-carboxylate (220 mg), m/z=434 (M+H).

Step 2: In a 100 mL round-bottomed flask, (S)-ethyl 1-((S)-2-(tert-butoxycarbonylamino)-2-(tetrahydro-2H-pyran-4-yl)acetyl)-2,3-dihydro-1H-pyrrolo[2,3-b]pyridine-2-carboxylate (220 mg, 507 μmol, Eq: 1.00) was combined with DCM (10 mL) to give a colorless solution. TFA (5 mL, 64.9 mmol, Eq: 128) was added and the reaction was stirred at rt for 2 h. The reaction mixture was concentrated in vacuo and the residue was treated with saturated aqueous NaHCO₃ (10 mL). The resulting mixture was extracted with DCM (2×10 mL), the combined organic layers dried over Na₂SO₄, and then concentrated in vacuo to give (S)-ethyl 1-((S)-2-amino-2-(tetrahydro-2H-pyran-4-yl)acetyl)-2,3-dihydro-1H-pyrrolo[2,3-b]pyridine-2-carboxylate (140 mg), m/z=334 (M+H).

Step 3: In a 100 mL round-bottomed flask, (S)-2-(tert-butoxycarbonyl(methyl)amino)propanoic acid (128 mg, 630 μmol, Eq: 1.5), (S)-ethyl 1-((S)-2-amino-2-(tetrahydro-2H-pyran-4-yl)acetyl)-2,3-dihydro-1H-pyrrolo[2,3-b]pyridine-2-carboxylate (140 mg, 420 μmol, Eq: 1.00) and HATU (240 mg, 630 μmol, Eq: 1.5) were combined with DMF (2 mL) to give a light yellow solution. Diisopropylethylamine (110 μL, 630 μmol, Eq: 1.5) was added and the reaction was stirred at rt over the weekend. The reaction mixture was partitioned between EtOAc and water and the separated organic layer was washed with saturated aqueous NaHCO₃ and brine, dried over Na₂SO₄ and concentrated in vacuo. The crude material was purified by flash chromatography (silica gel, 12 g, 0% to 40% EtOAc in hexanes) to give (S)-ethyl 1-((S)-2-((S)-2-(tert-butoxycarbonyl(methyl)amino)propanamido)-2-(tetrahydro-2H-pyran-4-yl)acetyl)-2,3-dihydro-1H-pyrrolo[2,3-b]pyridine-2-carboxylate (188 mg), m/z=519 (M+H).

Step 4: In a 100 mL round-bottomed flask, (S)-ethyl 1-((S)-2-((S)-2-(tert-butoxycarbonyl(methyl)amino)propanamido)-2-(tetrahydro-2H-pyran-4-yl)acetyl)-2,3-dihydro-1H-pyrrolo[2,3-b]pyridine-2-carboxylate (188 mg, 363 μmol, Eq: 1.00) was combined with THF (3 mL) and ethanol (1 mL) to give a colorless solution. Aqueous 1 M LiOH (1.1 mL, 1.1 mmol, Eq: 3) was added and the reaction was stirred at rt for 1 h. Aqueous 0.1 M KHSO₄ (10 mL) was added and the resulting mixture was extracted with EtOAc. The combined organic layers were dried over Na₂SO₄ and concentrated in vacuo to give (S)-1-((S)-2-((S)-2-(tert-butoxycarbonyl(methyl)amino)propanamido)-2-(tetrahydro-2H-pyran-4-yl)acetyl)-2,3-dihydro-1H-pyrrolo[2,3-b]pyridine-2-carboxylic acid (135 mg), m/z=491 (M+H).

Step 5: To a solution of (S)-1-((S)-2-((S)-2-(tert-butoxycarbonyl(methyl)amino)propanamido)-2-(tetrahydro-2H-pyran-4-yl)acetyl)-2,3-dihydro-1H-pyrrolo[2,3-b]pyridine-2-carboxylic acid (60 mg, 122 pilot, Eq: 1.00) and diisopropylethylamine (64 μL, 367 μmol, Eq: 3) in DCM (1.8 mL) was added diphenylphosphinic chloride (63.7 mg, 51 μL, 269 μmol, Eq: 2.2). After stirring for 5 min, 2-fluoro-6-methylaniline (18.4 mg, 147 μmol, Eq: 1.2) was added and the resulting solution stirred at rt for 2 d. The reaction mixture was poured into aqueous 0.1 M KHSO₄ (20 mL) and the resulting mixture was extracted with EtOAc. The combined organic layers were concentrated in vacuo and the crude material was purified by flash chromatography (silica gel, 4 g, 10% to 50% EtOAc in hexanes) to give tert-butyl (S)-1-((S)-2-((S)-2-(2-fluoro-6-methylphenylcarbamoyl)-2,3-dihydro-1H-pyrrolo[2,3-b]pyridin-1-yl)-2-oxo-1-(tetrahydro-2H-pyran-4-yl)ethylamino)-1-oxopropan-2-yl(methyl)carbamate (30 mg), m/z=598 (M+H).

Step 6: In a 50 mL round-bottomed flask, tert-butyl (S)-1-((S)-2-((S)-2-(2-fluoro-6-methylphenylcarbamoyl)-2,3-dihydro-1H-pyrrolo[2,3-b]pyridin-1-yl)-2-oxo-1-(tetrahydro-2H-pyran-4-yl)ethylamino)-1-oxopropan-2-yl(methyl)carbamate (30 mg, 50.2 μmol, Eq: 1.00) was combined with DCM (3 mL) to give a colorless solution. TFA (1 mL, 13.0 mmol, Eq: 259) was added and the reaction was stirred at rt for 30 min. The reaction mixture was concentrated in vacuo and the residue was treated with saturated aqueous NaHCO₃ (10 mL). The resulting mixture was extracted with DCM (2×10 mL), the combined organic layers dried over Na₂SO₄, and then concentrated in vacuo to give (S)-1-[(S)-2-((S)-2-methylamino-propionylamino)-2-(tetrahydro-pyran-4-yl)-acetyl]-2,3-dihydro-1H-pyrrolo[2,3-b]pyridine-2-carboxylic acid (2-fluoro-6-methyl-phenyl)-amide (13 mg), m/z=498 (M+H).

Example 100

Biochemical Assays

TR-FRET Assay for BIR2 and BIR3

The ability of a test compound to inhibit the binding of BIR2 and/or BIR3 domains of the XIAP protein to Peptide A (a SMAC-derived peptide described below) evidences that the test compound acts as a SMAC-mimetic resulting in reactivation of a cell's apoptotic pathway.

The peptide AVPIAQKSEK-(ε-biotin)-OH 1:2 TFA ("Peptide A") was identified as a substrate for the TR-FRET assay by screening the 6× Histidine-tagged BIR2 domain and BIR3 domain of XIAP against a set of 29 peptides synthesized based on sequences reported by Sweeny et al. (*Biochemistry*, 2006, 45, 14740 14748). The peptides were labeled with the fluorescent tags FITC or TAMRA and Kd values were determined by fluorescence polarization assay. The sequence AVPIAQKSEK was identified as optimal for using in an assay. The peptide sequence was derivatized with biotin to provide AVPIAQKSEK-(ε-biotin)-OH 1:2 TFA as the substrate for the TR-FRET assay.

The XIAP protein sequence was obtained from the SWISS-PROT protein sequence database and the BIR2 and BIR3 domains were derived from that. The sequence of the BIR2 domain used for the TR-FRET assay is MRHHHHH-HRDHFALDRPSETHADYLLRTGQVVDIS-DTIYPRNPAMYSEEARLKSF QNWPDYAHLTPRELA-SAGLYYTGIGDQVQCFACGGKLKNWEPGDRAWSE-HRRHE PNCFFVLGRNLNIRSE.

The sequence of the BIR3 domain used for the TR-FRET assay is MRHHHHHHRSDAVSSDRNFPNSTNL-PRNPSMADYEARIFTEGTWIYSVNK

EQLARAGFYALGEGDKVKCFHCGGGLTD-WKPSEDPWEQHAKWYPGCKYL LEQKGQEYIN-NIHLTHSLEECLVRTT.

Ten nanomolar of 6× Histidine-tagged BIR2 domain, corresponding to amino acids 124-240 of XIAP, or BIR3 domain, corresponding to amino acids 241-356 of XIAP, was mixed with 20 nM of the peptide AVPIAQKSEK-(z-biotin)-OH 1:2 TFA, in the presence of 50 mM Tris-Cl, pH 7.5, 100 mM NaCl, 1 mM dithiothreitol (DTT) and 0.1 mg/mL bovine serum albumin (BSA). Following a 45 mM incubation at 37° C., Europium-Streptavidin and Allophycocyanin conjugated anti-Histidine antibody were added to a final concentration of 1.5 nM and 15 nM, respectively. Time-resolved fluorescence resonance energy transfer (TR-FRET) signals were measured 1 hour later at room temperature. Test compound potency was assessed at 10 serially diluted concentrations. Percentage of inhibition at each concentration was determined to generate an $IC_{50}$ value for each test compound.

These values are listed below in Table 11.

TABLE 11

| | Systematic Name | Ic50 BIR2 | Ic50 BIR3 |
|---|---|---|---|
| 1 | (R,S)-1-[(S)-3-Methyl-2-((S)-2-methylamino-propionylamino)-butyryl]-2,3-dihydro-1H-pyrrolo[2,3-b]pyridine-2-carboxylic acid ethylamide | 1.044 | >54.8 |
| 2 | (S)-N-[(S)-1-(3,3-Dimethyl-2,3-dihydro-pyrrolo[2,3-b]pyridine-1-carbonyl)-2-methyl-propyl]-2-methylamino-propionamide | 3.879 | >54.8 |
| 3 | (S)-N-[(S)-1-(3,3-Dimethyl-2,3-dihydro-pyrrolo[2,3-b]pyridine-1-carbonyl)-2-methyl-propyl]-2-methylamino-butyramide | 4.032 | >54.8 |
| 4 | (R,S)-1-[(S)-2-Cyclohexyl-2-((S)-2-methylamino-propionylamino)-acetyl]-2,3-dihydro-1H-pyrrolo[2,3-b]pyridine-2-carboxylic acid ethylamide | 2.122 | >54.8 |
| 5 | (R,S)-1-[(S)-2-Cyclohexyl-2-((S)-2-methylamino-butyrylamino)-acetyl]-2,3-dihydro-1H-pyrrolo[2,3-b]pyridine-2-carboxylic acid ethylamide | 1.856 | >54.8 |
| 6 | (R,S)-1-[(2S,3S)-3-Methyl-2-((S)-2-methylamino-propionylamino)-pentanoyl]-2,3-dihydro-1H-pyrrolo[2,3-b]pyridine-2-carboxylic acid ethylamide | 1.284 | >54.8 |
| 7 | (R,S)-1-[(2S,3S)-3-Methyl-2-((S)-2-methylamino-butyrylamino)-pentanoyl]-2,3-dihydro-1H-pyrrolo[2,3-b]pyridine-2-carboxylic acid ethylamide | 1.033 | >54.8 |

TABLE 11-continued

| | Systematic Name | Ic50 BIR2 | Ic50 BIR3 |
|---|---|---|---|
| 8 | (R,S)-1-[(S)-3-Methyl-2-((S)-2-methylamino-propionylamino)-butyryl]-2,3-dihydro-1H-pyrrolo[2,3-b]pyridine-2-carboxylic acid amide | 0.501 | >54.8 |
| 9 | (R)-1-[(S)-3-Methyl-2-((S)-2-methylamino-propionylamino)-butyryl]-2,3-dihydro-1H-pyrrolo[2,3-b]pyridine-2-carboxylic acid (2-methoxy-phenyl)-amide | 12.69 | >54.8 |
| 10 | (S)-1-[(S)-3-Methyl-2-((S)-2-methylamino-propionylamino)-butyryl]-2,3-dihydro-1H-pyrrolo[2,3-b]pyridine-2-carboxylic acid (2-methoxy-phenyl)-amide | 0.0841 | 25.9 |
| 11 | (S)-1-[(S)-3-Methyl-2-((S)-2-methylamino-propionylamino)-butyryl]-2,3-dihydro-1H-pyrrolo[2,3-b]pyridine-2-carboxylic acid phenylamide | 0.0635 | >54.8 |
| 12 | (R)-1-[(S)-3-Methyl-2-((S)-2-methylamino-propionylamino)-butyryl]-2,3-dihydro-1H-pyrrolo[2,3-b]pyridine-2-carboxylic acid phenylamide | >54.8 | >54.8 |
| 13 | (R)-1-[(S)-3-Methyl-2-((S)-2-methylamino-propionylamino)-butyryl]-2,3-dihydro-1H-pyrrolo[2,3-b]pyridine-2-carboxylic acid o-tolylamide | >54.8 | >54.8 |
| 14 | (S)-1-[(S)-3-Methyl-2-((S)-2-methylamino-propionylamino)-butyryl]-2,3-dihydro-1H-pyrrolo[2,3-b]pyridine-2-carboxylic acid o-tolylamide | 0.0335 | >54.8 |
| 15 | (R)-1-[(S)-3-Methyl-2-((S)-2-methylamino-propionylamino)-butyryl]-2,3-dihydro-1H-pyrrolo[2,3-b]pyridine-2-carboxylic acid benzylamide | 1.803 | 45.94 |
| 16 | (S)-1-[(S)-3-Methyl-2-((S)-2-methylamino-propionylamino)-butyryl]-2,3-dihydro-1H-pyrrolo[2,3-b]pyridine-2-carboxylic acid benzylamide | 0.159 | 3.949 |
| 17 | (S)-1-[(S)-3-Methyl-2-((S)-2-methylamino-propionylamino)-butyryl]-2,3-dihydro-1H-pyrrolo[2,3-b]pyridine-2-carboxylic acid 5-chloro-2-methyl-benzylamide | 0.392 | 24.25 |
| 18 | (S)-1-[(S)-3-Methyl-2-((S)-2-methylamino-propionylamino)-butyryl]-2,3-dihydro-1H-pyrrolo[2,3-b]pyridine-2-carboxylic acid biphenyl-2-ylamide | 0.108 | 37.63 |
| 19 | (S)-1-[(S)-3-Methyl-2-((S)-2-methylamino-propionylamino)-butyryl]-2,3-dihydro-1H-pyrrolo[2,3-b]pyridine-2-carboxylic acid naphthalen-1-ylamide | 0.0545 | 35.06 |
| 20 | (R)-1-[(S)-3-Methyl-2-((S)-2-methylamino-propionylamino)-butyryl]-2,3-dihydro-1H-pyrrolo[2,3-b]pyridine-2-carboxylic acid (4-methyl-pyridin-3-yl)-amide | 1.363 | >54.8 |
| 21 | (S)-1-[(S)-3-Methyl-2-((S)-2-methylamino-propionylamino)-butyryl]-2,3-dihydro-1H-pyrrolo[2,3-b]pyridine-2-carboxylic acid (4-fluoro-phenyl)-amide | 0.275 | >54.8 |
| 22 | (S)-1-[(S)-3-Methyl-2-((S)-2-methylamino-propionylamino)-butyryl]-2,3-dihydro-1H-pyrrolo[2,3-b]pyridine-2-carboxylic acid (4-fluoro-2-methyl-phenyl)-amide | 0.103 | >54.8 |
| 23 | (S)-1-[(S)-3-Methyl-2-((S)-2-methylamino-propionylamino)-butyryl]-2,3-dihydro-1H-pyrrolo[2,3-b]pyridine-2-carboxylic acid (3,5-difluoro-phenyl)-amide | 0.427 | >54.8 |
| 24 | (S)-1-[(S)-3-Methyl-2-((S)-2-methylamino-propionylamino)-butyryl]-2,3-dihydro-1H-pyrrolo[2,3-b]pyridine-2-carboxylic acid 4-fluoro-benzylamide | 0.774 | 9.208 |
| 25 | (S)-1-[(S)-3-Methyl-2-((S)-2-methylamino-propionylamino)-butyryl]-2,3-dihydro-1H-pyrrolo[2,3-b]pyridine-2-carboxylic acid (2-chloro-phenyl)-amide | 0.0254 | >54.8 |
| 26 | (S)-1-[(S)-3-Methyl-2-((S)-2-methylamino-propionylamino)-butyryl]-2,3-dihydro-1H-pyrrolo[2,3-b]pyridine-2-carboxylic acid (2-benzoyl-phenyl)-amide | 0.061 | 52.34 |

TABLE 11-continued

| | Systematic Name | Ic50 BIR2 | Ic50 BIR3 |
|---|---|---|---|
| 27 | (R)-1-[(S)-3-Methyl-2-((S)-2-methylamino-propionylamino)-butyryl]-2,3-dihydro-1H-pyrrolo[2,3-b]pyridine-2-carboxylic acid (2-benzoyl-phenyl)-amide | 2.112 | >54.8 |
| 28 | (S)-1-[(S)-3-Methyl-2-((S)-2-methylamino-propionylamino)-butyryl]-2,3-dihydro-1H-pyrrolo[2,3-b]pyridine-2-carboxylic acid (2,6-difluoro-phenyl)-amide | 0.0144 | >54.8 |
| 29 | (R)-1-[(S)-3-Methyl-2-((S)-2-methylamino-propionylamino)-butyryl]-2,3-dihydro-1H-pyrrolo[2,3-b]pyridine-2-carboxylic acid (2,6-difluoro-phenyl)-amide | 0.421 | >54.8 |
| 30 | (S)-1-[(S)-3-Methyl-2-((S)-2-methylamino-propionylamino)-butyryl]-2,3-dihydro-1H-pyrrolo[2,3-b]pyridine-2-carboxylic acid (2-phenoxy-phenyl)-amide | 0.158 | 46.8 |
| 31 | (R)-1-[(S)-3-Methyl-2-((S)-2-methylamino-propionylamino)-butyryl]-2,3-dihydro-1H-pyrrolo[2,3-b]pyridine-2-carboxylic acid (2-phenoxy-phenyl)-amide | 11.74 | >54.8 |
| 32 | (S)-1-[(S)-3-Methyl-2-((S)-2-methylamino-propionylamino)-butyryl]-2,3-dihydro-1H-pyrrolo[2,3-b]pyridine-2-carboxylic acid (2-fluoro-6-methyl-phenyl)-amide | 0.00959 | >54.8 |
| 33 | (S)-1-[(S)-3-Methyl-2-((S)-2-methylamino-propionylamino)-butyryl]-2,3-dihydro-1H-pyrrolo[2,3-b]pyridine-2-carboxylic acid (2,6-dimethyl-phenyl)-amide | 0.0449 | >54.8 |
| 34 | (S)-N-{(S)-1-[(S)-2-(1H-Benzoimidazol-2-yl)-2,3-dihydro-pyrrolo[2,3-b]pyridine-1-carbonyl]-2-methyl-propyl}-2-methylamino-propionamide | 0.137 | >54.8 |
| 35 | (S)-N-{(S)-1-[(R)-2-(1H-Benzoimidazol-2-yl)-2,3-dihydro-pyrrolo[2,3-b]pyridine-1-carbonyl]-2-methyl-propyl}-2-methylamino-propionamide | 37.73 | >54.8 |
| 36 | (S)-1-[(S)-3-Methyl-2-((S)-2-methylamino-propionylamino)-butyryl]-2,3-dihydro-1H-pyrrolo[2,3-b]pyridine-2-carboxylic acid (2-fluoro-phenyl)-amide | 0.0127 | >54.8 |
| 37 | (S)-1-[(S)-3-Methyl-2-((S)-2-methylamino-propionylamino)-butyryl]-2,3-dihydro-1H-pyrrolo[2,3-b]pyridine-2-carboxylic acid (2,2,2-trifluoro-ethyl)-amide | 0.323 | >54.8 |
| 38 | (S)-1-[(S)-3-Methyl-2-((S)-2-methylamino-propionylamino)-butyryl]-2,3-dihydro-1H-pyrrolo[2,3-b]pyridine-2-carboxylic acid (4-methyl-pyridin-3-yl)-amide | 0.237 | >54.8 |
| 39 | (S)-1-[(S)-3-Methyl-2-((S)-2-methylamino-propionylamino)-butyryl]-2,3-dihydro-1H-pyrrolo[2,3-b]pyridine-2-carboxylic acid (3-fluoro-phenyl)-amide | 0.226 | >54.8 |
| 40 | (S)-1-[(S)-3-Methyl-2-((S)-2-methylamino-propionylamino)-butyryl]-2,3-dihydro-1H-pyrrolo[2,3-b]pyridine-2-carboxylic acid (2-ethyl-phenyl)-amide | 0.104 | >54.8 |
| 41 | (S)-1-[(S)-3-Methyl-2-((S)-2-methylamino-propionylamino)-butyryl]-2,3-dihydro-1H-pyrrolo[2,3-b]pyridine-2-carboxylic acid (4-piperidin-4-yl-phenyl)-amide | 0.701 | >54.8 |
| 42 | (S)-1-[(S)-3-Methyl-2-((S)-2-methylamino-propionylamino)-butyryl]-2,3-dihydro-1H-pyrrolo[2,3-b]pyridine-2-carboxylic acid (4-benzoyl-phenyl)-amide | 0.847 | >54.8 |
| 43 | (S)-1-[(S)-3-Methyl-2-((S)-2-methylamino-propionylamino)-butyryl]-2,3-dihydro-1H-pyrrolo[2,3-b]pyridine-2-carboxylic acid (2,3-dimethyl-phenyl)-amide | 0.0711 | >54.8 |
| 44 | (S)-1-[(S)-3-Methyl-2-((S)-2-methylamino-propionylamino)-butyryl]-2,3-dihydro-1H-pyrrolo[2,3-b]pyridine-2-carboxylic acid (2-fluoro-5-methyl-phenyl)-amide | 0.0038 | >54.8 |
| 45 | (S)-1-[(S)-3-Methyl-2-((S)-2-methylamino-propionylamino)-butyryl]-2,3-dihydro-1H-pyrrolo[2,3-b]pyridine-2-carboxylic acid (3,5-dimethyl-phenyl)-amide | 0.304 | >54.8 |
| 46 | (S)-1-[(S)-3-Methyl-2-((S)-2-methylamino-propionylamino)-butyryl]-2,3-dihydro-1H-pyrrolo[2,3-b]pyridine-2-carboxylic acid (2-fluoro-4-methyl-phenyl)-amide | 0.00404 | >54.8 |
| 47 | (S)-1-[(S)-3-Methyl-2-((S)-2-methylamino-propionylamino)-butyryl]-2,3-dihydro-1H-pyrrolo[2,3-b]pyridine-2-carboxylic acid (2-fluoro-4-methoxy-phenyl)-amide | 0.00429 | >54.8 |
| 48 | (S)-1-[(S)-3-Methyl-2-((S)-2-methylamino-propionylamino)-butyryl]-2,3-dihydro-1H-pyrrolo[2,3-b]pyridine-2-carboxylic acid (2-cyano-phenyl)-amide | 0.0549 | >54.8 |
| 49 | 3-Fluoro-4-({(S)-1-[(S)-3-methyl-2-((S)-2-methylamino-propionylamino)-butyryl]-2,3-dihydro-1H-pyrrolo[2,3-b]pyridine-2-carbonyl}-amino)-benzoic acid methyl ester | 0.102 | >54.8 |
| 50 | (S)-1-[(S)-3-Methyl-2-((S)-2-methylamino-propionylamino)-butyryl]-2,3-dihydro-1H-pyrrolo[2,3-b]pyridine-2-carboxylic acid (2-fluoro-4-methanesulfonyl-phenyl)-amide | 0.0893 | >54.8 |
| 51 | (S)-1-[(S)-3-Methyl-2-((S)-2-methylamino-propionylamino)-butyryl]-2,3-dihydro-1H-pyrrolo[2,3-b]pyridine-2-carboxylic acid (2-methanesulfonyl-ethyl)-amide | 0.828 | >54.8 |
| 52 | (S)-1-[(S)-3-Methyl-2-((S)-2-methylamino-propionylamino)-butyryl]-2,3-dihydro-1H-pyrrolo[2,3-b]pyridine-2-carboxylic acid (1-phenyl-ethyl)-amide | 0.978 | 21.55 |
| 53 | (S)-1-[(S)-3-Methyl-2-((S)-2-methylamino-propionylamino)-butyryl]-2,3-dihydro-1H-pyrrolo[2,3-b]pyridine-2-carboxylic acid (2-dimethylsulfamoyl-ethyl)-amide | 0.74 | >54.8 |
| 54 | (S)-1-[(S)-3-Methyl-2-((S)-2-methylamino-propionylamino)-butyryl]-2,3-dihydro-1H-pyrrolo[2,3-b]pyridine-2-carboxylic acid (1-methyl-1-phenyl-ethyl)-amide | 4.733 | 47.37 |
| 55 | (S)-1-[(S)-3-Methyl-2-((S)-2-methylamino-propionylamino)-butyryl]-2,3-dihydro-1H-pyrrolo[2,3-b]pyridine-2-carboxylic acid 5-fluoro-2-methyl-benzylamide | 0.139 | 35.35 |
| 56 | (S)-1-[(S)-3-Methyl-2-((S)-2-methylamino-propionylamino)-butyryl]-2,3-dihydro-1H-pyrrolo[2,3-b]pyridine-2-carboxylic acid pyrimidin-5-ylamide | 1.633 | >54.8 |
| 57 | (S)-1-[(S)-3-Methyl-2-((S)-2-methylamino-propionylamino)-butyryl]-2,3-dihydro-1H-pyrrolo[2,3-b]pyridine-2-carboxylic acid naphthalen-2-ylamide | 0.164 | >54.8 |
| 58 | (S)-1-[(S)-3-Methyl-2-((S)-2-methylamino-propionylamino)-butyryl]-2,3-dihydro-1H-pyrrolo[2,3-b]pyridine-2-carboxylic acid (4-cyano-2-fluoro-phenyl)-amide | 0.14 | >54.8 |
| 59 | (S)-1-[(S)-3-Methyl-2-((S)-2-methylamino-propionylamino)-butyryl]-2,3-dihydro-1H-pyrrolo[2,3-b]pyridine-2-carboxylic acid (2-fluoro-4-trifluoromethyl-phenyl)-amide | 0.0536 | >54.8 |
| 60 | (S)-1-[(S)-3-Methyl-2-((S)-2-methylamino-propionylamino)-butyryl]-2,3-dihydro-1H-pyrrolo[2,3-b]pyridine-2-carboxylic acid (2,3-difluoro-phenyl)-amide | 0.0382 | >54.8 |
| 61 | (S)-1-[(S)-3-Methyl-2-((S)-2-methylamino-propionylamino)-butyryl]-2,3-dihydro-1H-pyrrolo[2,3-b]pyridine-2-carboxylic acid (2,5-difluoro-phenyl)-amide | 0.0348 | >54.8 |
| 62 | (S)-1-[(S)-3-Methyl-2-((S)-2-methylamino-propionylamino)-butyryl]-2,3-dihydro-1H-pyrrolo[2,3-b]pyridine-2-carboxylic acid (4-dimethylcarbamoyl-2-fluoro-phenyl)-amide | 0.0351 | >54.8 |
| 63 | (S)-1-[(S)-3-Methyl-2-((S)-2-methylamino-propionylamino)-butyryl]-2,3-dihydro-1H-pyrrolo[2,3-b]pyridine-2-carboxylic acid (4-bromo-2-fluoro-phenyl)-amide | 0.032 | >54.8 |
| 64 | (S)-1-[(S)-3-Methyl-2-((S)-2-methylamino-propionylamino)-butyryl]-2,3-dihydro-1H-pyrrolo[2,3-b]pyridine-2-carboxylic acid (2-fluoro-4-methylcarbamoyl-phenyl)-amide | 0.0596 | >54.8 |

TABLE 11-continued

| | Systematic Name | Ic50 BIR2 | Ic50 BIR3 |
|---|---|---|---|
| 65 | (S)-1-[(S)-3-Methyl-2-((S)-2-methylamino-propionylamino)-butyryl]-2,3-dihydro-1H-pyrrolo[2,3-b]pyridine-2-carboxylic acid (2,4-difluoro-phenyl)-amide | 0.0351 | >54.8 |
| 66 | (S)-1-[(S)-3-Methyl-2-((S)-2-methylamino-propionylamino)-butyryl]-2,3-dihydro-1H-pyrrolo[2,3-b]pyridine-2-carboxylic acid (4-methyl-thiazol-2-yl)-amide | 0.496 | >54.8 |
| 67 | (S)-1-[(S)-3-Methyl-2-((S)-2-methylamino-propionylamino)-butyryl]-2,3-dihydro-1H-pyrrolo[2,3-b]pyridine-2-carboxylic acid (5-methyl-thiazol-2-yl)-amide | 0.0926 | >54.8 |
| 68 | (S)-1-[(S)-3-Methyl-2-((S)-2-methylamino-propionylamino)-butyryl]-2,3-dihydro-1H-pyrrolo[2,3-b]pyridine-2-carboxylic acid benzothiazol-2-ylamide | 0.288 | >54.8 |
| 69 | (S)-1-[(S)-3-Methyl-2-((S)-2-methylamino-propionylamino)-butyryl]-2,3-dihydro-1H-pyrrolo[2,3-b]pyridine-2-carboxylic acid (3-fluoro-pyridin-4-yl)-amide | 0.105 | >54.8 |
| 70 | (S)-1-[(S)-3-Methyl-2-((S)-2-methylamino-propionylamino)-butyryl]-2,3-dihydro-1H-pyrrolo[2,3-b]pyridine-2-carboxylic acid (2-chloro-6-fluoro-phenyl)-amide | 0.0215 | >54.8 |
| 71 | (S)-1-[(S)-3-Methyl-2-((S)-2-methylamino-propionylamino)-butyryl]-2,3-dihydro-1H-pyrrolo[2,3-b]pyridine-2-carboxylic acid (2-chloro-6-methyl-phenyl)-amide | 0.0192 | >54.8 |
| 72 | (S)-1-[(S)-3-Methyl-2-((S)-2-methylamino-propionylamino)-butyryl]-2,3-dihydro-1H-pyrrolo[2,3-b]pyridine-2-carboxylic acid (2,4,6-trichloro-phenyl)-amide | 0.0137 | >54.8 |
| 73 | (S)-1-[(S)-3-Methyl-2-((S)-2-methylamino-propionylamino)-butyryl]-2,3-dihydro-1H-pyrrolo[2,3-b]pyridine-2-carboxylic acid (2-fluoro-6-trifluoromethyl-phenyl)-amide | 0.0691 | >54.8 |
| 74 | (S)-1-[(S)-3-Methyl-2-((S)-2-methylamino-propionylamino)-butyryl]-2,3-dihydro-1H-pyrrolo[2,3-b]pyridine-2-carboxylic acid (2,6-dichloro-phenyl)-amide | 0.0166 | >54.8 |
| 75 | (S)-1-[(S)-3-Methyl-2-((S)-2-methylamino-propionylamino)-butyryl]-2,3-dihydro-1H-pyrrolo[2,3-b]pyridine-2-carboxylic acid (2-chloro-6-trifluoromethyl-phenyl)-amide | 0.0575 | >54.8 |
| 76 | (S)-1-[(S)-2-Cyclohexyl-2-((S)-2-ethylamino-propionylamino)-acetyl]-2,3-dihydro-1H-pyrrolo[2,3-b]pyridine-2-carboxylic acid phenylamide | 0.353 | >54.8 |
| 77 | (S)-1-[(S)-2-((S)-2-Ethylamino-propionylamino)-3-methyl-butyryl]-2,3-dihydro-1H-pyrrolo[2,3-b]pyridine-2-carboxylic acid (2,6-difluoro-phenyl)-amide | 0.0462 | >54.8 |
| 78 | (S)-1-[(S)-3-Methyl-2-((S)-2-methylamino-butyrylamino)-butyryl]-2,3-dihydro-1H-pyrrolo[2,3-b]pyridine-2-carboxylic acid (2,6-difluoro-phenyl)-amide | 0.0142 | >54.8 |
| 79 | (R)-1-[(S)-2-Cyclohexyl-2-((S)-2-methylamino-propionylamino)-acetyl]-2,3-dihydro-1H-pyrrolo[2,3-b]pyridine-2-carboxylic acid phenylamide | >54.8 | >54.8 |
| 80 | (S)-1-[(S)-2-Cyclohexyl-2-((S)-2-methylamino-propionylamino)-acetyl]-2,3-dihydro-1H-pyrrolo[2,3-b]pyridine-2-carboxylic acid phenylamide | 0.117 | >54.8 |
| 81 | (R)-1-[(S)-2-Cyclohexyl-2-((S)-2-methylamino-butyrylamino)-acetyl]-2,3-dihydro-1H-pyrrolo[2,3-b]pyridine-2-carboxylic acid phenylamide | 10.36 | >54.8 |
| 82 | 1-[(S)-2-Cyclohexyl-2-((S)-2-methylamino-butyrylamino)-acetyl]-2,3-dihydro-1H-pyrrolo[2,3-b]pyridine-2-carboxylic acid phenylamide | 0.105 | >54.8 |
| 83 | 1-[(S)-2-Cyclohexyl-2-((S)-2-(d3-methyl)amino-butyrylamino)-acetyl]-2,3-dihydro-1H-pyrrolo[2,3-b]pyridine-2-carboxylic acid phenylamide | 0.0528 | >54.8 |
| 84 | (S)-1-[(S)-2-((S)-2-Amino-propionylamino)-2-cyclohexyl-acetyl]-2,3-dihydro-1H-pyrrolo[2,3-b]pyridine-2-carboxylic acid phenylamide | | |
| 85 | (S)-1-[(S)-3-Methyl-2-((S)-2-methylamino-butyrylamino)-butyryl]-2,3-dihydro-1H-pyrrolo[2,3-b]pyridine-2-carboxylic acid phenylamide | 0.0691 | >54.8 |
| 86 | (S)-1-[(S)-3-Methyl-2-((S)-2-(d3-methyl)amino-butyrylamino)-butyryl]-2,3-dihydro-1H-pyrrolo[2,3-b]pyridine-2-carboxylic acid phenylamide | 0.0656 | >54.8 |
| 87 | (S)-1-[(S)-2-((S)-2-Ethylamino-propionylamino)-3-methyl-butyryl]-2,3-dihydro-1H-pyrrolo[2,3-b]pyridine-2-carboxylic acid phenylamide | 0.234 | >54.8 |
| 88 | (S)-1-[(S)-2-((S)-2-Ethylamino-butyrylamino)-3-methyl-butyryl]-2,3-dihydro-1H-pyrrolo[2,3-b]pyridine-2-carboxylic acid phenylamide | 0.211 | >54.8 |
| 89 | (S)-1-{(S)-2-[(S)-2-(2-Hydroxy-ethylamino)-propionylamino]-3-methyl-butyryl}-2,3-dihydro-1H-pyrrolo[2,3-b]pyridine-2-carboxylic acid phenylamide | 0.266 | >54.8 |
| 90 | (S)-1-{(S)-2-[(S)-2-(2-Hydroxy-ethylamino)-butyrylamino]-3-methyl-butyryl}-2,3-dihydro-1H-pyrrolo[2,3-b]pyridine-2-carboxylic acid phenylamide | 1.608 | >54.8 |
| 91 | (S)-1-{(S)-2-Cyclohexyl-2-[(S)-2-(2-hydroxy-ethylamino)-propionylamino]-acetyl}-2,3-dihydro-1H-pyrrolo[2,3-b]pyridine-2-carboxylic acid phenylamide | 0.155 | >54.8 |
| 92 | (S)-1-{(S)-2-[(S)-2-(2-Methanesulfonyl-ethylamino)-propionylamino]-3-methyl-butyryl}-2,3-dihydro-1H-pyrrolo[2,3-b]pyridine-2-carboxylic acid (2,6-difluoro-phenyl)-amide | 2.57 | >54.8 |
| 93 | (S)-1-{(S)-2-[(S)-2-(2-Methoxy-ethylamino)-propionylamino]-3-methyl-butyryl}-2,3-dihydro-1H-pyrrolo[2,3-b]pyridine-2-carboxylic acid (2,6-difluoro-phenyl)-amide | | |
| 94 | (S)-1-[(S)-2-((S)-2-Methylamino-propionylamino)-2-(tetrahydro-pyran-4-yl)-acetyl]-2,3-dihydro-1H-pyrrolo[2,3-b]pyridine-2-carboxylic acid (2,6-difluoro-phenyl)-amide | 0.00979 | >54.8 |
| 95 | (R)-1-[(S)-2-((S)-2-Methylamino-propionylamino)-2-(tetrahydro-pyran-4-yl)-acetyl]-2,3-dihydro-1H-pyrrolo[2,3-b]pyridine-2-carboxylic acid (2,6-difluoro-phenyl)-amide | 0.607 | >54.8 |
| 96 | 1-[(S)-4-Methanesulfonyl-2-((S)-2-methylamino-propionylamino)-butyryl]-2,3-dihydro-1H-pyrrolo[2,3-b]pyridine-2-carboxylic acid phenylamide | 0.108 | >54.8 |
| 97 | 1-[(S)-4-Methanesulfonyl-2-((S)-2-methylamino-propionylamino)-butyryl]-2,3-dihydro-1H-pyrrolo[2,3-b]pyridine-2-carboxylic acid phenylamide | 3.06 | >54.8 |
| 98 | 3-Methyl-1-[(S)-3-methyl-2-((S)-2-methylamino-propionylamino)-butyryl]-2,3-dihydro-1H-pyrrolo[2,3-b]pyridine-2-carboxylic acid (2,6-difluoro-phenyl)-amide | 0.017 | >54.8 |
| 99 | (S)-1-[(S)-2-((S)-2-Methylamino-propionylamino)-2-(tetrahydro-pyran-4-yl)-acetyl]-2,3-dihydro-1H-pyrrolo[2,3-b]pyridine-2-carboxylic acid (2-fluoro-6-methyl-phenyl)-amide | 0.0116 | >54.8 |

The invention claimed is:

1. A compound of Formula I:

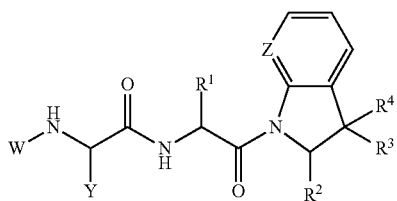

I wherein:
W is selected from the group
a) H,
b) $C_{1-6}$-alkyl that optionally includes 1-3 deuterium atoms, and
c) $C_{1-6}$-alkyl that optionally may be substituted with $SO_2R^5$ and $OR^5$;
Y is $C_{1-6}$-alkyl that optionally may be substituted with $OR^5$;
Z is N;
$R^1$ is selected from the group
a) $C_{1-6}$-alkyl that optionally may be substituted with $SO_2R^5$,
b) $C_{3-7}$-cycloalkyl,
c) heterocyclyl, and
d) aryl;
$R^2$ is selected from the group
a) H
b) $C(O)NHR^6$,
c) heterocyclyl, and
d) heteroaryl;
$R^3$ and $R^4$ may be the same or different and each is independently selected from the group
a) H, and
b) $C_{1-6}$-alkyl;
$R^5$ is selected from the group
a) H,
b) $C_{1-6}$-alkyl,
c) $NR^7R^8$, and
d) aryl;
$R^6$ is selected from the group
a) H,
b) aryl that optionally may be substituted with $C_{1-6}$-alkyl, $OR^5$, halogen, $C(O)OR^5$, $C(O)NR^7R^8$, aryl, heterocyclyl, $C(O)R^9$, $SO_2R^5$, cyano and $CF_3$,
c) $C_{1-6}$-alkyl that optionally may be substituted with $CF_3$, $SO_2R^5$ and aryl that optionally may be substituted with $C_{1-6}$-alkyl and halogen,
d) heteroaryl that optionally may be substituted with $C_{1-6}$-alkyl, $OR^5$, halogen, aryl and oxo, and
e) heterocyclyl;

$R^7$ and $R^8$ may be the same or different and each is independently selected from the group
a) H,
b) $C_{1-6}$-alkyl, and
c) aryl;
$R^9$ is selected from the group
a) $C_{1-6}$-alkyl, and
b) aryl;
or a pharmaceutically acceptable salt thereof.

2. The compound of claim 1 wherein W is $C_{1-6}$-alkyl, or a pharmaceutically acceptable salt of said compound.

3. The compound according to claim 2 wherein W is methyl, or a pharmaceutically acceptable salt of said compound.

4. The compound of claim 1 wherein Y is $C_{1-6}$-alkyl, or a pharmaceutically acceptable salt of said compound.

5. The compound of claim 4 wherein Y is methyl or ethyl, or a pharmaceutically acceptable salt of said compound.

6. The compound according to claim 1 wherein $R^1$ is $C_{1-6}$-alkyl, or a pharmaceutically acceptable salt of said compound.

7. The compound according to claim 1 wherein $R^1$ is $C_{3-7}$ cycloalkyl, or a pharmaceutically acceptable salt of said compound.

8. The compound according to claim 1 wherein $R^1$ is heterocyclyl, or a pharmaceutically acceptable salt of said compound.

9. The compound according to claim 1 wherein $R^1$ is aryl, or a pharmaceutically acceptable salt of said compound.

10. The compound according to claim 1 wherein $R^2$ is H, or a pharmaceutically acceptable salt of said compound.

11. The compound according to claim 1 wherein $R^2$ is heteroaryl, or a pharmaceutically acceptable salt of said compound.

12. The compound according to claim 1 wherein $R^2$ is $C(O)NHR^6$, or a pharmaceutically acceptable salt of said compound.

13. The compound of claim 12 wherein $R^6$ is aryl that optionally may be substituted with $C_{1-6}$-alkyl, $OR^5$, halogen, $C(O)OR^5$, $C(O)NR^7R^5$, aryl, heterocyclyl, $C(O)R^9$, $SO_2R^5$, cyano and $CF_3$, or a pharmaceutically acceptable salt of said compound.

14. The compound of claim 12 wherein $R^6$ is $C_{1-6}$-alkyl that optionally may be substituted with $CF_3$, $SO_2R^5$, and aryl that optionally may be substituted with $C_{1-6}$-alkyl and halogen, or a pharmaceutically acceptable salt of said compound.

15. The compound of claim 12 wherein $R^6$ is heteroaryl that optionally may be substituted with $C_{1-6}$-alkyl, $OR^5$, halogen, aryl and oxo, or a pharmaceutically acceptable salt of said compound.

16. The compound according to claim 1 wherein $R^3$ and $R^4$ are H, or a pharmaceutically acceptable salt of said compound.

17. The compound according to claim 1 wherein one of $R^3$ and $R^4$ is H and the other is methyl, or a pharmaceutically acceptable salt of said compound.

18. The compound according to claim 1 wherein $R^3$ and $R^4$ are both methyl, or a pharmaceutically acceptable salt of said compound.

19. The compound according to claim 1 wherein $R^5$ is $C_{1-6}$-alkyl, or a pharmaceutically acceptable salt of said compound.

20. The compound according to claim 1 wherein $R^5$ is aryl, or a pharmaceutically acceptable salt of said compound.

21. The compound of claim 1 wherein $R^2$ is $C(O)NHR^6$ and $R^6$ is aryl that optionally may be substituted with $C_{1-6}$-alkyl, $OR^5$, halogen, $C(O)OR^5$, $C(O)NR^7R^8$, aryl, heterocyclyl, $C(O)R^9$, $SO_2R^5$, cyano and $CF_3$, or a pharmaceutically acceptable salt of said compound.

22. The compound of claim 1 wherein $R^2$ is $C(O)NHR^6$ and $R^6$ is $C_{1-6}$-alkyl that optionally may be substituted with $CF_3$, $SO_2R^5$ and aryl that optionally may be substituted with $C_{1-6}$-alkyl and halogen, or a pharmaceutically acceptable salt of said compound.

23. The compound of claim 1 wherein $R^2$ is $C(O)NHR^6$ and $R^6$ is heteroaryl that optionally may be substituted with $C_{1-6}$-alkyl, $OR^5$, halogen, aryl and oxo, or a pharmaceutically acceptable salt of said compound.

24. The compound of claim 1 wherein W, Y and $R^1$ are $C_{1-6}$-alkyl; $R^2$ is $C(O)NHR^6$; $R^6$ is aryl that optionally may be substituted with halogen, $C_{1-6}$-alkyl and $OR^5$; and $R^5$ is $C_{1-6}$-alkyl, or a pharmaceutically acceptable salt of said compound.

25. The compound of claim 1 wherein W, Y are $C_{1-6}$-alkyl; $R^1$ is heterocyclyl; $R^2$ is $C(O)NHR^6$; and $R^6$ is aryl that optionally may be substituted with halogen and $C_{1-6}$-alkyl, or a pharmaceutically acceptable salt thereof.

26. The compound of claim 1 selected from the group consisting of:
- (R,S)-1-[(S)-3-Methyl-2-((S)-2-methylamino-propionylamino)-butyryl]-2,3-dihydro-1H-pyrrolo[2,3-b]pyridine-2-carboxylic acid ethylamide;
- (R,S)-1-[(S)-2-Cyclohexyl-2-((S)-2-methylamino-propionylamino)-acetyl]-2,3-dihydro-1H-pyrrolo[2,3-b]pyridine-2-carboxylic acid ethylamide;
- (R,S)-1-[(S)-2-Cyclohexyl-2-((S)-2-methylamino-butyrylamino)-acetyl]-2,3-dihydro-1H-pyrrolo[2,3-b]pyridine-2-carboxylic acid ethylamide;
- (R,S)-1-[(2S,3S)-3-Methyl-2-((S)-2-methylamino-propionylamino)-pentanoyl]-2,3-dihydro-1H-pyrrolo[2,3-b]pyridine-2-carboxylic acid ethylamide;
- (R,S)-1-[(2S,3S)-3-Methyl-2-((S)-2-methylamino-butyrylamino)-pentanoyl]-2,3-dihydro-1H-pyrrolo[2,3-b]pyridine-2-carboxylic acid ethylamide;
- (R,S)-1-[(S)-3-Methyl-2-((S)-2-methylamino-propionylamino)-butyryl]-2,3-dihydro-1H-pyrrolo[2,3-b]pyridine-2-carboxylic acid amide;
- (R)-1-[(S)-3-Methyl-2-((S)-2-methylamino-propionylamino)-butyryl]-2,3-dihydro-1H-pyrrolo[2,3-b]pyridine-2-carboxylic acid (2-methoxy-phenyl)-amide;
- (S)-1-[(S)-3-Methyl-2-((S)-2-methylamino-propionylamino)-butyryl]-2,3-dihydro-1H-pyrrolo[2,3-b]pyridine-2-carboxylic acid (2-methoxy-phenyl)-amide;
- (S)-1-[(S)-3-Methyl-2-((S)-2-methylamino-propionylamino)-butyryl]-2,3-dihydro-1H-pyrrolo[2,3-b]pyridine-2-carboxylic acid phenylamide;
- (R)-1-[(S)-3-Methyl-2-((S)-2-methylamino-propionylamino)-butyryl]-2,3-dihydro-1H-pyrrolo[2,3-b]pyridine-2-carboxylic acid phenylamide;
- (R)-1-[(S)-3-Methyl-2-((S)-2-methylamino-propionylamino)-butyryl]-2,3-dihydro-1H-pyrrolo[2,3-b]pyridine-2-carboxylic acid o-tolylamide;
- (S)-1-[(S)-3-Methyl-2-((S)-2-methylamino-propionylamino)-butyryl]-2,3-dihydro-1H-pyrrolo[2,3-b]pyridine-2-carboxylic acid o-tolylamide;
- (R)-1-[(S)-3-Methyl-2-((S)-2-methylamino-propionylamino)-butyryl]-2,3-dihydro-1H-pyrrolo[2,3-b]pyridine-2-carboxylic acid benzylamide;
- (S)-1-[(S)-3-Methyl-2-((S)-2-methylamino-propionylamino)-butyryl]-2,3-dihydro-1H-pyrrolo[2,3-b]pyridine-2-carboxylic acid benzylamide;
- (S)-1-[(S)-3-Methyl-2-((S)-2-methylamino-propionylamino)-butyryl]-2,3-dihydro-1H-pyrrolo[2,3-b]pyridine-2-carboxylic acid 5-chloro-2-methyl-benzylamide;
- (S)-1-[(S)-3-Methyl-2-((S)-2-methylamino-propionylamino)-butyryl]-2,3-dihydro-1H-pyrrolo[2,3-b]pyridine-2-carboxylic acid biphenyl-2-ylamide;
- (S)-1-[(S)-3-Methyl-2-((S)-2-methylamino-propionylamino)-butyryl]-2,3-dihydro-1H-pyrrolo[2,3-b]pyridine-2-carboxylic acid naphthalen-1-ylamide;
- (R)-1-[(S)-3-Methyl-2-((S)-2-methylamino-propionylamino)-butyryl]-2,3-dihydro-1H-pyrrolo[2,3-b]pyridine-2-carboxylic acid (4-methyl-pyridin-3-yl)-amide;
- (S)-1-[(S)-3-Methyl-2-((S)-2-methylamino-propionylamino)-butyryl]-2,3-dihydro-1H-pyrrolo[2,3-b]pyridine-2-carboxylic acid (4-fluoro-phenyl)-amide;
- (S)-1-[(S)-3-Methyl-2-((S)-2-methylamino-propionylamino)-butyryl]-2,3-dihydro-1H-pyrrolo[2,3-b]pyridine-2-carboxylic acid (4-fluoro-2-methyl-phenyl)-amide;
- (S)-1-[(S)-3-Methyl-2-((S)-2-methylamino-propionylamino)-butyryl]-2,3-dihydro-1H-pyrrolo[2,3-b]pyridine-2-carboxylic acid (3,5-difluoro-phenyl)-amide;
- (S)-1-[(S)-3-Methyl-2-((S)-2-methylamino-propionylamino)-butyryl]-2,3-dihydro-1H-pyrrolo[2,3-b]pyridine-2-carboxylic acid 4-fluoro-benzylamide;
- (S)-1-[(S)-3-Methyl-2-((S)-2-methylamino-propionylamino)-butyryl]-2,3-dihydro-1H-pyrrolo[2,3-b]pyridine-2-carboxylic acid (2-chloro-phenyl)-amide;
- (S)-1-[(S)-3-Methyl-2-((S)-2-methylamino-propionylamino)-butyryl]-2,3-dihydro-1H-pyrrolo[2,3-b]pyridine-2-carboxylic acid (2-benzoyl-phenyl)-amide;
- (R)-1-[(S)-3-Methyl-2-((S)-2-methylamino-propionylamino)-butyryl]-2,3-dihydro-1H-pyrrolo[2,3-b]pyridine-2-carboxylic acid (2-benzoyl-phenyl)-amide;
- (S)-1-[(S)-3-Methyl-2-((S)-2-methylamino-propionylamino)-butyryl]-2,3-dihydro-1H-pyrrolo[2,3-b]pyridine-2-carboxylic acid (2,6-difluoro-phenyl)-amide;
- (R)-1-[(S)-3-Methyl-2-((S)-2-methylamino-propionylamino)-butyryl]-2,3-dihydro-1H-pyrrolo[2,3-b]pyridine-2-carboxylic acid (2,6-difluoro-phenyl)-amide;
- (S)-1-[(S)-3-Methyl-2-((S)-2-methylamino-propionylamino)-butyryl]-2,3-dihydro-1H-pyrrolo[2,3-b]pyridine-2-carboxylic acid (2-phenoxy-phenyl)-amide;
- (R)-1-[(S)-3-Methyl-2-((S)-2-methylamino-propionylamino)-butyryl]-2,3-dihydro-1H-pyrrolo[2,3-b]pyridine-2-carboxylic acid (2-phenoxy-phenyl)-amide;
- (S)-1-[(S)-3-Methyl-2-((S)-2-methylamino-propionylamino)-butyryl]-2,3-dihydro-1H-pyrrolo[2,3-b]pyridine-2-carboxylic acid (2-fluoro-6-methyl-phenyl)-amide;
- (S)-1-[(S)-3-Methyl-2-((S)-2-methylamino-propionylamino)-butyryl]-2,3-dihydro H-pyrrolo[2,3-b]pyridine-2-carboxylic acid (2,6-dimethyl-phenyl)-amide;
- (S)-1-[(S)-3-Methyl-2-((S)-2-methylamino-propionylamino)-butyryl]-2,3-dihydro-1H-pyrrolo[2,3-b]pyridine-2-carboxylic acid (2-fluoro-phenyl)-amide;

(S)-1-[(S)-3-Methyl-2-((S)-2-methylamino-propionylamino)-butyryl]-2,3-dihydro-1H-pyrrolo[2,3-b]pyridine-2-carboxylic acid (2,2,2-trifluoro-ethyl)-amide;
(S)-1-[(S)-3-Methyl-2-((S)-2-methylamino-propionylamino)-butyryl]-2,3-dihydro-1H-pyrrolo[2,3-b]pyridine-2-carboxylic acid (4-methyl-pyridin-3-yl)-amide;
(S)-1-[(S)-3-Methyl-2-((S)-2-methylamino-propionylamino)-butyryl]-2,3-dihydro-1H-pyrrolo[2,3-b]pyridine-2-carboxylic acid (3-fluoro-phenyl)-amide;
(S)-1-[(S)-3-Methyl-2-((S)-2-methylamino-propionylamino)-butyryl]-2,3-dihydro-1H-pyrrolo[2,3-b]pyridine-2-carboxylic acid (2-ethyl-phenyl)-amide;
(S)-1-[(S)-3-Methyl-2-((S)-2-methylamino-propionylamino)-butyryl]-2,3-dihydro-1H-pyrrolo[2,3-b]pyridine-2-carboxylic acid (4-piperidin-4-yl-phenyl)-amide;
(S)-1-[(S)-3-Methyl-2-((S)-2-methylamino-propionylamino)-butyryl]-2,3-dihydro-1H-pyrrolo[2,3-b]pyridine-2-carboxylic acid (4-benzoyl-phenyl)-amide;
(S)-1-[(S)-3-Methyl-2-((S)-2-methylamino-propionylamino)-butyryl]-2,3-dihydro-1H-pyrrolo[2,3-b]pyridine-2-carboxylic acid (2,3-dimethyl-phenyl)-amide;
(S)-1-[(S)-3-Methyl-2-((S)-2-methylamino-propionylamino)-butyryl]-2,3-dihydro-1H-pyrrolo[2,3-b]pyridine-2-carboxylic acid (2-fluoro-5-methyl-phenyl)-amide;
(S)-1-[(S)-3-Methyl-2-((S)-2-methylamino-propionylamino)-butyryl]-2,3-dihydro-1H-pyrrolo[2,3-b]pyridine-2-carboxylic acid (3,5-dimethyl-phenyl)-amide;
(S)-1-[(S)-3-Methyl-2-((S)-2-methylamino-propionylamino)-butyryl]-2,3-dihydro-1H-pyrrolo[2,3-b]pyridine-2-carboxylic acid (2-fluoro-4-methyl-phenyl)-amide;
(S)-1-[(S)-3-Methyl-2-((S)-2-methylamino-propionylamino)-butyryl]-2,3-dihydro-1H-pyrrolo[2,3-b]pyridine-2-carboxylic acid (2-fluoro-4-methoxy-phenyl)-amide;
(S)-1-[(S)-3-Methyl-2-((S)-2-methylamino-propionylamino)-butyryl]-2,3-dihydro-1H-pyrrolo[2,3-b]pyridine-2-carboxylic acid (2-cyano-phenyl)-amide;
3-Fluoro-4-({(S)-1-[(S)-3-methyl-2-((S)-2-methylaminopropionylamino)-butyryl]-2,3-dihydro-1H-pyrrolo[2,3-b]pyridine-2-carbonyl}-amino)-benzoic acid methyl ester;
(S)-1-[(S)-3-Methyl-2-((S)-2-methylamino-propionylamino)-butyryl]-2,3-dihydro-1H-pyrrolo[2,3-b]pyridine-2-carboxylic acid (2-fluoro-4-methanesulfonyl-phenyl)-amide;
(S)-1-[(S)-3-Methyl-2-((S)-2-methylamino-propionylamino)-butyryl]-2,3-dihydro-1H-pyrrolo[2,3-b]pyridine-2-carboxylic acid (2-methanesulfonyl-ethyl)-amide;
(S)-1-[(S)-3-Methyl-2-((S)-2-methylamino-propionylamino)-butyryl]-2,3-dihydro-1H-pyrrolo[2,3-b]pyridine-2-carboxylic acid (1-phenyl-ethyl)-amide;
(S)-1-[(S)-3-Methyl-2-((S)-2-methylamino-propionylamino)-butyryl]-2,3-dihydro-1H-pyrrolo[2,3-b]pyridine-2-carboxylic acid (2-dimethylsulfamoyl-ethyl)-amide;
(S)-1-[(S)-3-Methyl-2-((S)-2-methylamino-propionylamino)-butyryl]-2,3-dihydro-1H-pyrrolo[2,3-b]pyridine-2-carboxylic acid (1-methyl-1-phenyl-ethyl)-amide;
(S)-1-[(S)-3-Methyl-2-((S)-2-methylamino-propionylamino)-butyryl]-2,3-dihydro-1H-pyrrolo[2,3-b]pyridine-2-carboxylic acid 5-fluoro-2-methyl-benzylamide;
(S)-1-[(S)-3-Methyl-2-((S)-2-methylamino-propionylamino)-butyryl]-2,3-dihydro-1H-pyrrolo[2,3-b]pyridine-2-carboxylic acid pyrimidin-5-ylamide;
(S)-1-[(S)-3-Methyl-2-((S)-2-methylamino-propionylamino)-butyryl]-2,3-dihydro-1H-pyrrolo[2,3-b]pyridine-2-carboxylic acid naphthalen-2-ylamide;
(S)-1-[(S)-3-Methyl-2-((S)-2-methylamino-propionylamino)-butyryl]-2,3-dihydro-1H-pyrrolo[2,3-b]pyridine-2-carboxylic acid (4-cyano-2-fluoro-phenyl)-amide;
(S)-1-[(S)-3-Methyl-2-((S)-2-methylamino-propionylamino)-butyryl]-2,3-dihydro-1H-pyrrolo[2,3-b]pyridine-2-carboxylic acid (2-fluoro-4-trifluoromethyl-phenyl)-amide;
(S)-1-[(S)-3-Methyl-2-((S)-2-methylamino-propionylamino)-butyryl]-2,3-dihydro-1H-pyrrolo[2,3-b]pyridine-2-carboxylic acid (2,3-difluoro-phenyl)-amide;
(S)-1-[(S)-3-Methyl-2-((S)-2-methylamino-propionylamino)-butyryl]-2,3-dihydro-1H-pyrrolo[2,3-b]pyridine-2-carboxylic acid (2,5-difluoro-phenyl)-amide;
(S)-1-[(S)-3-Methyl-2-((S)-2-methylamino-propionylamino)-butyryl]-2,3-dihydro-1H-pyrrolo[2,3-b]pyridine-2-carboxylic acid (4-dimethylcarbamoyl-2-fluoro-phenyl)-amide;
(S)-1-[(S)-3-Methyl-2-((S)-2-methylamino-propionylamino)-butyryl]-2,3-dihydro-1H-pyrrolo[2,3-b]pyridine-2-carboxylic acid (4-bromo-2-fluoro-phenyl)-amide;
(S)-1-[(S)-3-Methyl-2-((S)-2-methylamino-propionylamino)-butyryl]-2,3-dihydro-1H-pyrrolo[2,3-b]pyridine-2-carboxylic acid (2-fluoro-4-methylcarbamoyl-phenyl)-amide;
(S)-1-[(S)-3-Methyl-2-((S)-2-methylamino-propionylamino)-butyryl]-2,3-dihydro-1H-pyrrolo[2,3-b]pyridine-2-carboxylic acid (2,4-difluoro-phenyl)-amide;
(S)-1-[(S)-3-Methyl-2-((S)-2-methylamino-propionylamino)-butyryl]-2,3-dihydro-1H-pyrrolo[2,3-b]pyridine-2-carboxylic acid (4-methyl-thiazol-2-yl)-amide;
(S)-1-[(S)-3-Methyl-2-((S)-2-methylamino-propionylamino)-butyryl]-2,3-dihydro-1H-pyrrolo[2,3-b]pyridine-2-carboxylic acid (5-methyl-thiazol-2-yl)-amide;
(S)-1-[(S)-3-Methyl-2-((S)-2-methylamino-propionylamino)-butyryl]-2,3-dihydro-1H-pyrrolo[2,3-b]pyridine-2-carboxylic acid benzothiazol-2-ylamide;
(S)-1-[(S)-3-Methyl-2-((S)-2-methylamino-propionylamino)-butyryl]-2,3-dihydro-1H-pyrrolo[2,3-b]pyridine-2-carboxylic acid (3-fluoro-pyridin-4-yl)-amide;
(S)-1-[(S)-3-Methyl-2-((S)-2-methylamino-propionylamino)-butyryl]-2,3-dihydro-1H-pyrrolo[2,3-b]pyridine-2-carboxylic acid (2-chloro-6-fluoro-phenyl)-amide;
(S)-1-[(S)-3-Methyl-2-((S)-2-methylamino-propionylamino)-butyryl]-2,3-dihydro-1H-pyrrolo[2,3-b]pyridine-2-carboxylic acid (2-chloro-6-methyl-phenyl)-amide;
(S)-1-[(S)-3-Methyl-2-((S)-2-methylamino-propionylamino)-butyryl]-2,3-dihydro 1H-pyrrolo[2,3-b]pyridine-2-carboxylic acid (2,4,6-trichloro-phenyl)-amide;
(S)-1-[(S)-3-Methyl-2-((S)-2-methylamino-propionylamino)-butyryl]-dihydro-1H-pyrrolo[2,3-b]pyridine-2-carboxylic acid (2-fluoro-6-trifluoromethyl-phenyl)-amide;
(S)-1-[(S)-3-Methyl-2-((S)-2-methylamino-propionylamino)-butyryl]-2,3-dihydro-1H-pyrrolo[2,3-b]pyridine-2-carboxylic acid (2,6-dichloro-phenyl)-amide;

(S)-1-[(S)-3-Methyl-2-((S)-2-methylamino-propionylamino)-butyryl]-2,3-dihydro-1H-pyrrolo[2,3-b]pyridine-2-carboxylic acid (2-chloro-6-trifluoromethyl-phenyl)-amide;

(S)-1-[(S)-2-Cyclohexyl-2-((S)-2-ethylamino-propionylamino)-acetyl]-2,3-dihydro-1H-pyrrolo[2,3-b]pyridine-2-carboxylic acid phenylamide;

(S)-1-[(S)-2-((S)-2-Ethylamino-propionylamino)-3-methyl-butyryl]-2,3-dihydro-1H-pyrrolo[2,3-b]pyridine-2-carboxylic acid (2,6-difluoro-phenyl)-amide;

(S)-1-[(S)-3-Methyl-2-((S)-2-methylamino-butyrylamino)-butyryl]-2,3-dihydro-1H-pyrrolo[2,3-b]pyridine-2-carboxylic acid (2,6-difluoro-phenyl)-amide;

(R)-1-[(S)-2-Cyclohexyl-2-((S)-2-methylamino-propionylamino)-acetyl]-2,3-dihydro-1H-pyrrolo[2,3-b]pyridine-2-carboxylic acid phenylamide;

(S)-1-[(S)-2-Cyclohexyl-2-((S)-2-methylamino-propionylamino)-acetyl]-2,3-dihydro-1H-pyrrolo[2,3-b]pyridine-2-carboxylic acid phenylamide;

(R)-1-[(S)-2-Cyclohexyl-2-((S)-2-methylamino-butyrylamino)-acetyl]-2,3-dihydro-1H-pyrrolo[2,3-b]pyridine-2-carboxylic acid phenylamide;

1-[(S)-2-Cyclohexyl-2-((S)-2-methylamino-butyrylamino)-acetyl]-2,3-dihydro-1H-pyrrolo[2,3-b]pyridine-2-carboxylic acid phenylamide;

1-[(S)-2-Cyclohexyl-2-((S)-2-(d3-methyl)amino-butyrylamino)-acetyl]-2,3-dihydro-1H-pyrrolo[2,3-b]pyridine-2-carboxylic acid phenylamide;

(S)-1-[(S)-2-((S)-2-Amino-propionylamino)-2-cyclohexyl-acetyl]-2,3-dihydro-1H-pyrrolo[2,3-b]pyridine-2-carboxylic acid phenylamide;

(S)-1-[(S)-3-Methyl-2-((S)-2-methylamino-butyrylamino)-butyryl]-2,3-dihydro-1H-pyrrolo[2,3-b]pyridine-2-carboxylic acid phenylamide;

(S)-1-[(S)-3-Methyl-2-((S)-2-(d3-methyl)amino-butyrylamino)-butyryl]-2,3-dihydro-1H-pyrrolo[2,3-b]pyridine-2-carboxylic acid phenylamide;

(S)-1-[(S)-2-((S)-2-Ethylamino-propionylamino)-3-methyl-butyryl]-2,3-dihydro-1H-pyrrolo[2,3-b]pyridine-2-carboxylic acid phenylamide;

(S)-1-[(S)-2-((S)-2-Ethylamino-butyrylamino)-3-methyl-butyryl]-2,3-dihydro-1H-pyrrolo[2,3-b]pyridine-2-carboxylic acid phenylamide;

(S)-1-{(S)-2-[(S)-2-(2-Hydroxy-ethylamino)-propionylamino]-3-methyl-butyryl}-2,3-dihydro-1H-pyrrolo[2,3-b]pyridine-2-carboxylic acid phenylamide;

(S)-1-{(S)-2-[(S)-2-(2-Hydroxy-ethylamino)-butyrylamino]-3-methyl-butyryl}-2,3-dihydro-1H-pyrrolo[2,3-b]pyridine-2-carboxylic acid phenylamide;

(S)-1-{(S)-2-Cyclohexyl-2-[(S)-2-(2-hydroxy-ethylamino)-propionylamino]-acetyl}-2,3-dihydro-1H-pyrrolo[2,3-b]pyridine-2-carboxylic acid phenylamide;

(S)-1-{(S)-2-[(S)-2-(2-Methanesulfonyl-ethylamino)-propionylamino]-3-methyl-butyryl}-2,3-dihydro-1H-pyrrolo[2,3-b]pyridine-2-carboxylic acid (2,6-difluoro-phenyl)-amide;

(S)-1-(S)-2-[(S)-2-(2-Methoxy-ethylamino)-propionylamino]-3-methyl-butyryl)-2,3-dihydro-1H-pyrrolo[2,3-b]pyridine-2-carboxylic acid (2,6-difluoro-phenyl)-amide;

(S)-1-[(S)-2-((S)-2-Methylamino-propionylamino)-2-(tetrahydro-pyran-4-yl)-acetyl]-2,3-dihydro-1H-pyrrolo[2,3-b]pyridine-2-carboxylic acid (2,6-difluoro-phenyl)-amide;

(R)-1-[(S)-2-((S)-2-Methylamino-propionylamino)-2-(tetrahydro-pyran-4-yl)-acetyl]-2,3-dihydro-1H-pyrrolo[2,3-b]pyridine-2-carboxylic acid (2,6-difluoro-phenyl)-amide;

1-[(S)-4-Methanesulfonyl-2-((S)-2-methylamino-propionylamino)-butyryl]-2,3-dihydro-1H-pyrrolo[2,3-b]pyridine-2-carboxylic acid phenylamide;

1-[(S)-4-Methanesulfonyl-2-((S)-2-methylamino-propionylamino)-butyryl]-2,3-dihydro-1H-pyrrolo[2,3-b]pyridine-2-carboxylic acid phenylamide;

3-Methyl-1-[(S)-3-methyl-2-((S)-2-methylamino-propionylamino)-butyryl]-2,3-dihydro-1H-pyrrolo[2,3-b]pyridine-2-carboxylic acid (2,6-difluoro-phenyl)-amide;

(S)-1-[(S)-2-((S)-2-Methylamino-propionylamino)-2-(tetrahydro-pyran-4-yl)-acetyl]-2,3-dihydro-1H-pyrrolo[2,3-b]pyridine-2-carboxylic acid (2-fluoro-6-methyl-phenyl)-amide; or a pharmaceutically acceptable salt of any of the foregoing compounds.

27. The compound of claim 1 selected from the group consisting of (S)—N—{(S)-1-[(S)-2-(1H-Benzoimidazol-2-yl)-2,3-dihydro-pyrrolo[2,3-b]pyridine-1-carbonyl]-2-methyl-propyl}-2-methylamino-propionamide; and (S)—N—{(S)-1-[(R)-2-(1H-Benzoimidazol-2-yl)-2,3-dihydro-pyrrolo[2,3-b]pyridine-1-carbonyl]-2-methyl-propyl}-2-methylamino-propionamide; or a pharmaceutically acceptable salt of any of the foregoing compounds.

28. The compound of claim 1 selected from the group consisting of:

(S)—N—[(S)-1-(3,3-Dimethyl-2,3-dihydro-pyrrolo[2,3-b]pyridine-1-carbonyl)-2-methyl-propyl]-2-methylamino-propionamide; and (S)—N—[(S)-1-(3,3-Dimethyl-2,3-dihydro-pyrrolo[2,3-b]pyridine-1-carbonyl)-2-methyl-propyl]-2-methylamino-butyramide; or a pharmaceutically acceptable salt of any of the foregoing compounds.

29. The compound according to claim 1 selected from the group consisting of:

(S)—N—[(S)-1-(3,3-Dimethyl-2,3-dihydro-pyrrolo[2,3-b]pyridine-1-carbonyl)-2-methyl-propyl]-2-methylamino-butyramide;

(S)-1-[(S)-3-Methyl-2-((S)-2-methylamino-propionylamino)-butyryl]-2,3-dihydro-1H-pyrrolo[2,3-b]pyridine-2-carboxylic acid o-tolylamide;

(S)-1-[(S)-3-Methyl-2-((S)-2-methylamino-propionylamino)-butyryl]-2,3-dihydro-1H-pyrrolo[2,3-b]pyridine-2-carboxylic acid (2-chloro-phenyl)-amide;

(S)-1-[(S)-3-Methyl-2-((S)-2-methylamino-propionylamino)-butyryl]-2,3-dihydro-1H-pyrrolo[2,3-b]pyridine-2-carboxylic acid (2,6-difluoro-phenyl)-amide;

(S)-1-[(S)-3-Methyl-2-((S)-2-methylamino-propionylamino)-butyryl]-2,3-dihydro-1-pyrrolo[2,3-b]pyridine-2-carboxylic acid (2-fluoro-6-methyl-phenyl)-amide;

(S)-1-[(S)-3-Methyl-2-((S)-2-methylamino-propionylamino)-butyryl]-2,3-dihydro-1H-pyrrolo[2,3-b]pyridine-2-carboxylic acid (2-fluoro-phenyl)-amide;

(S)-1-[(S)-3-Methyl-2-((S)-2-methylamino-propionylamino)-butyryl]-2,3-dihydro-1H-pyrrolo[2,3-b]pyridine-2-carboxylic acid (2-fluoro-5-methyl-phenyl)-amide;

(S)-1-[(S)-3-Methyl-2-((S)-2-methylamino-propionylamino)-butyryl]-2,3-dihydro-1H-pyrrolo[2,3-b]pyridine-2-carboxylic acid (2-fluoro-4-methyl-phenyl)-amide;

(S)-1-[(S)-3-Methyl-2-((S)-2-methylamino-propionylamino)-butyryl]-2,3-dihydro-1H-pyrrolo[2,3-b]pyridine-2-carboxylic acid (2-fluoro-4-methoxy-phenyl)-amide;

(S)-1-[(S)-3-Methyl-2-((S)-2-methylamino-propionylamino)-butyryl]-2,3-dihydro-1H-pyrrolo[2,3-b]pyridine-2-carboxylic acid (2,5-difluoro-phenyl)-amide;

(S)-1-[(S)-3-Methyl-2-((S)-2-methylamino-propionylamino)-butyryl]-2,3-dihydro-1H-pyrrolo[2,3-b]pyridine-2-carboxylic acid (4-bromo-2-fluoro-phenyl)-amide;

(S)-1-[(S)-3-Methyl-2-((S)-2-methylamino-propionylamino)-butyryl]-2,3-dihydro-1H-pyrrolo[2,3-b]pyridine-2-carboxylic acid (2-chloro-6-fluoro-phenyl)-amide;

(S)-1-[(S)-3-Methyl-2-((S)-2-methylamino-propionylamino)-butyryl]-2,3-dihydro-1H-pyrrolo[2,3-b]pyridine-2-carboxylic acid (2-chloro-6-methyl-phenyl)-amide;

(S)-1-[(S)-3-Methyl-2-((S)-2-methylamino-propionylamino)-butyryl]-2,3-dihydro 1H-pyrrolo[2,3-b]pyridine-2-carboxylic acid (2,4,6-trichloro-phenyl)-amide;

(S)-1-[(S)-3-Methyl-2-((S)-2-methylamino-propionylamino)-butyryl]-2,3-dihydro-1H-pyrrolo[2,3-b]pyridine-2-carboxylic acid (2,6-dichloro-phenyl)-amide;

(S)-1-[(S)-3-Methyl-2-((S)-2-methylamino-butyrylamino)-butyryl]-2,3-dihydro-1H-pyrrolo[2,3-b]pyridine-2-carboxylic acid (2,6-difluoro-phenyl)-amide;

(S)-1-[(S)-2-((S)-2-Methylamino-propionylamino)-2-(tetrahydro-pyran-4-yl)-acetyl]-2,3-dihydro-1H-pyrrolo[2,3-b]pyridine-2-carboxylic acid (2,6-difluoro-phenyl)-amide;

3-Methyl-1-[(S)-3-methyl-2-((S)-2-methylamino-propionylamino)-butyryl]-2,3-dihydro-1H-pyrrolo[2,3-b]pyridine-2-carboxylic acid (2,6-difluoro-phenyl)-amide; and (5)-1-[(S)-2-((S)-2-Methylamino-propionylamino)-2-(tetrahydro-pyran-4-yl)-acetyl]-2,3-dihydro-1H-pyrrolo[2,3-b]pyridine-2-carboxylic acid (2-fluoro-6-methyl-phenyl)-amide; or a pharmaceutically acceptable salt of any of the foregoing compounds.

30. A pharmaceutical composition, comprising a therapeutically effective amount of a compound according to claim 1, or a pharmaceutically acceptable salt thereof, as an active ingredient together with a pharmaceutically acceptable carrier or excipient.

\* \* \* \* \*

SEQUENCE LISTING

<160> NUMBER OF SEQ ID NOS: 3

<210> SEQ ID NO 1
<211> LENGTH: 10
<212> TYPE: PRT
<213> ORGANISM: Artificial Sequence
<220> FEATURE:
<223> OTHER INFORMATION: TR-FRET peptide

<400> SEQUENCE: 1

Ala Val Pro Ile Ala Gln Lys Ser Glu Lys
1               5                   10

<210> SEQ ID NO 2
<211> LENGTH: 125
<212> TYPE: PRT
<213> ORGANISM: Artificial Sequence
<220> FEATURE:
<223> OTHER INFORMATION: TR-FRET peptide

<400> SEQUENCE: 2

Met Arg His His His His His His Arg Asp His Phe Ala Leu Asp Arg
1               5                   10                  15

Pro Ser Glu Thr His Ala Asp Tyr Leu Leu Arg Thr Gly Gln Val Val
            20                  25                  30

Asp Ile Ser Asp Thr Ile Tyr Pro Arg Asn Pro Ala Met Tyr Ser Glu
        35                  40                  45

Glu Ala Arg Leu Lys Ser Phe Gln Asn Trp Pro Asp Tyr Ala His Leu
    50                  55                  60

Thr Pro Arg Glu Leu Ala Ser Ala Gly Leu Tyr Tyr Thr Gly Ile Gly
65                  70                  75                  80

Asp Gln Val Gln Cys Phe Ala Cys Gly Gly Lys Leu Lys Asn Trp Glu
                85                  90                  95

Pro Gly Asp Arg Ala Trp Ser Glu His Arg Arg His Phe Pro Asn Cys
            100                 105                 110

Phe Phe Val Leu Gly Arg Asn Leu Asn Ile Arg Ser Glu
        115                 120                 125

<210> SEQ ID NO 3
<211> LENGTH: 125
<212> TYPE: PRT
<213> ORGANISM: Artificial Sequence
<220> FEATURE:
<223> OTHER INFORMATION: TR-FRET peptide

<400> SEQUENCE: 3

Met Arg His His His His His His Arg Ser Asp Ala Val Ser Ser Asp
1               5                   10                  15

Arg Asn Phe Pro Asn Ser Thr Asn Leu Pro Arg Asn Pro Ser Met Ala
            20                  25                  30

Asp Tyr Glu Ala Arg Ile Phe Thr Phe Gly Thr Trp Ile Tyr Ser Val
        35                  40                  45

Asn Lys Glu Gln Leu Ala Arg Ala Gly Phe Tyr Ala Leu Gly Glu Gly
    50                  55                  60

Asp Lys Val Lys Cys Phe His Cys Gly Gly Gly Leu Thr Asp Trp Lys
65                  70                  75                  80

| | | | | | | | | | | | | | | |
|---|---|---|---|---|---|---|---|---|---|---|---|---|---|---|
|Pro|Ser|Glu|Asp|Pro|Trp|Glu|Gln|His|Ala|Lys|Trp|Tyr|Pro|Gly Cys|
| | | | |85| | | |90| | | | |95| |
|Lys|Tyr|Leu|Leu|Glu|Gln|Lys|Gly|Gln|Glu|Tyr|Ile|Asn|Asn|Ile His|
| | | |100| | | |105| | | |110| | | |
|Leu|Thr|His|Ser|Leu|Glu|Glu|Cys|Leu|Val|Arg|Thr|Thr| | |
| | |115| | | | |120| | | |125| | | |